(12) United States Patent
Buonatesta et al.

(10) Patent No.: US 8,871,923 B2
(45) Date of Patent: Oct. 28, 2014

(54) COMPOSITION COMPRISING AN ELICITOR OF THE PLANT IMMUNE SYSTEM

(75) Inventors: Raffaele Buonatesta, Auvelais (BE); Géraldine Van Aubel, Marneffe (BE); Pierre Van Cutsem, Ottignies (BE)

(73) Assignee: FYTOFEND S.A., Isnes (BE)

( * ) Notice: Subject to any disclaimer, the term of this patent is extended or adjusted under 35 U.S.C. 154(b) by 0 days.

(21) Appl. No.: 13/980,432

(22) PCT Filed: Jan. 24, 2012

(86) PCT No.: PCT/EP2012/051018
§ 371 (c)(1),
(2), (4) Date: Jul. 18, 2013

(87) PCT Pub. No.: WO2012/101106
PCT Pub. Date: Aug. 2, 2012

(65) Prior Publication Data
US 2013/0302437 A1 Nov. 14, 2013

(30) Foreign Application Priority Data

Jan. 24, 2011 (EP) .................................... 11151836

(51) Int. Cl.
| | | |
|---|---|---|
| *A01N 57/00* | (2006.01) | |
| *A01N 47/24* | (2006.01) | |
| *A01N 47/12* | (2006.01) | |
| *A01N 43/40* | (2006.01) | |
| *A01N 43/16* | (2006.01) | |
| *A01N 43/42* | (2006.01) | |
| *A01N 43/56* | (2006.01) | |
| *C07H 3/06* | (2006.01) | |
| *C07H 5/06* | (2006.01) | |
| *C08B 37/06* | (2006.01) | |
| *C08B 37/08* | (2006.01) | |
| *C08B 37/00* | (2006.01) | |
| *A01N 57/10* | (2006.01) | |
| *A01N 59/00* | (2006.01) | |
| *A01N 59/02* | (2006.01) | |

(52) U.S. Cl.
CPC .............. *A01N 43/16* (2013.01); *C08B 37/003* (2013.01); *C07H 3/06* (2013.01); *C07H 5/06* (2013.01); *C08B 37/0045* (2013.01); *A01N 47/12* (2013.01); *A01N 47/24* (2013.01); *A01N 43/40* (2013.01); *A01N 43/42* (2013.01); *A01N 43/56* (2013.01); *A01N 57/10* (2013.01); *A01N 59/00* (2013.01); *A01N 59/02* (2013.01)
USPC ...................................... 536/55.1; 536/123.1

(58) Field of Classification Search
CPC ................................ C07H 5/06; C08B 37/003
See application file for complete search history.

(56) References Cited

U.S. PATENT DOCUMENTS 6,770,303 B1    8/2004   Fritig et al.

FOREIGN PATENT DOCUMENTS

| EP | 1358801 A1 | 11/2003 | | |
|---|---|---|---|---|
| JP | 59128301 A | 7/1984 | | |
| WO | WO98/47375 | * 10/1998 | ............. | A01N 65/00 |
| WO | 9953761 A1 | 10/1999 | | |
| WO | 2008065151 A1 | 6/2008 | | |
| WO | WO2010/057754 | * 5/2010 | ........... | A01N 43/653 |

OTHER PUBLICATIONS

Sigma-Aldrich product information for Tween® 20, published May 2006 by Signa-Aldrich, Inc.*
Morton et al., "A short History of Fungicides" downloaded from www.aspnet.org, published 2008.*
Zhao et al., "Elicitor signal transduction leading to production of plant secondary metabolites" Biotechnology Advances (2005) vol. 23 pp. 283-333.*
Remus-Borel et al., "Silicon induces antifungal compounds in powdery mildew-infected wheat" Physiological and Molecular Plant Pathology (2006) vol. 66 pp. 108-115.*
International Search Report, dated Mar. 8, 2012 in connection with PCT International Application No. PCT/EP2012/051018, 3 pages.
Notification of Transmittal of the International Preliminary Report on Patentability dated Apr. 30, 2013 in connection with PCT International Application No. PCT/EP2012/051018, 6 pages, and reply filed on Apr. 9, 2013, including Claims 1-44 (10 pages).
Rodriguez M S et al., entitled "New chitosan-calcium pectinate pellets and their adsorption capacity," Colloid Polym Sci (2006) 285:119-124.
Chang K L B et al, entitled "Swelling behavior and the release of protein from chitosan-pectin composite particles," Carbohydrate Polymers 43 (2000) 163-169.

* cited by examiner

*Primary Examiner* — Eric Olson
(74) *Attorney, Agent, or Firm* — Amster, Rothstein & Ebenstein LLP

(57) ABSTRACT

The present invention generally relates to new plant elicitor compositions, and the use of these compositions in agricultural applications, more particularly to protect plants against (infection by) plant pathogens and the corresponding methods of, and uses in, the protection of plants and crops by application of these compositions.

29 Claims, 21 Drawing Sheets

COMPOSITION COMPRISING AN ELICITOR OF THE PLANT IMMUNE SYSTEM

CROSS-REFERENCE TO RELATED APPLICATIONS

This application is a U.S. national stage entry under 35 U.S.C. §371 of PCT International Patent Application No. PCT/EP2012/051018, filed Jan. 24, 2012, which claims priority to European Patent Application No. 11151836.1, filed Jan. 24, 2011, the contents of which are incorporated herein by reference in their entirety.

FIELD OF THE INVENTION

The present invention generally relates to new compositions for protecting plants against plant pathogens, essentially comprising a particular plant elicitor, and the use of these compositions in agricultural applications, more particularly to protect plants against (infection by) plant pathogens and the corresponding methods of, and uses in, the protection of plants and crops by application of these compositions.

BACKGROUND OF THE INVENTION

Plant pathogens can cause serious damage in agriculture, resulting in critical losses of yield, quality and profit. Examples are phytopathogenic fungi the majority of which belong to the Ascomycetes, including the causal agents of powdery mildew of various plants, the Basidiomycetes, including the causal agents of severe rusts of virtually all cereal grains and cultivated grasses and the Deuteromycetes (Fungi imperfecti), including *Fusarium, Bohytis* and *Verticillium*. Further pathogens are Oomycetes, which are not true fungi but fungal-like organisms that use the same mechanisms as fungi to infect plants. They include some of the most destructive plant pathogens including *Phytophthora infestans*, the causal agent of potato late blight and *Plasmopara viticola*, the causal agent of grapevine downy mildew. Besides fungi, also bacteria including the genii *Erwinia, Xanthomonas, Pseudomonas* and *Ralstonia*, viruses including Cucumber Mosaic Virus, Barley Yellow Mosaic Virus, Strawberry Mild Yellow Edge Virus, Strawberry Latent Ringspot Virus, Beet Necrotic Yellow Vein Virus and Potato Virus Y, insects including beetles, rootworms, hoppers, locusts, (stem) borers, aphids, mites, thicks, ants, whiteflies, maggots, weevils, midges, caterpillars, butterflies, leaf miners, leaf rolers, bugs, and plasmodiophorid protists including the genii *Polymyxa, Plasmodiophora* and *Spongospora* are important plant pathogens.

Plants respond to infection by pathogens by activating their innate immune system. The plant defense systems recognize molecular patterns that are common to many classes of pathogens, e.g. fungal chitin, and may respond to pathogen-specific virulence factors (effectors). Pathogen recognition triggers ion channel gating, oxidative burst, cellular redox changes, protein kinase cascades and other responses that either directly activate cellular changes such as cell wall reinforcement, or activate changes in gene expression that lead to the formation of defensive compounds, e.g. directed to fight infection or to make the plant less attractive to pathogens.

The role of peroxidases in plant protection against pathogens is of the utmost importance. Peroxidases undergo two possible catalytic cycles involving either the consumption or the release of $H_2O_2$ and reactive oxygen species. Reactive oxygen species can act directly on pathogens and $H_2O_2$ is further known to be a mediator of signal transduction in the establishment of plant defense. Moreover, peroxidases can control the availability of $H_2O_2$ in the cell wall, which is a prerequisite for the crosslinking of phenolic groups in the cell wall. The peroxidase mediated crosslinking of different compounds in the cell wall ensures reinforcement of the barrier against pathogen penetration. Peroxidases are also known to be involved in the production of phytoalexins, which are antibiotic compounds produced by plants under stress conditions.

Thus, it is of interest to stimulate the plant immune system in order to control diseases caused by parasites or pathogens such as fungi, oomycetes, bacteria, viruses, nematodes and insects.

Fungal diseases and diseases caused by oomycetes can also be controlled through the use of fungicides in agriculture. Fungicides are chemical compounds or biological substances used to kill or inhibit fungi or oomycetes or their spores. Fungicides sometimes also have an effect on other plant pathogens such as bacteria, viruses, nematodes or insects. A drawback of using certain fungicides is that fungicide residues can be found on food for human consumption, sometimes posing a danger to human or animal health.

Therefore, it is of high-interest in agriculture to improve the performances of chemical fungicides, in particular in terms of biological activity, with the aim of decreasing the amounts of active ingredient to be used.

SUMMARY OF THE INVENTION

The inventors have now unexpectedly found that by adding an oligosaccharidic plant immune system elicitor comprising oligo-galacturonans stabilized by chito-oligosaccharides, to certain fungicides, the efficacy of the fungicide is amplified. This implies that using the elicitor composition of the present invention results in a high reduction in the amount of fungicides needed due to the enhanced potency thereof. Applying the fungicide at a reduced rate, leads to a reduced amount of fungicidal residues on the plants, which is beneficial for human and animal health and the environment in general. Furthermore, by addition of the elicitor, the plant immune system is triggered, particularly reflected by its increased peroxidase activity, which is not achieved through application of the fungicide alone. This synergistic effect of the elicitor on the fungicide renders the plant more resistant to attacks of pathogens and will in the long run thus provide for an increased yield of the crop.

Thus, in a first aspect the present invention relates to a composition for protecting plants against (infection by) plant pathogens comprising:

a) an elicitor comprising: one or more oligo-galacturonan(s) with a degree of polymerization between 9 and 20, and one or more chito-oligosaccharide(s) with a degree of polymerization higher than 5 and a degree of acetylation lower than 50%, in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, and b) a fungicide, preferably a fungicide selected from the group comprising: phosphonates, benzamides carbamates, dithiocarbamates, phtalimides, triazoles, quinolines, sulphur, and cyanoimidazoles, c) optionally salts and/or sugar, wherein said fungicide is present in a concentration which is reduced by at least a factor 2, 3, 4, 5, 6, 7, 8, 9, 10, 15, 25, 40, 50, 60, 70, 80, 90, 100 or 200 when compared to the recommended concentration for said plant and/or conditions. More preferably, said elicitor comprises: one or more oligo-galacturonan(s) with a degree of polymerization between 9 and 20, and one or more chito-oligosaccharide(s) with a degree of polymerization between 5 and 10 and a degree of acetylation about 25%, in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts.

In an embodiment, the composition of the invention comprises a phosphonate fungicide. In another embodiment, the composition of the invention comprises a benzamide fungicide. In another embodiment, the composition of the invention comprises a carbamate fungicide. In another embodiment, the composition of the invention comprises a dithiocarbamate fungicide. In another embodiment, the composition of the invention comprises a phthalimide fungicide. In another embodiment, the composition of the invention comprises a triazole fungicide. In another embodiment, the composition of the invention comprises a quinoline fungicide. In another embodiment, the composition of the invention comprises a sulphur-containing fungicide. In another embodiment, the composition of the invention comprises a cyanoimidazole fungicide.

The composition according to the invention may further comprise a co-formulant selected from the group comprising: surfactants, anti-freeze agents (urea, ethylene glycol, propylene glycol or glycerol), preservative agents (potassium sorbate, paraben and its derivates, 1,2-benzisothiazol-3(2H)-one or essential oils), absorbent agents (including raids of corn or sawdust), thickeners (including clays or xanthane gum), buffers, sticker agents (including latex, silicon or alkoxylated alkyl), diluents (including rapeseed methyl ester) or a mixture thereof.

In a preferred embodiment, said co-formulant is a surfactant selected from the group comprising: detergents, emulsifiers (alkyl polyglucosides, glycerol ester or polyoxyethylene (20) sorbitan monolaurate (polysorbate 20)), dispersing agents (sodium chloride, potassium chloride, potassium nitrate, calcium chloride or starch of corn), anti-foaming agents (derivates of tartric acid, malic acid or alcohols), penetration enhancers, humectants (ammonium sulfate, glycerin or urea) or wetting agents of ionic or non-ionic type, or a mixture thereof. More preferably, said surfactant comprises one or more of the following components: castor oil ethoxylate, rapeseed methyl ester, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyoxyethylene (20) sorbitan monolaurate. Most preferably said surfactant is C18-castor-oil-ethoxylate (Dehscofix®), organic sulfonate/2-methylpentane-2,4-diol (Tensiofix Dp400) or polyoxyethylene (20) sorbitan monolaureate (Tween®20-).

In a further embodiment of the invention, the fungicide in the composition of the invention can be selected from the group comprising acylalanines (benalaxyl), anilinopyrimidines (cyprodinil or pyrimethanil), benzamides (fluopicolide or zoxamide), benzimidazoles (fuberidazole, thiabendazole or metrafenone), benzothiadiazoles (acibenzolar-5-methyl), carbamates (benthiavalicarb, iprovalicarb or propamocarb), carboxamides (boscalid), chloronitriles (chlorothalonil), chlorophenyls (tolclophos-methyl), cyanoacetamide oximes (cymoxanil), cyanoimidazoles (cyazofamid), dicarboximides (iprodione), dithiocarbamates (thiram, metiram, mancozeb, manebe or propineb), guanidines (dodine), hydroxyanilides (fenhexamid), imidazoles (fenamidone, imazalil or triflumizole), morpholines (dimethomorph, fenpropimorph, spiroxamine or dodemorph), phosphonates (fosetyl), oxathiins (flutolanil), oxazoles (famoxadone or hymexazol), phenylamides (metalaxyl or metalaxy-M), phenylpyridinamides (fluazinam), phenylpyrroles (fludioxonil), phtalimides (captan or folpet), quinazolinones (proquinazide), quinolines (quinoxyfen), strobilurins (dimoxystrobin, fluoxastrobin, kresoximmethyl, pyraclostrobin, trifloxystrobin or picoxystrobin), thiophenes (silthiofam), triazoles (difenoconazole, epoxyconazole, fenbuconazole, flusilazole, metconazole, myclobutanil, penconazole, propiconazole, tebuconazole, tetraconazole, triadimenol, triticonazole or prothioconazole), copper derivates (copper oxychloride, copper hydrochloride, copper oxide or copper sulphate) and sulphur.

In a preferred embodiment of the composition according to the invention, the fungicide is selected from the group comprising: phosphonates, benzamides, carbamates, dithiocarbamates, phtalimides, triazoles, quinolines, sulphur, and cyanoimidazoles. More preferably, said fungicide comprises ethylhydrogenphosphonate (fosetyl), preferably fosetyl-Al, fosetyl-Na or fosetyl-K, 2,6-dichloro-N-[3-chloro-5-(trifluoromethyl)-2-pyridinylmethyl]benzamide (fluopicolid), propyl 3-(dimethylamino)propylcarbamate hydrochloride (propamocarb), manganese ethylenebis(dithiocarbamate) (polymeric) complex with zinc salt (mancozeb), N-(trichloromethylthio)phthalimide (folpet), (2RS,3SR)-1-[3-(2-chlorophenyl)-2,3-epoxy-2-(4-fluorophenyl)propyl]-1H-1,2,4-triazole (epoxyconazole), 5,7-dichloro-4-quinolyl 4-fluorophenyl ether (quinoxyfen), sulphur, 4-chloro-2-cyano-N,N-dimethyl-5-(4-methylphenyl)-1H-imidazole-1-sulfonamide (cyazofamid) or a combination thereof.

In a preferred embodiment, said composition according to the invention comprises a further plant immune system elicitor selected from the group comprising: silica, copper, sulfur, aluminium, vanadium, cobalt, nickel, iron, silver, salicylic acid and its derivates (including acetyl-salicylic acid, isonicotinic acid, acibenzolar-5-methyl), jasmonic acid and its derivates (including methyl jasmonate), ethylene and its derivates, polysaccharides (including glucans, xyloglucans, chitin, chitosans, fucans, galactofucans, xylans, galactans, alginates, galacturonans, apiogalacturonans, fructans including inulin, mannans, xylomannans, galactomannans, glucomannans and galactomannans), algae extracts (green algae extracts including ulvans, brown algae extracts including laminarin, and red algae extracts including carragenans), oligosaccharides (including trehalose), peptides (including systemin, 13-pep, flg-22, glutathion), amino acids, proteins (including harpin and flagellin), peptone, beef extract, essential oils (including cumin, anise, mint, cinnamon, thyme, basil, cardamom, coriander, oregano, manzanilla, clove, jojoba and tea tree oils), lipids (including ergosterol, amphotericin, sphingolipids, cerebrosides), glycolipids (including syringolids), glycoproteins (including cryptogeins), lipopeptides, lipoproteins (including volicitin), yeast extracts (including extracts from *Saccharomyces, Candida, Pichia, Aureobasidium* and more particularly *Saccharomyces cerevisiae, Candida famata, Candida oleophila, Pichia guilliermondii, Aureobasidium pullulans*), fungal extracts (including extracts from *Trichoderma, Megasperma, Pyricularia, Alternaria, Pythium, Puccinia, Colletotrichum, Verticillium, Magnaporthe*), bacterial extracts (including extracts from *Escherichia, Rhyzobia, Pseudomonas*), BABA, probenazole, isothianil, phosphorous acid and its derivates (including aluminium, sodium and potassium fosetyl), horsetail extracts, potassium iodide and potassium thiocyanate, *Citrus* extracts, *Yucca* extracts *Salix* extracts and plant decoctions (including nettle decoction). More preferably, said further plant immune system elicitor comprises laminarin.

In another preferred embodiment, said elicitor composition according to the invention comprises a further plant immune system elicitor that contains silicon, preferably said further plant immune system elicitor is a silicate, more preferably sodium silicate.

The composition according to the present invention can also be composed as follows:
- a) an elicitor comprising: one or more oligo-galacturonan(s) with a degree of polymerization between 9 and 20, and one or more chito-oligosaccharide(s) with a degree of polymerization higher than 5 and a degree of acetylation lower than 50% (preferably with a degree of polymerization between 5 and 10 and a degree of acetylation of about 25%), in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, and
- b) an adjuvant, preferably a surfactant selected from the group comprising: detergents, emulsifiers (alkyl polyglucosides, glycerol ester or polyoxyethylene (20) sorbitan monolaurate), dispersing agents (sodium chloride, potassium chloride, potassium nitrate, calcium chloride or starch of corn), anti-foaming agents (derivates of tartric acid, malic acid or alcohols), penetration enhancers, humectants (ammonium sulfate, glycerin or urea) or wetting agents of ionic or non-ionic type. More preferably, said surfactant comprises one or more of the following components: castor oil ethoxylate, rapeseed methyl ester, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyethylene (20) sorbitan monolaureate, even more preferably said surfactant is Dehscofix®, Tensiofix Dp400 or Tween®20.

Additionally, other co-formulants may be present in the composition, such as anti-freeze agents (urea, glycol ethylene, glycol propylene or glycerol), preservative agents (potassium sorbate, paraben and its derivates, 1,2-benzisothiazol-3(2H)-one or essential oils), absorbent agents (including raids of corn or sawdust), thickeners (including clays or xanthane gum), buffers, sticker agents (including latex, silicon or alkoxylated alkyl), diluents (including rapeseed methyl ester) or a mixture thereof.

Said composition comprising the elicitor and an adjuvant as defined above, may also comprise additionally a fungicide, further elicitor and/or further adjuvants as defined herein.

Alternatively, the composition according to the present invention can also be composed as follows:
- a) an elicitor comprising: one or more oligo-galacturonan(s) with a degree of polymerization between 9 and 20, and one or more chito-oligosaccharide(s) with a degree of polymerization higher than 5 and a degree of acetylation lower than 50% (preferably with a degree of polymerization between 5 and 10 and a degree of acetylation of about 25%), in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, and
- b) a further elicitor selected from the group comprising: silica, a silicate, sodium silicate, copper, sulfur, aluminium, vanadium, cobalt, nickel, iron, silver, salicylic acid and its derivates (including acetyl-salicylic acid, isonicotinic acid, acibenzolar-5-methyl), jasmonic acid and its derivates (including methyl jasmonate), ethylene and its derivates, polysaccharides (including glucans, xyloglucans, chitin, chitosans, fucans, galactofucans, xylans, galactans, alginates, galacturonans, apiogalacturonans, fructans including inulin, mannans, xylomannans, galactomannans, glucomannans and galactomannans), algae extracts (green algae extracts including ulvans, brown algae extracts including laminarin, and red algae extracts including carragenans), oligosaccharides (including trehalose), peptides (including systemin, 13-pep, flg-22, glutathion), amino acids, proteins (including harpin and flagellin), peptone, beef extract, essential oils (including cumin, anise, mint, cinnamon, thyme, basil, cardamom, coriander, oregano, manzanilla, clove, jojoba and tea tree oils), lipids (including ergosterol, amphotericin, sphingolipids, cerebrosides), glycolipids (including syringolids), glycoproteins (including cryptogeins), lipopeptides, lipoproteins (including volicitin), yeast extracts (including extracts from *Saccharomyces, Candida, Pichia, Aureobasidium* and more particularly *Saccharomyces cerevisiae, Candida famata, Candida oleophila, Pichia guilliermondii, Aureobasidium pullulans*), fungal extracts (including extracts from *Trichoderma, Megasperma, Pyricularia, Alternaria, Pythium, Puccinia, Colletotrichum, Verticillium, Magnaporthe*), bacterial extracts (including extracts from *Escherichia, Rhyzobia, Pseudomonas*), BABA, probenazole, isothianil, phosphorous acid and its derivates (including aluminium, sodium and potassium fosetyl), horsetail extracts, potassium iodide and potassium thiocyanate, *Citrus* extracts, *Yucca* extracts *Salix* extracts and plant decoctions (including nettle decoction). More preferably, said further plant immune system elicitor comprises laminarin.

Said composition comprising the two different elicitors as defined above, may also comprise additionally a fungicide, further elicitor and/or an adjuvant or surfactant as defined herein.

In yet another alternative, the composition according to the present invention can be composed as follows:
- a) an elicitor comprising: one or more oligo-galacturonan(s) with a degree of polymerization between 9 and 20, and one or more chito-oligosaccharide(s) with a degree of polymerization higher than 5 and a degree of acetylation lower than 50% (preferably with a degree of polymerization between 5 and 10 and a degree of acetylation of about 25%), in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, and
- b) a second elicitor that contains silicon, preferably said second elicitor is a silicate, more preferably said second elicitor is sodium silicate.

Said composition comprising the two different elicitors as defined above, may also comprise additionally a fungicide, further elicitor and/or an adjuvant or surfactant as defined herein.

In a preferred embodiment, said composition comprises:
- a) an elicitor comprising: one or more oligo-galacturonan(s) with a degree of polymerization between 9 and 20, and one or more chito-oligosaccharide(s) with a degree of polymerization higher than 5 and a degree of acetylation lower than 50% (preferably with a degree of polymerization between 5 and 10 and a degree of acetylation of about 25%), in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, and
- b) a second elicitor that contains silicon, preferably said second elicitor is a silicate, more preferably said second elicitor is sodium silicate, and
- c) a surfactant, preferably a surfactant selected from the group comprising Dehscofix®, Tensiofix Dp400, Radia® and Tween® 20, preferably Tween® 20.

The invention further provides for the use of any one of the compositions according to the present invention in agricultural applications, particularly to protect plants against (infection by) plant pathogens, preferably phytopathogenic fungi, oomycetes, bacteria, viruses, nematodes, insects, and/ or aphids, more preferably to enhance the efficacy of the fungicide or to stimulate the plant innate immune system.

The invention additionally provides a method for protecting plants against (infection by) plant pathogens such as phytopathogenic fungi, oomycetes, bacteria, viruses, nematodes, insects, and/or aphids, comprising applying an effective and substantially non-phytotoxic amount of any one of the compositions according to the invention to said plants.

The invention further provides a method for enhancing the fungicidal activity of a fungicide, comprising adding any one of the compositions according to the invention comprising one or more oligo-galacturonan(s) with a degree of polymerization between 9 and 20 and one or more chito-oligosaccharide(s) with a degree of polymerization higher than 5 and a degree of acetylation lower than 50% (preferably with a degree of polymerization between 5 and 10 and a degree of acetylation of about 25%) in varying proportions to a fungicidal composition.

In a preferred embodiment of said method, the composition of the invention is applied before harvest or post harvest to the whole plant, the leaves, the flowers, fruits, seeds, seedlings or seedlings pricking out, propagation material such as tubers or rhizomes, plants pricking out, and/or to the soil or inert substrate wherein the plant is growing or in which it is desired to grow, by spraying, drenching, soaking, dipping, injection or administration through fertilising or irrigation systems.

Preferably, the plant is selected from the group comprising: cotton, flax, vine, fruit, vegetable, major horticultural and forest crops such as: *Rosaceae* sp., *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp., *Rubiaceae* sp., *Theaceae* sp., *Sterculiceae* sp., *Rutaceae* sp., *Solanaceae* sp., *Vitaceae* sp. *Liliaceae* sp., *Asteraceae* sp., *Umbelliferae* sp., *Cruciferae* sp., *Chenopodiaceae* sp., *Cucurbitaceae* sp., *Papilionaceae* sp., such as *Graminae* sp., *Fabacae* sp., as well as genetically modified homologues of these crops.

Preferably, said plant pathogen is selected from the group comprising: fungi, oomycetes, bacteria, viruses, nematodes and insects such as aphids.

The invention also provides for the use of an elicitor comprising: one or more oligo-galacturonan(s) with a degree of polymerization between 9 and 20, and one or more chito-oligosaccharide(s) with a degree of polymerization higher than 5 and a degree of acetylation lower than 50% (preferably with a degree of polymerization between 5 and 10 and a degree of acetylation of about 25%), in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, for enhancing the efficacy of a fungicide.

In a preferred embodiment of said use, the fungicide is selected from the group comprising: phosphonates, benzamides, carbamates, dithiocarbamates, phtalimides, triazoles, quinolines, sulphur, and cyanoimidazoles. More preferably, said fungicide comprises ethylhydrogenphosphonate (fosetyl), preferably fosetyl-Al, fosetyl-Na or fosetyl-K, 2,6-dichloro-N-[3-chloro-5-(trifluoromethyl)-2-pyridinylmethyl]benzamide (fluopicolid), propyl 3-(dimethylamino)propylcarbamate hydrochloride (propamocarb), manganese ethylenebis(dithiocarbamate) (polymeric) complex with zinc salt (mancozeb), N-(trichloromethylthio)phtalimide (folpet), (2RS,3SR)-1-[3-(2-chlorophenyl)-2,3-epoxy-2-(4-fluorophenyl)propyl]-1H-1,2,4-triazole (epoxyconazole), 5,7-dichloro-4-quinolyl 4-fluorophenyl ether (quinoxyfen), sulphur, 4-chloro-2-cyano-N,N-dimethyl-5-(4-methylphenyl)-1H-imidazole-1-sulfonamide (cyazofamid) or a combination thereof.

In a particularly preferred embodiment, said composition additionally comprises an adjuvant such as a surfactant selected from the group comprising: detergents, emulsifiers (alkyl polyglucosides, glycerol ester or polyoxyethylene (20) sorbitan monolaureate), dispersing agents (sodium chloride, potassium chloride, potassium nitrate, calcium chloride or starch of corn), anti-foaming agents (derivates of tartric acid, malic acid or alcohols), penetration enhancers, humectants (ammonium sulfate, glycerin or urea) or wetting agents of ionic or non-ionic type.

Additionally, other co-formulants may be present, such as anti-freeze agents (urea, glycol ethylene, glycol propylene or glycerol), preservative agents (potassium sorbate, paraben and its derivates, 1,2-benzisothiazolin-3(2H)-one or essential oils), absorbent agents (including raids of corn or sawdust), thickeners (including clays or xanthane gum), buffers, sticker agents (including latex, silicon or alkoxylated alkyl), diluents (including rapeseed methyl ester) or a mixture thereof.

In a preferred embodiment, said surfactant comprises one or more of the following components: castor oil ethoxylate, rapeseed methyl ester, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates, lignosulfonates alkoxylated triglycerides, fatty amines polymers, dioctylsulfosuccinates or polyethylene (20) sorbitan monolaureate.

In a preferred embodiment, said fungicide is applied in a concentration which is reduced by at least a factor 2, 3, 4, 5, 6, 7, 8, 9, 10, 15, 25, 40, 50, 60, 70, 80, 90, 100 or 200 when compared to the recommended concentration for said plant and/or conditions.

The invention further provides a method for enhancing the efficacy of a fungicide, comprising adding an elicitor comprising one or more oligo-galacturonan(s) with a degree of polymerization between 9 and 20 and one or more chito-oligosaccharide(s) with a degree of polymerization higher than 5 and a degree of acetylation lower than 50% (preferably with a degree of polymerization between 5 and 10 and a degree of acetylation of about 25%), in varying proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts, to a fungicidal composition.

The invention further provides a composition for protecting plants against (infection by) plant pathogens comprising:

a) an elicitor comprising one or more oligo-galacturonan(s) with a degree of polymerization between 9 and 20 and one or more chito-oligosaccharide(s) with a degree of polymerization higher than 5 and a degree of acetylation lower than 50% in proportions ranging from 1:50 to 50:1, preferably from 1:10 to 10:1, more preferably from 1:5 to 5:1, and b) a surfactant selected from the group comprising: castor oil ethoxylate, rapeseed methyl ester, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyoxyethylene (20) sorbitan monolaurate, preferably wherein said surfactant is C18-castor-oil-ethoxylate (Dehscofix®), organic sulfonate/2-methylpentane-2,4-diol (Tensiofix Dp400), and c) optionally polyoxyethylene (20) sorbitan monolaurate (Tween® 20). The invention also provides for the use of any of said compositions as defined herein in agricultural applications, more particularly for protecting plants against (infection by) plant pathogens preferably against phytopathogenic fungi, oomycetes, bacteria, viruses, nematodes and insects, or for stimulating the plant immune system. The invention further provides a method for protecting plants against (infection by) plant pathogens comprising applying an effective and substantially non-phytotoxic amount of the composition as defined herein to said plants.

Alternatively, the invention provides a composition for protecting plants against (infection by) plant pathogens comprising:

a) an elicitor comprising one or more oligo-galacturonan(s) with a degree of polymerization between 9 and 20 and one or more chito-oligosaccharide(s) with a degree of polymerization higher than 5 and a degree of acetylation lower than 50% in proportions ranging from 1:50 to 50:1, preferably from 1:10 to 10:1, more preferably from 1:5 to 5:1, and b) a second elicitor, preferably a second elicitor comprising sodium silicate, and c) optionally a surfactant, preferably a surfactant comprising polyoxyethylene (20) sorbitan monolaurate. The invention also provides for the use of any of said compositions as defined herein in agricultural applications, more particularly for protecting plants against (infection by) plant pathogens preferably against phytopathogenic fungi, oomycetes, bacteria, viruses, nematodes and insects, or for stimulating the plant immune system. The invention further provides a method for protecting plants against (infection by) plant pathogens comprising applying an effective and substantially non-phytotoxic amount of the composition as defined herein to said plants.

The compositions of the present invention can be provided in a single mixture, or can be a combination of two or more separate mixtures or compositions, which can be applied to the plant or substrate simultaneously, or sequentially. For example, a composition comprising an elicitor and a fungicide according to the present invention can be administered simultaneously, or the elicitor can be applied first, followed by the fungicide, or vice versa.

The present invention will be further exemplified by the following description, drawings and examples, which are not to be seen as limiting. The skilled person will be capable of designing alternative embodiment using the general concept of the present invention. Said alternative concepts also form part of the invention.

DETAILED DESCRIPTION OF THE PREFERRED EMBODIMENTS

Figure 1:
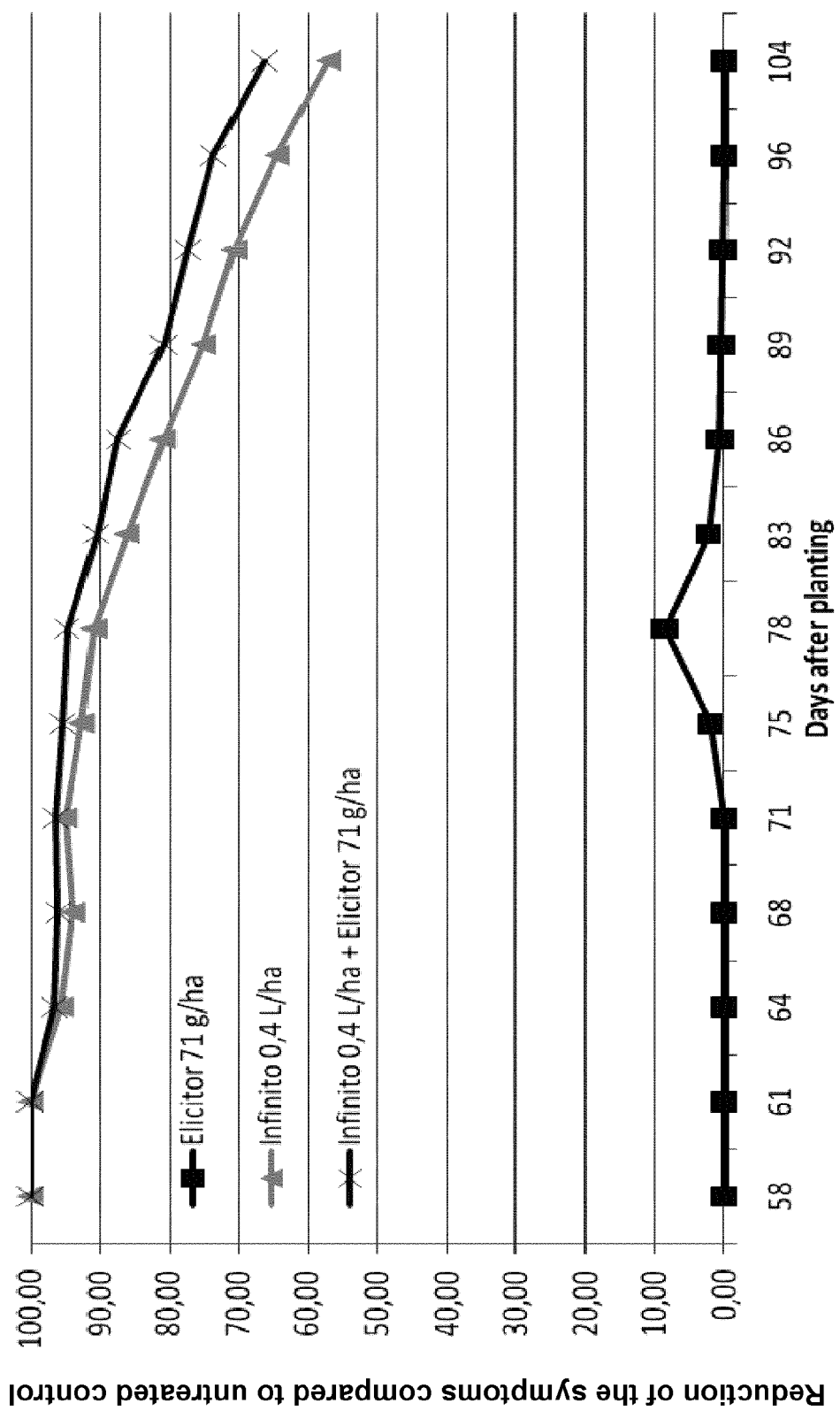
FIG. 1: Protection (expressed as the reduction of the sporulation on the leaves relative to untreated plants) of field grown potato plants against *P. infestans* offered by an elicitor, a fungicide (Infinito) applied at reduced rate (here about one third of the recommended dosage) and a mixture of both. The elicitor alone does not reduce the symptoms, while in combination with the fungicide, the efficacy of the fungicide is clearly improved and especially is maintained longer.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety. In particular, the teachings of all documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. When specific terms are defined in connection with a particular aspect or embodiment, such connotation is meant to apply throughout this specification, i.e., also in the context of other aspects or embodiments, unless otherwise defined.

The present invention advantageously provides a composition which is more active as regards its efficacy against phytopathogenic fungi, oomycetes, bacteria, viruses, nematodes and insects by adding an elicitor of the plant immune system to a fungicide applied at a reduced rate. This enables to apply the fungicide at the reduced rate, which in turn will reduce the amount of fungicidal residues found on plants.

A typical composition according to the invention comprises the following components:

a) an elicitor characterized in that it comprises one or more oligo-galacturonan(s and one or more chito-oligosaccharide(s) in proportions ranging from 1:50 to 50:1, preferably from 1:40 to 40:1, more preferably from 1:30 to 30:1, even more preferably from 1:20 to 20:1, most preferably from 1:10 to 10:1 and for instance is 1:9, 1:8, 1:7, 1:6, 1:5, 1:4, 1:3, 1:2, 1:1, 2:1, 3:1, 4:1, 5:1, 6:1, 7:1, 8:1 or 9:1, and b) a fungicide, wherein said fungicide is preferably selected from the group comprising: phosphonates, benzamides, carbamates, dithiocarbamates, phtalimides, triazoles, quinolines, sulphur, and cyanoimidazoles.

The term "elicitor" as used herein refers to an inducer of the plant immune system. When plants are attacked by pathogens, they defend themselves with an arsenal of mechanisms directed to fight infection or make the plant less attractive to pathogens. As in most cellular responses to the environment, defense mechanisms are activated when receptors directly or indirectly come in contact with pathogens. The ligands of these plant receptors are elicitors of the plant immune system. There is a wide variety of elicitors, including so-called non-specific elicitors or PAMPs (pathogen associated molecular patterns) e.g. degradation products of cell wall components of pathogens or derived from a plant cell wall, and pathogen-specific elicitors or effectors e.g. avirulence gene products of pathogens such as AVR 9 (Avr gene products). Elicitors of the plant immune system comprise proteins, oligosaccharides, polysaccharides, lipids, glycolipids, glycoproteins, peptides of diverse origin, lipopeptides, algal extracts, extracts from the walls of plant material and/or fungal material, fungi, bacterial material and viral material, or yeast material and/or extracts. Elicitors also comprise salicylic acid, jasmonic acid, lipid peroxidation products and/or one or more of their esters. The elicitor preferably used in the present invention is an oligosaccharidic complex of oligo-galacturonans stabilized by chito-oligosaccharides, as e.g. specified in document WO 2008/065151.

The term "oligo-galacturonan" encompasses herein a chain of α-(1-4)-linked D-galacturonic acids. Oligo-galacturonans are derived from pectin, which is a major constituent of plant cell walls. Pectin consists of a complex set of polysaccharides, including homogalacturonans, which are linear chains of α-(1-4)-linked D-galacturonic acids. Oligo-galacturonans are released from these galacturonans through the action of pectolytic enzymes.

The oligo-galacturonans present in the composition according to the invention have a degree of polymerization higher than 8, preferably comprised between 9 and 20 or between 9 and 15.

The terms "chito-oligosaccharide" and "chitosan oligosaccharide" are used interchangeably herein and refer to a linear oligosaccharide composed of randomly distributed β-(1-4)-linked D-glucosamine (deacetylated unit) and N-acetyl-D-glucosamine (acetylated unit). Chitosan is naturally found in few organisms, but is mostly produced industrially by deacetylation of chitin, which is the structural element in the exoskeleton of crustaceans (crabs, shrimp, etc.), insects, and in the cell walls of some fungi and other organisms.

The chito-oligosaccharides used in the composition according to the invention have a degree of acetylation lower than 50%, lower than 40%, or lower than 30%, preferably about 25% and a degree of polymerization higher than 5, preferably comprised between 5 and 10.

In a preferred embodiment, the elicitor used in the compositions according to the present invention comprises:
one or more oligo-galacturonan(s) with a degree of polymerization between 9 and 20, and one or more chito-oligosaccharide(s) with a degree of polymerization higher than 5 and a degree of acetylation lower than 50%, preferably with a degree of polymerization between 5 and 10 and a degree of acetylation of about 25%, in proportions ranging from 1:50 to 50:1, 1:40 to 40:1, 1:30 to 30:1, 1:20 to 20:1, 1:10 to 10:1, 1:5 to 5:1, 1:2 to 2:1, or in equal amounts.

In a preferred embodiment, salts are added to the composition according to the invention to ensure good ionic conditions for the stability of the oligosaccharidic complex, in particular to obtain the so-called "egg-box" conformation of the oligo-galacturonan therein. Preferably, a combination of both monovalent and divalent cation salts is preferably added. Ideally, both calcium and monovalent cations such as sodium are added. The best composition can be determined with the help of the ELISA test with the 2F4 Monoclonal Antibody (cf. Cabrera et al., 2008, Glycobiology 18 (6): 473-482) but also with the help of bioassays that must be optimized for each plant species targeted. Too much calcium displaces chitosan from the complex. Too much monovalent cation displaces calcium from the pectin egg box and can be phytotoxic. A small amount of copper can replace calcium in the egg boxes and is beneficial for the elicitor supramolecular conformation. NaCl is preferably used as monovalent cation salt. $KNO_3$ is also suitable, but less preferred due to possible effect on opening of stomata, possibly enabling entry of parasites into the leaf or plant. $CaCl_2$ is preferably used as divalent cation salt, but $CuCl_2$ or $ZnCl_2$ are also suitable. More preferably, from about 0.2 to 1 mM, most preferably 0.5 mM $CaCl_2$ is used, in combination with from about 5 to 100 mM, most preferably 20 to 50 mM NaCl.

In another preferred embodiment, sucrose is added to the composition according to the invention. Preferably, sucrose is added in a concentration of from about 1 mM to 20 mM, most preferably about 5 to 10 mM sucrose. Sucrose triggers signaling through hexokinase and is also a wetting agent.

In a most preferred embodiment, both salts and sucrose are added to the compositions of the invention.

The term "fungicide" encompasses chemical or biological substances or compositions used to kill or inhibit fungi or oomycetes, e.g. by preventing sporulation, or their spores. Fungicides can exert their biological effect by different modes of action, for example, but not limited to, by interference with nucleic acid synthesis, mitosis and cell division, respiration, amino acids and protein synthesis, signal transduction, lipids and membrane synthesis, sterol biosynthesis, glucan synthesis in the pathogen or by inducing host plant defense.

Any fungicide can be included in the composition of the invention, such as, for example, a fungicide selected from: acylalanines (benalaxyl), anilinopyrimidines (cyprodinil or pyrimethanil), benzamides (fluopicolide or zoxamide), benzimidazoles (fuberidazole, thiabendazole or metrafenone), benzothiadiazoles (acibenzolar-S-methyl), carbamates (benthiavalicarb, iprovalicarb or propamocarb), carboxamides (boscalid), chloronitriles (chlorothalonil), chlorophenyls (tolclophos-methyl), cyanoacetamide oximes (cymoxanil), cyanoimidazoles (cyazofamid), dicarboximides (iprodione), dithiocarbamates (thiram, metiram, mancozeb, manebe or propineb), guanidines (dodine), hydroxyanilides (fenhexamid), imidazoles (fenamidone, imazalil or triflumizole), morpholines (dimethomorph, fenpropimorph, spiroxamine or dodemorph), phosphonates (fosetyl), oxathiins (flutolanil), oxazoles (famoxadone or hymexazol), phenylamides (metalaxyl or metalaxy-M), phenylpyridinamides (fluazinam), phenylpyrroles (fludioxonil), phtalimides (captan or folpet), quinazolinones (proquinazide), quinolins (quinoxyfen), strobilurins (dimoxystrobin, fluoxastrobin, kresomin-methyl, pyraclostrobin, trifloxystrobin or picoxystrobin), thiophenes (silthiofam), triazoles (difenoconazole, epoxyconazole, fenbuconazole, flusilazole, metconazole, myclobutanil, penconazole, propiconazole, tebuconazole, tetraconazole, triadimenol, triticonazole or prothioconazole), copper derivates (copper oxychloride, copper hydrochloride, copper oxide or copper sulphate) and sulphur.

Preferably, the fungicide is chosen from the list comprising: phosphonates, benzamides, carbamates, dithiocarbamates, phtalimides, triazoles, quinolines, sulphur and cyanoimidazoles.

Phosphonates: The mode of action of the phosphonates is largely unknown but could involve inhibition of mitochondrial ATP synthase. Suitable examples of phosphonates are phosphorous acid derivatives, including phosphorous acid itself and its alkali metal or alkaline-earth metal salts. In a preferred embodiment the fungicides are ethyl hydrogenphosphonates such as fosetyl-Al, fosetyl-K and fosetyl-Na. Mention can be made of the phosphonates sold under the trade names Aliette, Autograph, Avalon, Flanker, Legion, Linebacker, Novasource, Prodigy Signature and Quali-Pro, which all comprise fosetyl-Al as active ingredient, and Magellan and Phostrol, which comprise phosphorous acid as active ingredient.

Benzamides interfere with mitosis and cell division. In a preferred embodiment, the benzamides used in the composition of the invention contain 2,6-dichloro-N-[3-chloro-5-(trifluoromethyl)-2-pyridinyl]benzamide (fluopicolide) as active ingredient. Mention can be made of Infinito.

Carbamates act by interfering with lipids and membrane synthesis. In a preferred embodiment, the carbamates used in the composition of the invention contain propamocarb, preferably propamocarb hydrochloride (propyl[3-(dimethylamino)propyl]carbamate hydrochloride) as the active ingredient. Mention can be made of the carbamates sold under the trade names Infinito and Stellar (comprising fluopicolide and propamocarb hydrochloride), Banol, Previcur, Proplant (comprising propamocarb hydrochloride) and Previcur Energy (comprising propamocarb and fosetyl-Al).

Dithiocarbamates show multi-site contact activity. In a preferred embodiment, dithiocarbamates containing manganese ethylenebis(dithiocarbamate) (polymeric) complex with zinc salt (mancozeb) as active ingredient, are used in the composition of the invention. Mention can be made of the dithiocarbamates sold under the trade names Acrobat MZ, Clevis, Cuprofix MZ, Dithane, Evolve, Fore, Gaucho, Gavel, Junction, Mancozide, Manhandle, Manzate, Maxim, Moncoat, Nubark, Penncozeb, Pentathlon, Potato Seed Treater, Protect, Ridomil Gold MZ, SA-50, Stature, Tops MZ, Wingman and Zyban.

Phtalimides also show multi-site contact activity. In a preferred embodiment, the phtalimides used in the elicitor composition of the invention comprise N-(trichloromethylthio)phthalimide or 2-[(trichloromethyl)thio]-1H-isoindole-1,3(2H)-dione (folpet) as active ingredient. Mention can be made of the phtalimides sold under the trade names Folpet and Fungitrol.

Triazoles act by interfering with sterol biosynthesis in membranes. In a preferred embodiment, the triazoles used in the composition of the invention contain (2RS, 3SR)-1-[3-(2-chlorophenyl)-2,3-epoxy-2-(4-fluorophenyl)propyl]-1H-1,2,4-triazole (epoxyconazole) as active ingredient. Mention can be made of the triazole fungicide sold under the trade name Opus.

Cyanoimidazoles act by interfering with the electron transport chain at the level of complex III in the inner membrane of mitochondria, which blocks oxidative phosphorylation powered by electron transfer. In a preferred embodiment, the cyanoimidazoles used in the composition of the invention contain 4-chloro-2-cyano-N,N-dimethyl-5-(4-methylphenyl)-1H-imidazole-1-sulfonamide (cyazofamid) as active ingredient. Mention can be made of the cyanoimidazole sold under the trade name Ranman.

Quinolines act by interfering with, e.g. blocking, signal transduction. In a preferred embodiment, the quinolines used in the composition of the invention contain 5,7-dichloro-4-quinolyl 4-fluorophenyl ether (quinoxyfen) as active ingredient. Mention can be made of the quinoline fungicide sold under the trade names Legend or Quintec.

Sulphur-containing fungicides show multi-site contact activity and contain sulphur as the active ingredient. Mention can be made of the sulphur-containing fungicide sold under the trade name Thiovit®.

The compositions of the invention will typically contain additional components, known as co-formulants or adjuvants, to obtain a product with good handling, efficacy and stability properties. As used herein, the terms "co-formulant" or "adjuvant" designate any substance other than the main oligosacharidic complex elicitor component defined herein, that is intentionally added to the elicitor composition of the invention.

In a preferred embodiment, the composition according to the invention further comprises a co-formulant or adjuvant selected from the group comprising: surfactants, anti-freeze agents (including urea, ethylene glycol, propylene glycol or glycerol), preservative agents (including potassium sorbate, paraben and its derivates, 1,2-benzisothiazolin-3(2H)-one or essential oils), absorbent agents (including raids of corn or sawdust), thickeners (including clays or xanthane gum), buffers, sticker agents (including latex, silicon or alkoxylated alkyl), diluents (including rapeseed methyl ester) or any standard inert ingredient conventionally used in agricultural compositions, or a mixture thereof.

In a particularly preferred embodiment, the composition according to the invention further comprises a surfactant.

With "surfactant" is meant herein a compound that lowers the surface tension of a liquid, allowing easier spreading. The surfactant can be a detergent, an emulsifier (including alkyl polyglucosides glycerol ester or polyoxyethylene (20) sorbitan monolaurate), a dispersing agent (including sodium chloride, potassium chloride, potassium nitrate, calcium chloride or starch of corn), a foaming agent (including derivates of tartric acid, malic acid or alcohols), a penetration enhancer, a humectant (including ammonium sulfate, glycerin or urea) or a wetting agent of ionic or non-ionic type or a mixture of such surfactants. The surfactants used in the present invention are penetration enhancers, dispersing agents or emulsifiers.

The term "penetration enhancer" is understood herein as a compound that accelerates the uptake of active ingredient through the cuticle of a plant into the plant, i.e. the rate of uptake, and/or increases the amount of active ingredient absorbed into the plant. Classes of substances known as penetration enhancers, include alkyl phosphates, such as tributyl phosphate and tripropyl phosphate, and naphthalenesulphonic acid salts. Mention may be made, for example, of surfactants sold under the trade name Dehscofix®, comprising castor oil and ethoxylated fatty acids, such as Dehscofix CO 95 ® (available from Huntsman, USA), comprising C18 ethoxylated fatty acids from castor oil.

With "dispersing agent" is meant a substance added to a suspension, usually a colloid, to improve the separation of particles and to prevent settling or clumping. Mention can be made of the dispersing agent which is sold under the trade name Tensiofix Dp400 (available from Ajinomoto OmniChem), essentially comprising organic sulfonate and 2-methylpentane-2,4-diol.

The term "emulsifier" as used herein refers to a substance that stabilizes an emulsion, i.e. a mixture of two or more liquids. Mention can be made of the emulsifiers sold under the trade names Tween® 20, which essentially comprises polyoxyethylene (20) sorbitan monolaurate (polysorbate 20), and Radia®, which essentially comprises alkyl polyglycosides.

In a preferred embodiment, said surfactant comprises one or more of the following components: castor oil ethoxylate, rapeseed methyl estr, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyoxyethylene (20) sorbitan monolaurate (polysorbate 20), more preferably said surfactant is C18-castor-oil-ethoxylate (Dehscofix®), organic sulfonate/2-methylpentane-2,4-diol (Tensiofix Dp40) or polyoxyethylene (20) sorbitan monolaurate (Tween®20).

The present invention also discloses a composition comprising:
a) an elicitor characterized in that it comprises one or more oligo-galacturonan(s) and one or more chito-oligosaccharide(s) in proportions ranging from 1:50 to 50:1, preferably from 1:40 to 40:1, more preferably from 1:30 to 30:1, even more preferably from 1:20 to 20:1, most preferably from 1:10 to 10:1 and for instance is 1:9, 1:8, 1:7, 1:6, 1:5, 1:4, 1:3, 1:2, 1:1, 2:1, 3:1, 4:1, 5:1, 6:1, 7:1, 8:1 or 9:1, and
b) a co-formulant selected from the group comprising: surfactants, anti-freeze agents (including urea, ethylene glycol, propylene glycol or glycerol), preservative agents (including potassium sorbate, paraben and its derivates, 1,2-benzisothiazolin-3(2H)-one or essential oils), absorbent agents (including raids of corn or sawdust), thickeners (including clays or xanthane gum), buffers, sticker agents (including latex, silicon or alkoxylated alkyl), diluents (including rapeseed methyl ester) or any standard inert ingredient conventionally used in agricultural compositions, or a mixture thereof, preferably said co-formulant is a surfactant selected among a detergent, an emulsifier (including alkyl polyglucosides, glycerol ester or polyoxyethylene (20) sorbitan monolaurate (polysorbate 20)), a dispersing agent (including sodium chloride, potassium chloride, potassium nitrate, calcium chloride or starch of corn), a foaming agent (including derivates of tartric acid, malic acid or alcohols), a penetration enhancer, a humectant (including ammonium sulfate, glycerin or urea) or a wetting agent of ionic or non-ionic type or a mixture thereof, more preferably said surfactant comprises one or more of the following components: castor oil ethoxylate, rapeseed methyl ester, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyoxyethylene (20) sorbitan monolaurate, most preferably said surfactant is C18-castor-oil-ethoxylate (Dehscofix®), organic sulfonate/2-methylpentane-2,4-diol (Tensiofix Dp40) or polyoxyethylene (20) sorbitan monolaurate (Tween®20).

In another embodiment, the compositions according to the invention also comprise one or more other active compounds selected from the group comprising: herbicides, insecticides, plant growth regulators or other plant immune system elicitors.

In a preferred embodiment, said compositions according to the invention further comprises a further plant immune system elicitor chosen among silica, copper, sulfur, aluminium, vanadium, cobalt, nickel, iron, silver, salicylic acid and its derivates (including acetyl-salicylic acid, isonicotinic acid, acibenzolar-5-methyl), jasmonic acid and its derivates (including methyl jasmonate), ethylene and its derivates, polysaccharides (including glucans, xyloglucans, chitin, chitosans, fucans, galactofucans, xylans, galactans, alginates, galacturonans, apiogalacturonans, fructans including inulin, mannans, xylomannans, galactomannans, glucomannans and galactomannans), algae extracts (green algae extracts including ulvans, brown algae extracts including laminarin, and red algae extracts including carragenans), oligosaccharides (including trehalose), peptides (including systemin, 13-pep, flg-22, glutathion), amino acids, proteins (including harpin and flagellin), peptone, beef extract, essential oils (including cumin, anise, mint, cinnamon, thyme, basil, cardamom, coriander, oregano, manzanilla, clove, jojoba and tea tree oils), lipids (including ergosterol, amphotericin, sphingolipids, cerebrosides), glycolipids (including syringolids), glycoproteins (including cryptogeins), lipopeptides, lipoproteins (including volicitin), yeast extracts (including extracts from *Saccharomyces, Candida, Pichia, Aureobasidium* and more particularly *Saccharomyces cerevisiae, Candida famata, Candida oleophila, Pichia guilliermondii, Aureobasidium pullulans*), fungal extracts (including extracts from *Trichoderma, Megasperma, Pyricularia, Alternaria, Pythium, Puccinia, Colletotrichum, Verticillium, Magnaporthe*), bacterial extracts (including extracts from *Escherichia, Rhyzobia, Pseudomonas*), BABA, probenazole, isothianil, phosphorous acid and its derivates (including aluminium, sodium and potassium fosetyl), horsetail extracts, potassium iodide and potassium thiocyanate, *Citrus* extracts, *Yucca* extracts *Salix* extracts and plant decoctions (including nettle decoction).

Preferably, said further plant immune system elicitor contains laminarin (a linear β(1→3)-glucan with β(1→6)-linkages) such as, for example Vacciplant Fruit®.

The present invention also discloses a composition comprising:
a) an elicitor characterized in that it comprises one or more oligo-galacturonan(s) and one or more chito-oligosaccharide(s) in proportions ranging from 1:50 to 50:1, preferably from 1:40 to 40:1, more preferably from 1:30 to 30:1, even more preferably from 1:20 to 20:1, most preferably from 1:10 to 10:1 and for instance is 1:9, 1:8, 1:7, 1:6, 1:5, 1:4, 1:3, 1:2, 1:1, 2:1, 3:1, 4:1, 5:1, 6:1, 7:1, 8:1 or 9:1, and
b) a second elicitor, preferably a second elicitor chosen among silica, copper, sulfur, aluminium, vanadium, cobalt, nickel, iron, silver, salicylic acid and its derivates (including acetyl-salicylic acid, isonicotinic acid, acibenzolar-5-methyl), jasmonic acid and its derivates (including methyl jasmonate), ethylene and its derivates, polysaccharides (including glucans, xyloglucans, chitin, chitosans, fucans, galactofucans, xylans, galactans, alginates, galacturonans, apiogalacturonans, fructans including inulin, mannans, xylomannans, galactomannans, glucomannans and galactomannans), algae extracts (green algae extracts including ulvans, brown algae extracts including laminarin, and red algae extracts including carragenans), oligosaccharides (including trehalose), peptides (including systemin, 13-pep, flg-22, glutathion), amino acids, proteins (including harpin and flagellin), peptone, beef extract, essential oils (including cumin, anise, mint, cinnamon, thyme, basil, cardamom, coriander, oregano, manzanilla, clove, jojoba and tea tree oils), lipids (including ergosterol, amphotericin, sphingolipids, cerebrosides), glycolipids (including syringolids), glycoproteins (including cryptogeins), lipopeptides, lipoproteins (including volicitin), yeast extracts (including extracts from *Saccharomyces, Candida, Pichia, Aureobasidium* and more particularly *Saccharomyces cerevisiae, Candida famata, Candida oleophila, Pichia guilliermondii, Aureobasidium pullulans*), fungal extracts (including extracts from *Trichoderma, Megasperma, Pyricularia, Alternaria, Pythium, Puccinia, Colletotrichum, Verticillium, Magnaporthe*), bacterial extracts (including extracts from *Escherichia, Rhyzobia, Pseudomonas*), BABA, probenazole, isothianil, phosphorous acid and its derivates (including aluminium, sodium and potassium fosetyl), horsetail extracts, potassium iodide and potassium thiocyanate, *Citrus* extracts, *Yucca* extracts *Salix* extracts and plant decoctions (including nettle decoction), more preferably said second elicitor contains β1-3(1-6)glucane (laminarin).

In another preferred embodiment, said compositions according to the invention further comprise a further plant immune system elicitor that contains silicon or silicium (Si), such as, for example, silica ($SiO_2$) or silicates, including sodium silicate ($Na_2SiO_3$). Preferably, said further plant immune system elicitor is a silicate, more preferably sodium silicate.

The present invention also discloses a composition comprising:
  a) an elicitor characterized in that it comprises one or more oligo-galacturonan(s) and one or more chito-oligosaccharide(s) in proportions ranging from 1:50 to 50:1, preferably from 1:40 to 40:1, more preferably from 1:30 to 30:1, even more preferably from 1:20 to 20:1, most preferably from 1:10 to 10:1 and for instance is 1:9, 1:8, 1:7, 1:6, 1:5, 1:4, 1:3, 1:2, 1:1, 2:1, 3:1, 4:1, 5:1, 6:1, 7:1, 8:1 or 9:1, and
  b) a second elicitor, preferably a second elicitor that contains silicon, more preferably said second elicitor is a silicate, even more preferably said second elicitor is sodium silicate.

In a preferred embodiment, said compositions of the invention comprising an elicitor and a second elicitor further comprise an adjuvant, preferably a surfactant, more preferably a surfactant comprising polyoxyethylene (20) sorbitan monolaurate such as Tween® 20.

The compositions according to the present invention encompass not only compositions which are ready to be applied to the plant by means of a suitable device, such as a spraying device, but also the commercial concentrated compositions which have to be diluted before application to the plant.

The compositions according to the invention are themselves in quite diverse, solid or liquid forms. As solid composition forms, mention may be made of powders for dusting and granules, in particular those obtained by extrusion, by compacting, by impregnation of a granulated support or by granulation from a powder, tablets or effervescent lozenges.

As liquid composition forms or forms intended to constitute liquid compositions when applied, mention may be made of solutions, in particular water-soluble concentrates, emulsions, concentrated suspensions, dispersions, aerosols and wettable granules and powders (or powders for spraying), pastes, gels and water soluble packagings.

In another aspect, the present invention relates to the use of the compositions of the invention in agricultural applications, more particularly for protecting plants against (infection by) plant pathogens.

The present invention not only provides in the simultaneous use of the different components of the compositions, i.e. the use of the compositions, but also provides in the sequential use of the different components of the compositions. For instance, the inventors have found that the sequential use of the oligosaccharidic plant immune system elicitor comprising oligo-galacturonans stabilized by chito-oligosaccharides and a fungicide also results in enhanced efficacy of the fungicide. By "sequential use" is meant herein that first the oligosaccharide elicitor is added and subsequently the fungicide, adjuvant, surfactant or other elicitor is applied to the plant, or vice versa.

"Plant pathogens" refer to organisms that cause infectious diseases in plants and include fungi, oomycetes, bacteria, viruses, viroids, virus-like organisms, phytoplasmas, protozoa, nematodes and parasitic plants. In a preferred embodiment, the plant pathogens are fungi, oomycetes, bacteria, viruses, nematodes and insects.

The majority of phytopathogenic fungi belong to the Ascomycetes and the Basidiomycetes, reproducing both sexually and asexually via the production of spores that can be spread through air (wind) or water, or can be soil borne such as zoospores that are capable of living saprotrophically, carrying out the first part of their lifecycle in the soil. Deuteromycetes (Fungi imperfecti) are fungi from which only the asexual form of reproduction is known, meaning that this group of fungus produces their spores asexually. The Oomycetes are not true fungi but are fungal-like organisms that use the same mechanisms as fungi to infect plants.

Fungal and fungal-like organisms are heterotrophic, i.e. they need an external source of nutrients for growth, development and reproduction. An understanding of other key features of these organisms can assist in their identification:
  Hyphae: thread-like strands with a filamentous growth habit are a common feature in most fungi. The hyphae colonize (grow through) substrates so that the organism can obtain nutrients. Plant pathogenic species colonize plants through the host surface, sometimes through direct penetration of intact plant surfaces. Saprophytic fungi tend to penetrate and colonize diseased plant tissue, senescing (dying) plants and plant residues. These fungi are major decomposers of organic matter in soil.
  Hyphal cell walls: true fungi have cell walls composed mainly of glucans and chitin, whereas fungal-like organisms have cell walls composed of cellulose and glycans.
  Septate hyphae: true fungi have cross walls within the hyphae, whereas fungal-like organisms do not. This can aid in the differentiation of these two groups under microscopic examination.
  Motile spores: true fungi do not have motile spores, with the exception of *Chytrids*. Motile zoospores (asexually produced spores) are common in many species in the Oomycota (e.g. *Pythium* and *Phytophthora*) and some downy mildews. Zoospores enable dispersal through water in soil and on plant surfaces.
  Wind dispersed spores: many species of true fungi produce asexual or sexual spores for dispersal in the wind. This is a common feature of foliar fungal pathogens (e.g. *Erysiphe*). However some spores are adapted to splash dispersal.

Survival structures: thick walled spores (e.g. oospores and chlamydospores), sclerotia and multicellular reproductive structures (e.g. pycnidia and perithecia) are important in the disease cycle. During unfavourable environmental conditions or in the absence of a suitable plant host or other substrate, these organisms persist in such specialised survival structures.

Non-limiting examples of phytopathogenic fungi and fungal-like organisms include *Pyricularia oryzae* (*Magnaporthe grisea*) on rice and wheat and other *Pyricularia* spp. on other hosts; *Puccinia* spp. e.g. *Puccinia sorghi, Puccinia graminis* f.sp. *tritici, Puccinia asparagi, Puccinia recondite* or *Puccinia arachidis, Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Erysiphe necator* (*Uncinula necator*) on grape, *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples; *Cochliobolus* spp., *Helminthosporium* spp. (e.g. *Helminthosporium turcicum, Helminthosporium carbonum, Helminthosporium maydis* or *Helminthosporium sigmoideum*), *Drechslera* spp. (*Pyrenophora* spp. e.g. *Pyrenophora tritici-repentens* or *Pyrenophora teres*), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts (e.g. *Septoria lycopersici, Septoria glycines, Septoria*); *Cercospora arachidicola* and *Cercosporidium personatum* on peanuts and other *Cercospora* spp. (e.g. *Cercospora kikuchii* or *Cercospora zaea-maydis*) on other hosts, for example sugar beet, bananas, soya beans and rice; *Botrytis* spp. (e.g. *Botrytis cinerea* or *Botryotinia fuckeliana*), *Botrytis cinerea* (grey mould) on tomatoes, strawberries, vegetables, vines and other hosts and other *Botrytis* spp. on other hosts; *Alternaria* spp. (e.g. *Alternaria brassicola* or *Alternaria solani*) on vegetables (for example carrots), oil-seed rape, apples, tomatoes, potatoes, cereals (for example wheat) and other hosts; *Venturia* spp. (including *Venturia inaequalis* (scab) or *Venturia pirina*) on apples, pears, stone fruit, tree nuts and other hosts; *Cladosporium* spp. (e.g. *Cladosporium fulvum*) on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. (e.g. *Phoma betae* on sugar beet and *Phoma lingam* on oil-seed rape), on turf, rice, potatoes, wheat and other hosts; *Aspergillus* spp. and *Aureobasidium* spp. on wheat, lumber and other hosts; *Ascochyta* spp. (e.g. *Ascochyta pisi*) on peas, wheat, barley and other hosts; *Stemphylium* spp. (*Pleospora* spp.) on apples, pears, onions and other hosts; summer diseases (for example bitter rot (*Glomerela cingulata*), black rot or frogeye leaf spot (*Botryosphaeria obtusa*), Brooks fruit spot (*Mycosphaerellapomi*), Cedar apple rust (*Gymnosporangium juniperi-virginianae*), sooty blotch (*Gloeodespomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. (e.g. *Peronospora manshurica* or *Peronospora tabacina*) on soybeans, tobacco, onions and other hosts, *Pseudoperonospora humuli* on hops and *Pseudoperonospora cubensis* on cucurbits; *Pythium* spp. (including *Pythium ultimum*) on turf and other hosts (e.g. *Pythium aphanidermatum*); *Phytophthora infestans* on potatoes and tomatoes and other *Phytophthora* spp. on vegetables, strawberries, avocado, pepper, ornamentals, tobacco, cocoa and other hosts (e.g. *Phytophthora cinnamomi, Phytophthora cactorum, Phytophthora phaseoli, Phytophthora parasitica, Phytophthora porri, Phytophthora citrophthora, Phytophthora megasperma* f.sp. *soiae* or *Phytophthora infestans*); *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts (e.g. *Sclerotinia sclerotiorum*); *Sclerotium* spp. on turf, peanuts and other hosts; *Gibberella fujikuroi* on rice; *Colletotrichum* spp. (e.g. *Colletotrichum lindemuthianum*) on a range of hosts including turf, coffee and vegetables; *Laetisaria fuciformis* on turf; *Mycosphaerella* spp. on bananas, peanuts, *citrus*, pecans, papaya and other hosts; *Diaporthe* spp. on *citrus*, soybean, melon, pears, lupin and other hosts; *Elsinoe* spp on *citrus*, vines, olives, pecans, roses and other hosts; *Verticillium* spp. (e.g. *Verticillium dahliae* or *Verticillium albo-atrum*) on a range of hosts including hops, potatoes and tomatoes; *Pyrenopeziza* spp. on oil-seed rape and other hosts; *Oncobasidium theobromae* on cocoa causing vascular streak dieback; *Fusarium* spp. (e.g. *Fusarium nivale, Fusarium sporotrichioides, Fusarium oxysporum, Fusarium graminearum, Fusarium germinearum, Fusarium culmorum, Fusarium solani, Fusarium moniliforme* or *Fusarium roseum*), *Typhula* spp., *Microdochium nivale, Ustilago* spp. e.g. *Ustilago maydis* (e.g. corn smut), *Urocystis* spp., *Tilletia* spp. and *Clavicepspurpurea* on a variety of hosts but particularly wheat, barley, turf and maize; *Ramularia* spp. on sugar beet, barley and other hosts; post-harvest diseases particularly of fruit (for example *Penicillium expansum, Penicilliumn digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermiunm seditiosum*) or lumber, notably *Cephaloascusfragrans, Ceratocystis* spp., *Ophiostoma piceae, Penicillium* spp., *Trichoderma pseudokoningii, Trichoderma viride, Trichoderma harzianum, Aspergillus niger, Leptographium liindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania), *Acremoniella* spp., *Allomyces* spp., *Amorphothec* spp., *Aspergillius* spp., *Blastocladiella* spp., *Candida* spp., *Chaetomium* spp., *Coccidioides* spp., *Conidiobolus* spp., *Coprinopsis* spp., *Corynascus* spp., *Cryphonectria* spp., *Cryptococcus* spp., *Cunninghamella* spp., *Curvularia* spp., *Debarymyces* spp., *Diplodia* spp. (e.g. *Diplodia maydis*), *Emericella* ssp., *Encephalitozoon* spp., *Eremothecium* spp., *Gaeumanomyces* spp. (e.g. *Gaeumanomyces graminis* f.sp. *tritici*), *Geomyces* spp., *Gibberella* spp. (e.g. *Gibberella zeae*), *Gloeophyllum* spp., *Glomus* spp., *Hypocrea* spp., *Kluyveromyces* spp., *Lentinula* spp., *Leptosphaeria salvinii, Leucosporidium* spp., *Macrophomina* spp. (e.g. *Macrophomina phaseolina*), *Magnaportha* spp. (e.g. *Magnaporthe oryzae*), *Metharhizium* spp., *Mucor* spp., *Neurospora* spp.,

*Nectria* spp. (e.g. *Nectria heamatococca*), *Paracocidioides* spp., *Phaeopsheria* spp., *Phanerochaete* spp., *Phakopsora* spp. (e.g. *Phakopsora pachyrhizi*), *Phymatotrichum* spp. (e.g. *Phymatotrichum omnivorum*), *Pneumocystis* spp., *Pyronema* spp., *Rhincosporium secalis, Rhizoctonia* spp. (e.g. *Rhizoctonia solani, Rhizoctonia oryzae* or *Rhizoctonia cerealis*), *Rhizopus* spp. (e.g. *Rhizopus chinensid*), *Saccharomyces* spp., *Scerotium* spp. (e.g. *Scerotium rolfsii*), *Spizellomyces* spp., *Thermomyces* spp., *Thielaviopsis* spp. (e.g. *Thielaviopsis basicola*), *Trametes* spp., *Trichophyton* spp., or *Yarrwia* spp.

Plant diseases caused by fungi including yeasts, rusts, smuts, mildews, molds, mushrooms and toadstools that can be treated using the elicitor compositions according to the present invention are for example:

"Rust" is a fugal diseases in plants, which produces reddish-brown discoloration of the stems and leaves.

"Black Rot" is characterized by the darkening and decaying of leaves of fruit and vegetable plants.

"Black Spot" is one of the many fungal diseases in plants. It is named "black spot" because it produces small black spots on plants.

"Bottom Rot" is a fungal disease found on lettuce plants. The characteristic of this fungus is that it first affects the leaves on the lower part of the plant and then moves upward to affect the upper part.

"Canker" affects the roots and bark, is found on woody trees and is notorious for causing localized damage to the bark of trees.

"Cotton Ball" is notorious for attacking cranberry plants.

"Crown Wart" like canker attacks on the barks of woody trees, this fungus attacks the stem of the alfalfa plants. It forms white protrusions at the base of the stem of the plant.

"Potato Wart" is a fungal disease that causes dark, warty, spongy excrescences in the eyes of potato tubers, similar to the crown wart in alfalfa plants.

"Damping Off" causes excessive moisture conditions of the seedlings.

"Dry Rot" causes the drying and crumbling of timber, bulbs, potatoes or fruits.

"Rhizoctinia Disease" is caused by fungi called *Pellicularia* and *Corticium*. It is often seen to affect small potatoes.

"Root Rot" infects the roots causing root decay, eventually causing the plant to die.

"*Sclerotium* Rot" is caused by Fungus of the genus *Sclerotium* causing the formation of sclerotia on plants.

"Dutch Elm Disease" is a fungal disease affecting Elms. It spreads from one plant to another through root grafts or by the elm beetles that feed on small twigs.

"Pinkroot" attacks onion plants and makes them unsuitable for consumption.

"Soft Rot" is a slimy, mushy decay caused by fungi.

"Yellow Spot" is characterized by a yellow spotting on the leaves of plants.

"Powdery Mildews" is often specific to the host that it invades. It is normally seen on roses, lilac, English oak, zinnias, etc.

"Plant Wilting" gets it name because it causes the plant it infects to wilt. The fungus invasion starts in the roots and then slowly makes its way into the stem and plugs the vascular system of the plant.

"Decay" is decomposition of wood that is caused by fungi. When it attacks living plant tissue, it kills the plants.

Non-limiting examples of phytopathogenic bacteria include the genii *Erwinia* (including *Erwinia amylovora*, causing fire blight on pears), *Pseudomonas* (including *Pseudomonas syringae*), *Xanthomonas* (including *Xanthomonas orizae, Xanthomonas citri, Xanthomonas fuscans* (citrus cancer) and *Xanthomonas fragariae*) and *Ralstonia*.

Non-limiting examples of phytopathogenic viruses include Cucumber Mosaic Virus, Barley Yellow Mosaic Virus, Strawberry Mild Yellow Edge Virus, Strawberry Latent Ringspot Virus, Beet Necrotic Yellow Vein Virus and Potato Virus Y.

Phytopathogenic insects that can be targeted by application of the compositions according to the invention include aphids, beetles, bugs, hoppers, locusts, mites, ants, ticks, trips, whiteflies, rootworms, maggots, weevils, (stem)borers, caterpillars, butterflies, leaf-rolers, leaf-miners, etc.

"Plant protection" as used herein refers to the activation of mechanisms aimed at controlling or reducing the pathogens and/or to minimize their effects on the plant. Plant protection can be achieved by killing the pathogens, by delaying their growth and/or reproduction, by reducing sporulation, etc.

According to another aspect of the present invention, there is provided a method for protecting plants against (infection by) plant pathogens, characterized in that an effective and substantially non-phytotoxic amount of a composition according to the invention is applied to the plants. The expression "effective and non-phytotoxic amount" means an amount of elicitor composition according to the invention that is sufficient to induce control or destruction of the plant pathogens present or liable to appear on the plants, and that does not entail any appreciable symptom of phytotoxicity for said plants. Such an amount can vary within a wide range depending on the plant pathogen to be controlled, the type of plant, the climatic conditions and the compounds included in the composition according to the invention. This amount can be determined by systematic field trials that are within the capabilities of a person skilled in the art.

In a particularly preferred embodiment, the fungicide in the composition of the invention is applied at a reduced rate. Preferably, the rate of the fungicide is reduced by at least a factor 2, 3, 4, 5, 6, 7, 8, 9, 10, 15, 25, 40, 50, 60, 70, 80, 90, or 100 when compared to the recommended rate, or is reduced by 10, 20, 30, 40, 50, 60, 70, 80, 90, or even 95% or more of the recommended dosage for said plant and/or conditions. More preferably, the rate of the fungicide is reduced by 50% to 90%, 60% to 90%, 70% to 90%, 80% to 90%, 60% to 80%, or 60% to 70% of the recommended rate for said plant and/or conditions.

Application of the composition according to the invention can be carried out in accordance with techniques well known to persons skilled in the art. The composition according to the invention can be applied to the whole plant, or to leaves, flowers, fruits, seeds and/or roots of the plant, as well as to the soil or inert substrate wherein the plant is growing or in which it is desired to grow (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane), organic substrates (e.g. peat, composts, tree waste products like coir, wood fibre or chips, tree bark) or to a liquid substrate (e.g. floating hydroponic systems, Nutrient Film Technique, Aeroponics). The application can be done by spraying, drenching, soaking, dipping, injection, etc., or via fertigation systems.

It can also be useful to apply the compositions according to the invention to propagation material such as tubers or rhizomes, but also seeds, seedlings or seedlings pricking out and plants or plants pricking out. The compositions according to the invention can also be applied post-harvest to control decay.

Among the plants that can be protected by the method according to the invention, mention can be made of cotton;

flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Vitaceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Brassicaceae* sp. (for instance rapeseed and colza), *Fabacae* sp. (for instance peanuts), *Papilionaceae* sp. (for instance soybean), *Solanaceae* sp. (for instance tomatoes and potatoes), *Chenopodiaceae* sp. (for instance beetroots); horticultural and forest crops; as well as genetically modified homologues of these crops.

The invention is further exemplified by the following non-limiting examples.

EXAMPLES

Example 1

Comparison of the Efficacy of a Fungicide Applied Alone or in Mixture with an Elicitor in Controlling *Phytophthora infestans* on Potato (Field Trial)

Potato plants (*Solanum tuberosum*) of the *Phytophthora infestans* sensitive variety *Bintje* were field grown near Gembloux, Belgium.

28 days after planting, the first application of the treatments was performed. The treatments were applied 10 times at 7 days interval between applications. The plants were treated by spraying 0.4 L of a test solution per hectare. The test solutions were composed of elicitor alone, fungicide alone or a mixture of both. The active ingredient in the elicitor was an oligosaccharidic complex consisting of negatively charged oligo-galacturonans stabilized by positively charged chito-oligosaccharides. The elicitor was provided as a powder comprising 70.4% active ingredient and was applied at 50 g active ingredient/ha (71 g powder). The fungicide used was Infinito (Bayer, Germany), which was chosen for its high level of protection of potato against *P. infestans*. Infinito comprises the active ingredients propamocarb and fluopicolid at 625 g/l and 62.5 g/L, respectively. The fungicide was applied at 0.4 L/ha, which is one third of the recommended rate. The summary of the test solutions is detailed in Table 1.

TABLE 1

Compositions of test solutions applied on potato against *P. infestans*.

| Test solution | Rate | Rate Unit | Active ingredients (g/ha) |
|---|---|---|---|
| fungicide (Infinito) | 0.4 | L/ha | propamocarb (250) + fluopicolid (25) |
| elicitor | 71 | g/ha | oligosaccharidic complex (50) |
| fungicide (Infinito) + elicitor | 0.4<br>71 | L/ha<br>g/ha | propamocarb (250) + fluopicolid (25)<br>oligosaccharidic complex (50) |

The percentage of sporulation on leaves (sporulation area compared to leaf area) was evaluated every 3-4 days from the appearance of the disease in the untreated plants (58 days after planting), and during 46 days, thus, until 104 days after planting. These values were transformed into protection values by a comparison of the symptoms with the untreated plants.

FIG. 1 shows the effects of the applied test solutions on the protection of potato plants against *P. infestans* as the reduction of the symptoms compared to untreated plants.

During the whole experiment, the elicitor applied alone did not offer any protection of potato plants against *P. infestans* compared to untreated plants.

The fungicide applied alone offered a total protection during the first two observations. After that a reduction of the protection—from 100 to 95%—was observed between days 61 and 71 after planting. A steeper decrease was then noted between days 71 and 104 after planting. At the end of the experiment, the protection fell down to 57%.

With the mixture of the fungicide and the elicitor, a total protection was also observed during the first two observations. After that the protection reached 95% and this plateau was maintained until day 78 after planting, which represents the same level of protection as that offered by the fungicide alone one week before. The level of 75% of protection was reached at day 89 after planting for the fungicide alone while this threshold was only reached at day 96 when mixed with the elicitor. This delay of one week corresponds to two *P. infestans* developmental cycles. It is therefore possible to delay the infection thanks to the addition of the elicitor to the fungicide. At the end of the experiment, the protection offered by the mixture corresponded to 66.2%, which represents a 16% increase of the protection compared to the fungicide alone. This is unexpected, since application of the elicitor alone didn't have any effect on the infection of the potato plants by *P. infestans*.

Example 2

Comparison of the Efficacy of a Fungicide Applied Alone or in Mixture with an Elicitor in Controlling *Plasmopara viticola* (Downy Mildew) on Grape (Greenhouse Trial)

Grape seedlings of the variety Marselan were grown under controlled conditions in a greenhouse.

The seedlings were treated by spraying a test solution on both faces of the leaves. The test solutions were composed of elicitor alone, fungicide alone or a mixture of both. The active ingredient in the elicitor was an oligosaccharidic complex consisting of negatively charged oligo-galacturonans stabilized by positively charged chito-oligosaccharides. The elicitor was provided as a concentrated solution, which was diluted in order to obtain a test solution comprising 20 mg active ingredient/L. The fungicide used was Aliette (Bayer, Germany), which was chosen for its high level of protection of grape against *P. viticola*, despite the absence of registration on this crop. Aliette was provided as a powder comprising 80% of its active ingredient fosetyl. Aliette was applied at 1.73 g/L, which is about one fourth of the recommended rate applied on apple against *Erwinia amylovora*. The summary of the test solutions is detailed in Table 2.

TABLE 2

Compositions of test solutions applied on grape against P. viticola.

| Test solution | Rate | Rate Unit | Active ingredients (mg/L) |
|---|---|---|---|
| fungicide (Aliette) | 1730 | mg/L | fosetyl (1380) |
| elicitor | 20 | mg/L | oligosaccharidic complex (20) |
| fungicide (Aliette) | 1730 | mg/L | fosetyl (1380) |
| + elicitor | 20 | mg/L | oligosaccharidic complex (20) |

The treatments were applied 3 days before the seedlings were artificially inoculated (by brumisation).

After inoculation, the seedlings were incubated in a chamber with high degree of humidity for 6 days after inoculation.

The percentage of sporulation on leaves (sporulation area compared to leaf area) was evaluated 7 days after inoculation. These values were transformed into protection values by a comparison of the symptoms with the untreated seedlings.

Figure 2:
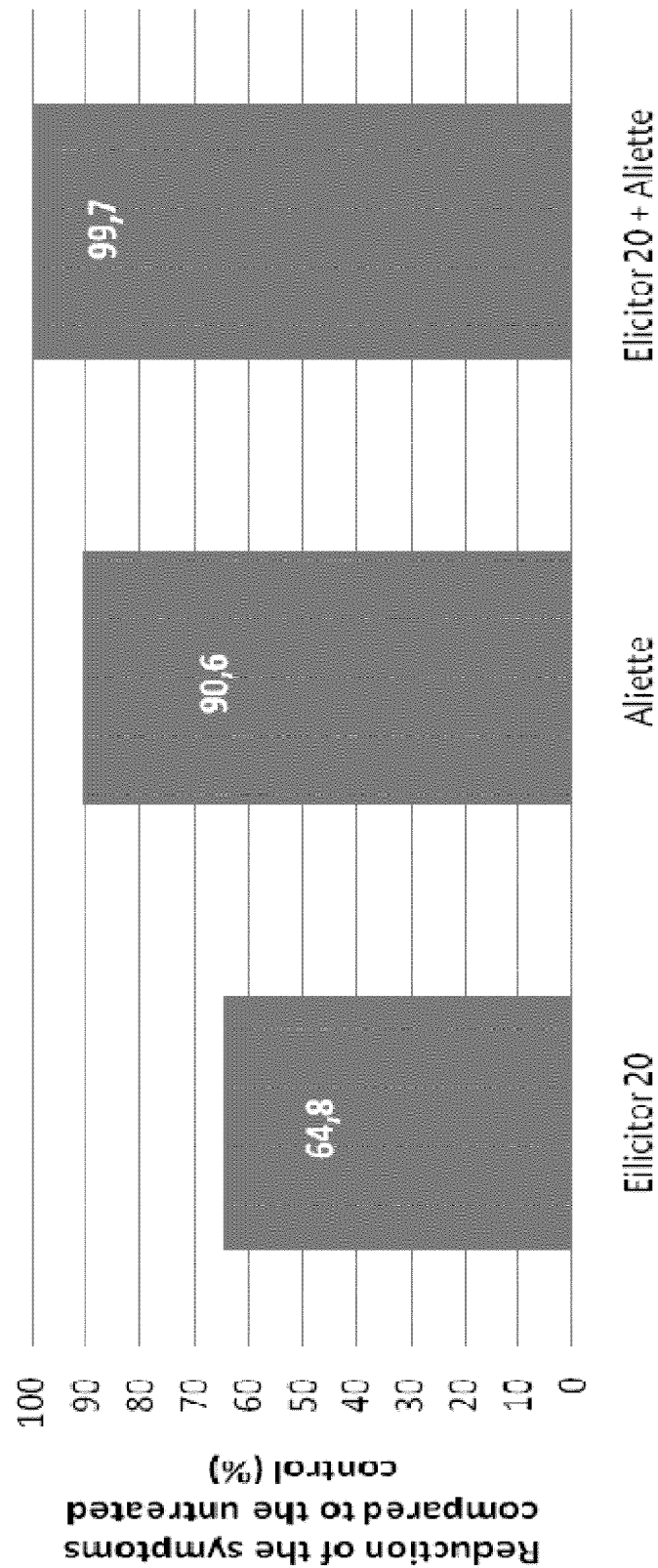
FIG. 2: Protection (expressed as the reduction of the sporulation on the leaves relative to untreated seedlings) of grape seedlings against *P. viticola* offered by an elicitor, a fungicide (Aliette) applied at reduced rate (about one fourth of the recommended dose) and a mixture of both. The combination of the elicitor and the fungicide leads to an almost complete reduction of the symptoms, even when the fungicide is applied at one fourth of the recommended dose.

FIG. 2 shows the effects of the applied test solutions on the protection of grape seedlings against P. viticola as the reduction of the symptoms compared to untreated plants.

The elicitor applied alone offered a 64.8% protection against P. viticola on grape seedlings. The protection offered by the fungicide alone was higher (90.6%) but not total. Once in mixture, these two compounds offered a total protection (99.7%) against P. viticola.

Example 3

Comparison of the Efficacy of a Fungicide Applied Alone or in Mixture with an Elicitor in Controlling *Phytophthora infestans* on Potato (Greenhouse Trial)

Certified healthy microtubers of potato (*Solanum tuberosum*) of the *Phytophthora infestans* sensitive variety Bintje were grown on compost in individual containers under controlled conditions in a greenhouse (24° C., 16 h day/8 h night regime) for 6 weeks. 6 weeks after planting, the 3 last leaves of each plant were labeled just before the first treatment, ensuring to have leaves of the same physiological age for further inoculation.

The first application of the treatments was performed 6 weeks after planting and 7 days before planned inoculation. A second application was made 3 days before inoculation. The treatments were applied by spraying 50 mL of a test solution on the whole plant and on both leaves faces. 8 plants were selected for each test solution to assess. The summary of the test solutions is detailed in Table 3.

TABLE 3

Compositions of test solutions applied on potato against P. infestans.

| Test solution | Rate | Rate Unit | Active ingredients (mg/L) |
|---|---|---|---|
| adjuvant (Dehscofix CO 95) (control) | 0.1% | v/v | — |
| fungicide (Aliette) | 800 | mg/L | fosetyl-Al (640) |
| elicitor | 50 | mg/L | oligosaccharidic complex (50) |
| + adjuvant (Dehscofix CO 95) | 0.1% | v/v | — |
| fungicide (Aliette) | 800 | mg/L | fosetyl-Al (640) |
| + elicitor | 50 | mg/L | oligosaccharidic complex (50) |
| + adjuvant (Dehscofix CO 95) | 0.1% | v/v | — |

The elicitor was applied as a formulation with the adjuvant Dehscofix CO 95 (Huntsman, Belgium). The active ingredient in the elicitor was an oligosaccharidic complex consisting of oligo-galacturonans (with degrees of polymerization between 9 and 20) and chito-oligosaccharides (with degrees of polymerization between 5 and 10 and with a degree of acetylation around 25%) in equal proportions. The elicitor further contained the salts $CaCl_2$ (0.5 mM) and NaCl (50 mM) to ensure good ionic conditions for the stability of the oligosaccharidic complex. The elicitor was applied at 50 mg active ingredient/L. The fungicide used was Aliette, which was chosen for its favorable ecotoxicological profile and versatile plant protection effect against oomycetes. Aliette was provided as a powder comprising 80% of its active ingredient fosetyl-Al. Aliette was applied at 800 mg/L, which is about one tenth of the recommended rate. Control plants were sprayed with Dehscofix CO 95, the adjuvant used in the elicitor formulation.

3 days after the second treatment, the 3 labeled leaves of each plant were collected in individual transparent plastic boxes on filter paper with a small amount of water. P. infestans inoculum was collected from potato leaves and spore concentration was adjusted to $10^4$ spores/mL prior to inoculation. 2 droplets of 10 µL were put on five leaflets of the potato leaves yielding 10 inoculation points per leaf for further assessments. All the boxes containing the leaves were incubated in a growth cabinet at 90% relative humidity and 24° C. with a 16 h day/8 h night regime.

6 and 8 days after inoculation, the leaves were evaluated for disease occurrence, sporulation occurrence and sporulation area.

Disease occurrence and sporulation occurrence are evaluated by first attributing a score, corresponding to the stage of the observed lesion, to each inoculation point.

0: no symptoms
1: light necrosis located under the inoculation droplet, which may be a hypersensitive reaction
2: spreading lesion under the form of extensive necrosis located under and around the inoculation droplet
3: slight sporulation
4: important sporulation Disease occurrence is then calculated for each leaf as the number of observed scores equal or higher than 2 divided by the number of inoculation points. It yields a value comprised between 0 and 1. The value 0 of disease occurrence is considered for a leaf as no disease development for all the inoculation points and the value 1 as a disease development on all inoculation points.

Sporulation occurrence is calculated for each leaf as the number of observed scores equal or higher than 3 divided by the number of inoculation points. It yields also a value comprised between 0 and 1. The value 0 of sporulation occurrence is considered for a leaf as no late blight's sporulation for all the inoculation points and the value 1 as presence of late blight's sporulation on all inoculation points.

Sporulation area is a visual estimate of the leaf surface under sporulation expressed.

Figure 3:
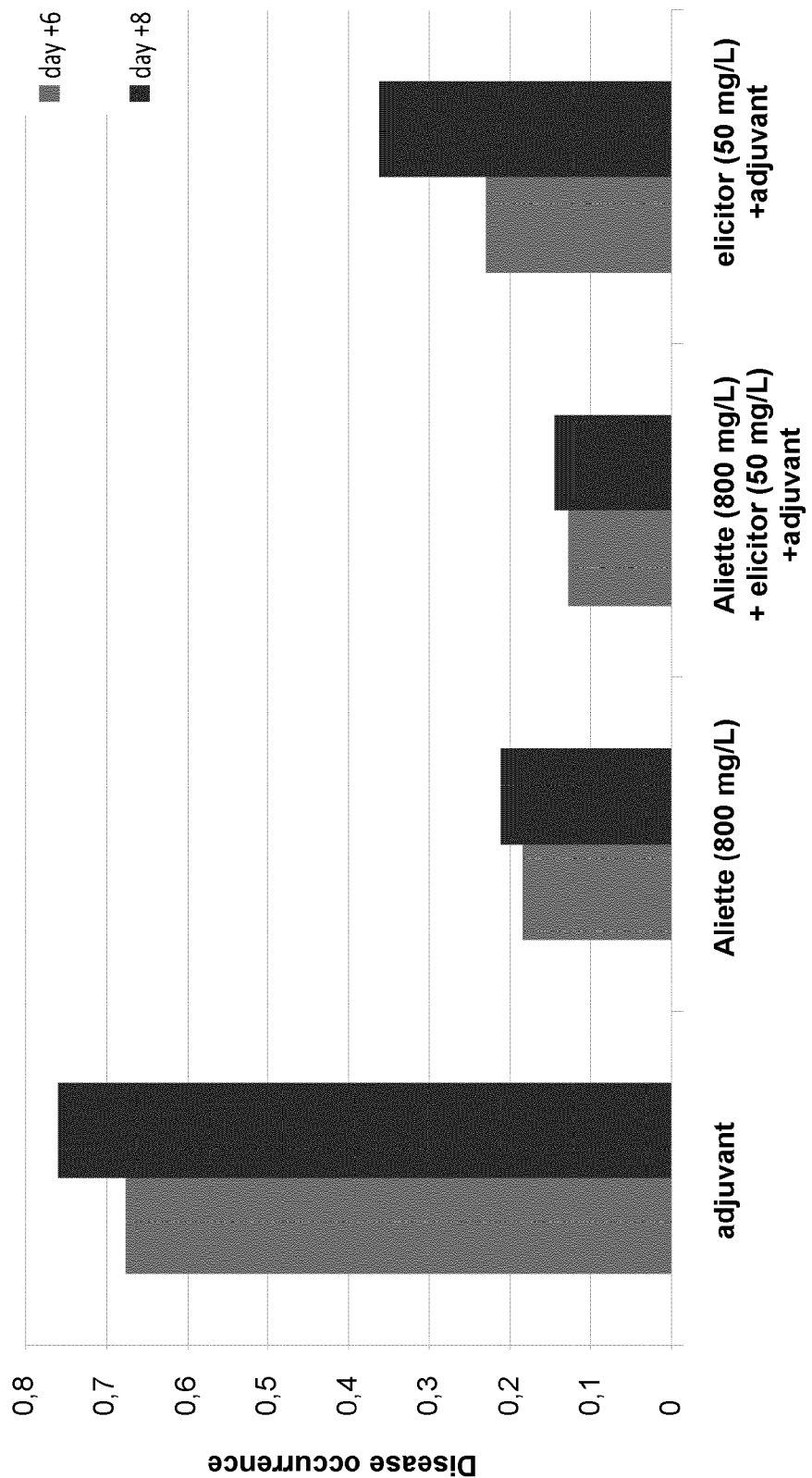
FIG. 3: Mean of disease occurrence on detached leaves of *Solanum tuberosum* (var. *Bintje*) after 2 treatments with elicitor, fungicide (Aliette) applied at reduced rate (about one tenth of recommended dose) or a combination of both, 6 and 8 days after inoculation with *P. infestans* at $10^4$ spores/mL.
Figure 4:
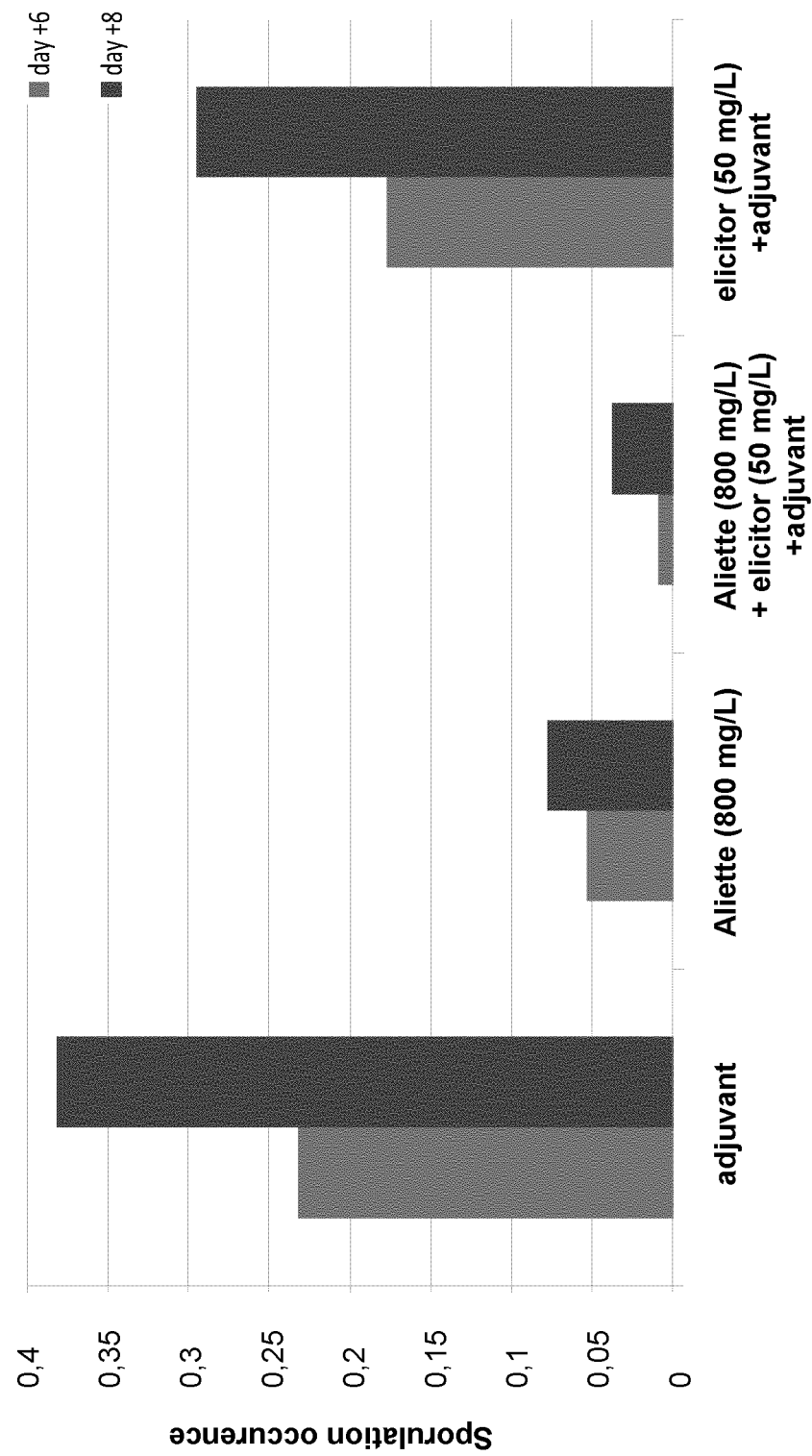
FIG. 4: Mean of sporulation occurrence on detached leaves of *Solanum tuberosum* (var. *Bintje*) after 2 treatments with elicitor, fungicide (Aliette) applied at reduced rate (about one tenth of recommended dose) or a combination of both, 6 and 8 days after inoculation with *P. infestans* at $10^4$ spores/mL.
Figure 5:
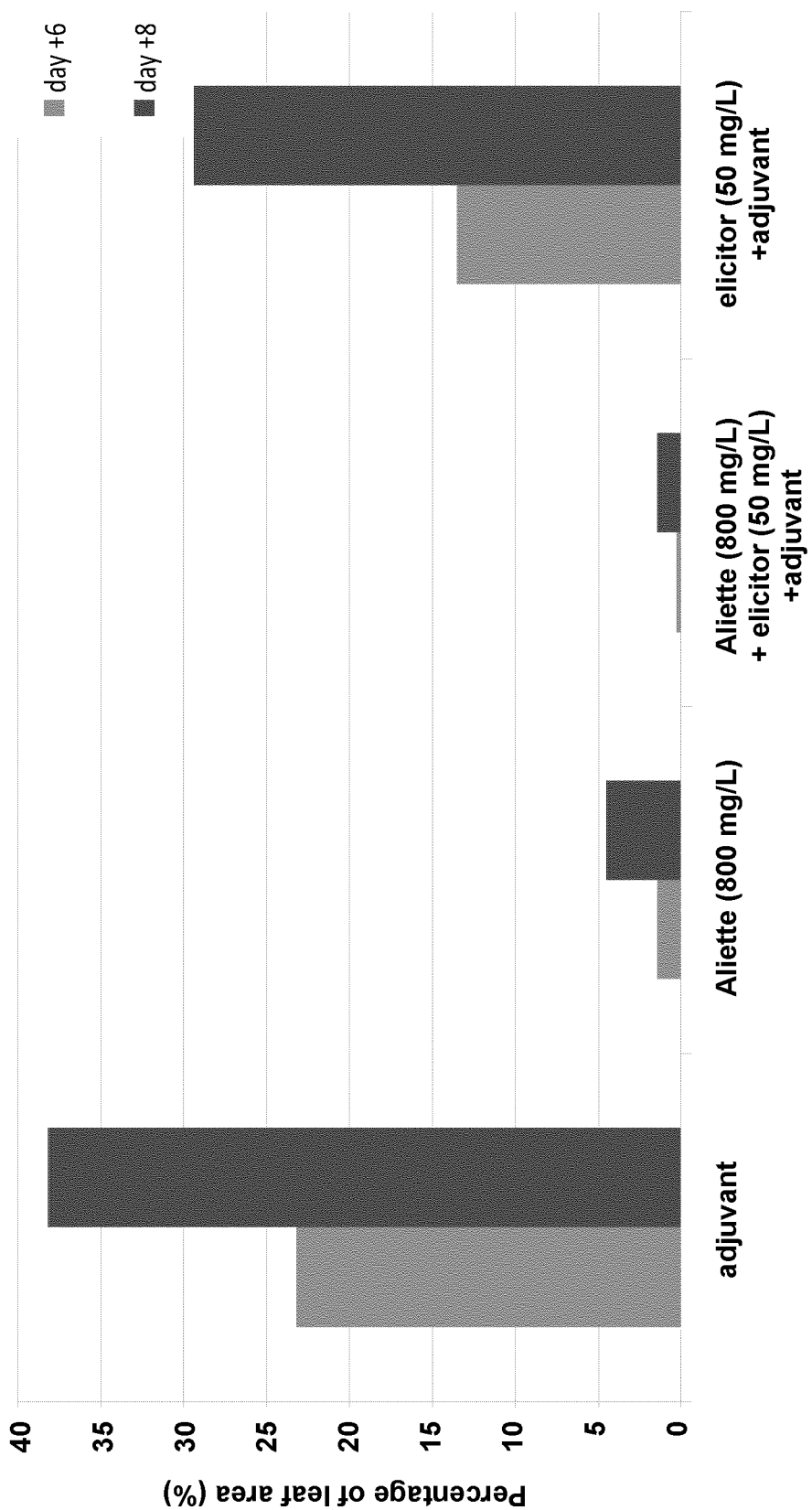
FIG. 5: Percentage of leaf area under sporulation on detached leaves of *Solanum tuberosum* (var. *Bintje*) after 2 treatments with elicitor, fungicide (Aliette) applied at reduced rate (about one tenth of recommended dose) or a combination of both, 6 and 8 days after inoculation with *P. infestans* at $10^4$ spores/mL.

FIG. 3 represents the mean of disease occurrence, FIG. 4 the mean of sporulation occurrence and FIG. 5 the percentage of leaf area under sporulation.

The fungicide Aliette, applied at a rate 10 times lower than recommended, confers partial protection. This protection is especially marked on sporulation occurrence and percentage sporulation. The elicitor also reduces disease occurrence and sporulation, but the reduction of the symptoms conferred by the fungicide is higher than the one obtained after elicitor application. More interesting, these data highlight the fact that the symptoms reduction of the mixture of fungicide and elicitor is higher than the one of the two test compounds alone. Thus, the addition of the elicitor to a low rate of the fungicide improves the control of disease development.

Example 4

Comparison of the Efficacy of a Fungicide Applied Alone or in Mixture with an Elicitor in Controlling *Septoria tritici* (*Mycosphaerella graminicola*) in Winter Wheat (Field Trial)

Winter wheat of the *Septoria tritici* very sensitive variety Istabraq were field grown near Namur, Belgium.

The plants were treated with either fungicide alone, elicitor alone or a combination of both. The fungicide used was Opus (BASF, Germany), which was chosen for its high level of protection of winter wheat against *S. tritici*. Opus comprises the active ingredient epoxyconazole at 125 g/L. The fungicide was applied at 0.25 L/ha, which is one fourth of the recommended rate. The fungicide was applied alone at stages 32 (second node detectable) and 55 (emergence of inflorescence at 50%).

The active ingredient in the elicitor was an oligosaccharidic complex consisting of negatively charged oligo-galacturonans stabilized by positively charged chito-oligosaccharides. The elicitor was provided as a concentrated solution comprising 10 g/L of active ingredient and was applied alone at 1 L/ha alone at stages 30 (ear at 1 cm), 32 (second node detectable), 39 (flag leaf ligule just visible) and 55 (emergence of inflorescence at 50%).

The fungicide and the elicitor were also applied in combination as a program: the fungicide was applied at stages 32 and 55 whereas the elicitor was applied at stages 30, 32, 39 and 55. The treatments are summarized in Table 4.

TABLE 4

Treatments applied on winter wheat against *S. tritici*.

| Test solution | Stage | Rate | Rate Unit | Active ingredients (g/ha) |
|---|---|---|---|---|
| fungicide (Opus) | 32, 55 | 0.25 | L/ha | epoxyconazole (31.25) |
| elicitor | 30, 32, 39, 55 | 1 | L/ha | oligosaccharidic complex (10) |
| fungicide (Opus) + elicitor | 32,55 | 0.25 | L/ha | epoxyconazole (31.25) |
| | 30, 32, 39, 55 | 1 | L/ha | oligosaccharidic complex (10) |

Assessments of leaf diseases were made on 15 plants randomly selected in each plot from four replicates. The percentage of leaf area (pest severity) colonized by the disease was visually assessed on the different leaf layers. The percentages of leaves with symptoms of the disease were also calculated (pest incidence).

Synergistic effects were assessed by applying the method defined by Colby (1967, "Calculation of the synergistic and antagonistic responses of herbicide combinations", Weeds, 15, pages 20-22) using the following formula, which is also referred to as the Colby formula:

$$E = X + Y - \frac{XY}{100}$$

wherein E represents the expected percentage of inhibition of the pest for the combination of the two compounds at defined doses, X is the percentage of inhibition observed for the pest by compound (A) at a defined dose, Y is the percentage of inhibition observed for the pest by compound (B) at a defined dose. When the percentage of inhibition observed for the combination is greater than E, there is a synergistic effect.

Figure 6:
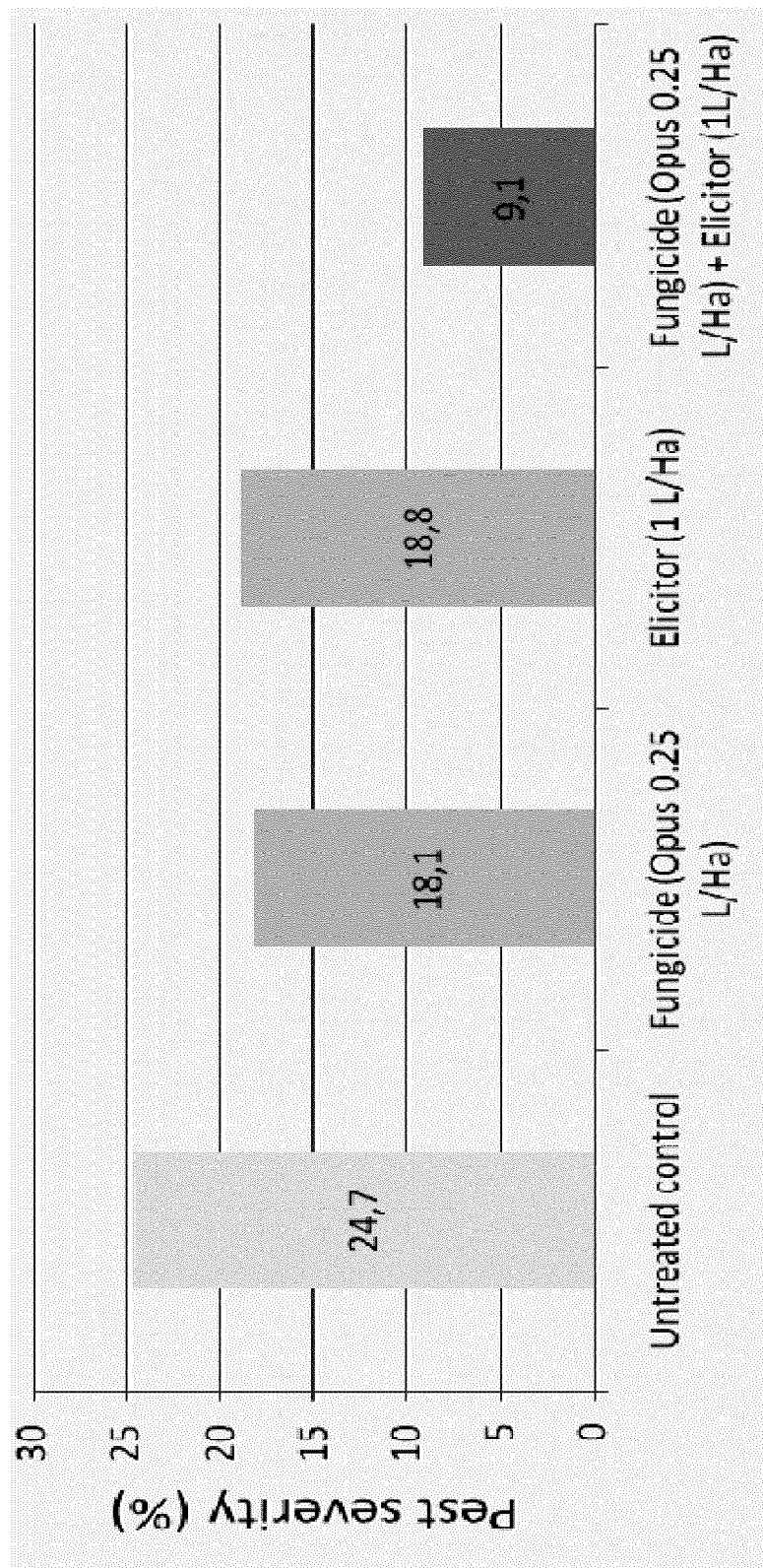
FIG. 6: Pest severity (expressed as the percentage of leaf area colonized by the disease) caused by *Septoria tritici* on winter wheat following treatment with fungicide (Opus) applied at reduced rate (about one fourth), elicitor or a combination of both.

FIG. 6 shows the effects of the applied treatments on the severity of the disease caused by *S. tritici* on winter wheat.

The percentages of pest severity with the two compounds alone were 18.1 (for the fungicide) and 18.8 (for the elicitor), whereas the same parameter was assessed at 24.7% for the untreated control. The reduction of the severity compared to the untreated control corresponds to 26.8 and 23.9% in presence of the fungicide and the elicitor, respectively. Once in combination these two treatments present a percentage of severity of 9.1%, which corresponds to a reduction of the symptoms of 63.1% compared to the untreated control. The Colby analysis demonstrates a synergistic effect concerning pest severity between the fungicide and the elicitor. The observed percentage of protection (63.1%) is greater than the expected percentage of protection E (44.3%), wherein E was calculated as:

$$E = 26.8 + 23.9 - \frac{26.8 \times 23.9}{100} = 44.3\%$$

Figure 7:
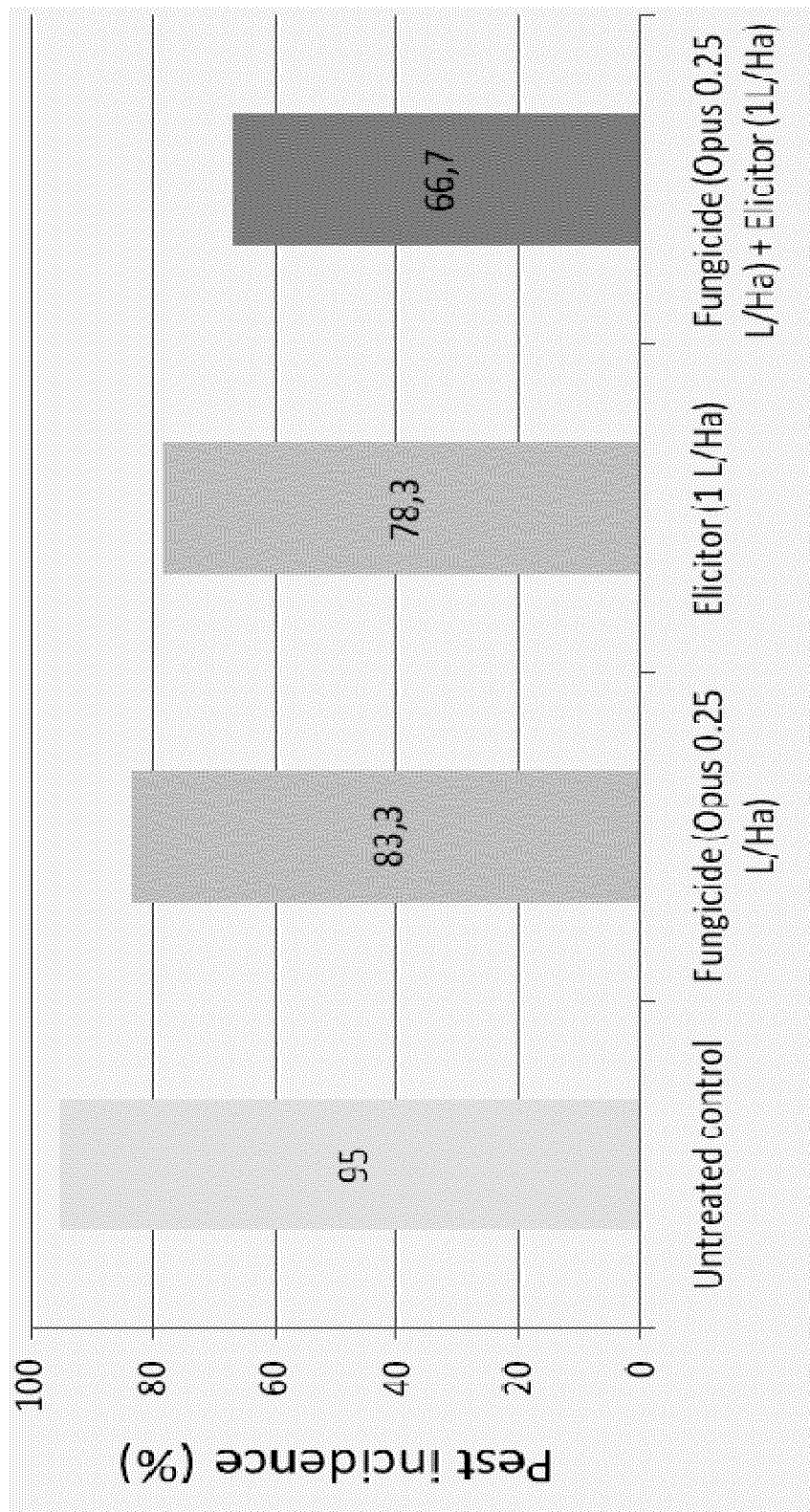
FIG. 7: Pest incidence (expressed as the percentage of leaves with symptoms of the disease) caused by *Septoria tritici* on winter wheat following treatment with fungicide (Opus) applied at reduced rate (about one fourth), elicitor or a combination of both.

FIG. 7 shows the effects of the applied treatments on the incidence of the disease caused by *S. tritici* on winter wheat.

The percentages of pest incidence with the two compounds alone were 83.3 (for the fungicide) and 78.3% (for the elicitor), whereas the same parameter was assessed at 95.0% for the untreated control. The reduction of the incidence compared to the untreated control corresponds to 12.3 and 17.5% in presence of the fungicide and the elicitor, respectively. Once in combination these two treatments present a percentage of incidence of 66.7%, which corresponds to a reduction of the symptoms of 29.8% compared to the untreated control.

The Colby analysis also demonstrates a synergistic effect concerning pest incidence between the fungicide and the elicitor. The observed percentage of protection (29.8%) is greater than the expected percentage of protection E (27.6%), wherein E was calculated as:

$$E = 12.3 + 17.5 - \frac{12.3 \times 17.5}{100} = 27.6\%$$

Example 5

Comparison of Peroxidase Activity of Tomato Treated with an Elicitor Alone, a Fungicide Alone or a Mixture of Both (Greenhouse Trial)

Tomato plants (*Lycopersicon esculentum*, variety *Saint Pierre*) were grown under controlled conditions in a greenhouse (24° C., 16 h day/8 h night regime) for 4 weeks. 1 day before treatment, 4 weeks old plants were placed in a growth cabinet (Weiss) at 18° C. with a 16 h/8 h day/night regime and 90% relative humidity. The plants were watered 2 h before treatment. For each treatment, 12 tomato plants were sprayed with 200 mL of a test solution on both sides of the leaves until run off. The composition of the test solutions is detailed in Table 5.

TABLE 5

Compositions of test solutions applied on tomato.

| Test solution | Rate | Rate Unit | Active ingredients (mg/L) |
|---|---|---|---|
| adjuvant (Dehscofix CO 95) (control) | 0.1% | v/v | — |
| fungicide (Aliette) | 400 | mg/L | fosetyl-Al (320) |
| fungicide (Aliette) | 800 | mg/L | fosetyl-Al (640) |
| fungicide (Aliette) | 1600 | mg/L | fosetyl-Al (1280) |
| fungicide (Aliette) + elicitor | 400 50 | mg/L mg/L | fosetyl-Al (320) oligosaccharidic complex (50) |
| + adjuvant (Dehscofix CO 95) fungicide (Aliette) + elicitor | 0.1% 800 50 | v/v mg/L mg/L | — fosetyl-Al (640) oligosaccharidic complex (50) |
| + adjuvant (Dehscofix CO 95) fungicide (Aliette) + elicitor | 0.1% 1600 50 | v/v mg/L mg/L | — fosetyl-Al(1280) oligosaccharidic complex (50) |
| + adjuvant (Dehscofix CO 95) elicitor | 0.1% 50 | v/v mg/L | — oligosaccharidic complex (50) |
| + adjuvant (Dehscofix CO 95) | 0.1% | v/v | — |

The elicitor was applied as a formulation with the adjuvant Dehscofix CO 95. The active ingredient in the elicitor was an oligosaccharidic complex consisting of oligo-galacturonans (with degrees of polymerization between 9 and 20) and chito-oligosaccharides (with degrees of polymerization between 5 and 10 and with a degree of acetylation around 25%) in equal proportions. The elicitor further contained the salts $CaCl_2$ (0.5 mM) and NaCl (50 mM) to ensure good ionic conditions for the stability of the oligosaccharidic complex and sucrose (10 mM). The elicitor was applied at 50 mg active ingredient/L. The fungicide used was Aliette, which was chosen for its favorable ecotoxicological profile and versatile plant protection effect against oomycetes. Aliette was provided as a powder comprising 80% of its active ingredient fosetyl-Al. Aliette was applied at 400, 800 or 1600 mg/L, whereas the recommended rate is 8000 g/L. Control plants were sprayed with Dehscofix C095, the adjuvant used in the elicitor formulation.

24 h after treatment, the leaves were sampled from each plant individually, immediately frozen in liquid nitrogen and stored at −80° C. until use.

All samples were tested for peroxidase activity according to the assay procedure (Ref. No. FGAP001) for peroxidase (Guaiacol Units) provided by Faizyme Laboratories (http://www.faizyme.com/assaperg.htm). Frozen samples were ground in liquid nitrogen to fine powder with a RETSCH MM 400 crusher. Proteins were extracted using acetate buffer (0.1 M, pH 5.2) containing β-mercaptoethanol (0.014 M). Briefly, 0.5 g leaf powder was homogenized with an Ultra-Turrax (IKA) and centrifuged at 4000 rpm (4° C.) for 10 min. The supernatant was collected and filtered through Miracloth (Calbiochem) and directly frozen with liquid nitrogen. Protein contents were measured at 630 nm using Bio Rad protein assay reagent with bovine serum albumin as standard. The peroxidase activity assays were made on fresh extracts. Guaiacol (0.17 M) and $H_2O_2$ (0.19 M) were used as substrates. Kinetics of tetraguaiacol formation was determined by measuring absorbance every minute at 420 nm. The slope of the data allowed to express peroxidase activity in "µmol $H_2O_2.h^{-1}$·mg protein$^{-1}$" and results were normalized by setting treatment with adjuvant (control) at 100%. All measurements were performed using ELx800 Universal Microplate Reader spectrophotometer (Bio-Tek, instruments, INC) and statistic analyses were made with Minitab software (Minitab, 2007).

Figure 8:
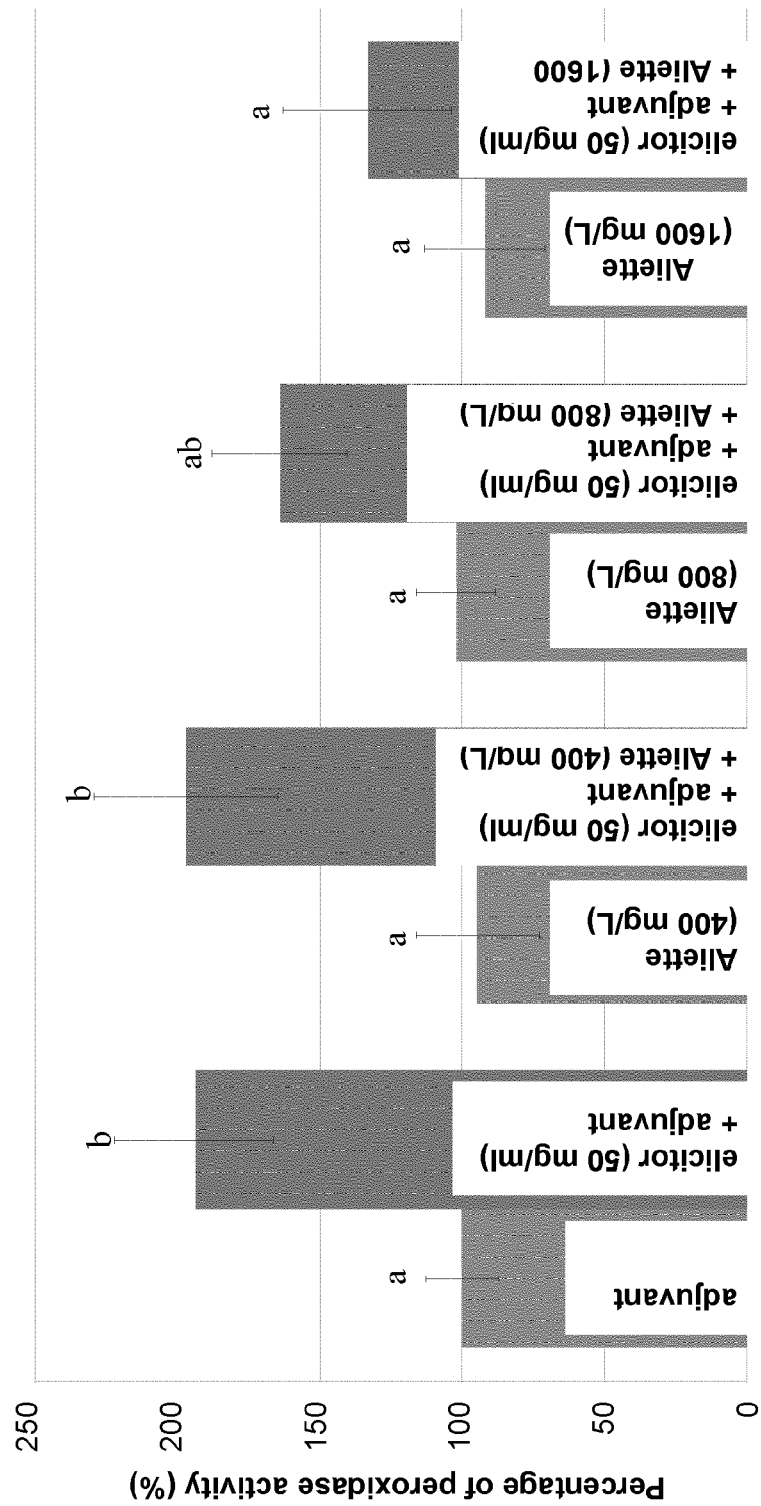
FIG. 8: Comparison of the peroxidase activity of tomato plants (*Solanum lycopersicum*, var. *Saint-Pierre*) treated with elicitor, fungicide (Aliette) applied at reduced rates (cf. example 5) or a combination of both. Standardized peroxidase activity of tomato leaves is shown 24 hours after treatment of the plants as indicated. Data are presented as mean±SE. Data were analyzed with an Anova, $p<0.05$ and bars with different letters (e.g. "a" or "b") are considered as being significantly different from each other.

FIG. 8 shows the effect of the different test solutions on the peroxidase activity of the tomato leaves.

The fungicide (Aliette) applied alone did not significantly modify the peroxidase activity of the tomato leaves. Addition of the elicitor statistically increased the peroxidase activity. Thus, mixing the elicitor with Aliette confers peroxidase activity to the plant on top of intrinsic fungicide effect. Unexpectedly, the fungicide used appears to negatively influence the elicitor effect. By reducing the concentration of the fungicide, we could increase induction of the plant immune system by the elicitor.

Example 6

Comparison of Peroxidase Activity of Tomato Treated with an Elicitor Alone or Combined with a Fungicide (Greenhouse Trial)

Tomato plants (*Lycopersicon esculentum*, variety *Saint Pierre*) were treated as in example 4. The composition of the test solutions is detailed in Table 6.

TABLE 6

Compositions of test solutions applied on tomato.

| Test solution | Rate | Rate Unit | Active ingredients (mg/L) |
|---|---|---|---|
| adjuvant (Dehscofix CO 95) (control) | 0.1% | v/v | — |
| elicitor | 25 | mg/L | oligosaccharidic complex (25) |
| + adjuvant (Dehscofix CO 95) elicitor | 0.1% 50 | v/v mg/L | — oligosaccharidic complex (50) |
| + adjuvant (Dehscofix CO 95) elicitor | 0.1% 75 | v/v mg/L | — oligosaccharidic complex (75) |
| + adjuvant (Dehscofix CO 95) fungicide (Aliette) + elicitor | 0.1% 400 25 | v/v mg/L mg/L | — fosetyl-Al (320) oligosaccharidic complex (25) |
| + adjuvant (Dehscofix CO 95) fungicide (Aliette) + elicitor | 0.1% 400 50 | v/v mg/L mg/L | — fosetyl-Al (320) oligosaccharidic complex (50) |
| + adjuvant (Dehscofix CO 95) fungicide (Aliette) + elicitor | 0.1% 400 75 | v/v mg/L mg/L | — fosetyl-Al (320) oligosaccharidic complex (75) |
| + adjuvant (Dehscofix CO 95) | 0.1% | v/v | — |

The elicitor was applied as a formulation with the adjuvant Dehscofix CO 95. The active ingredient in the elicitor was an oligosaccharidic complex consisting of oligo-galacturonans (with degrees of polymerization between 9 and 20) and chito-oligosaccharides (with degrees of polymerization between 5 and 10 and with a degree of acetylation around 25%) in equal proportions. The elicitor further contained the salts $CaCl_2$ (0.5 mM) and NaCl (50 mM) to ensure good ionic conditions for the stability of the oligosaccharidic complex and sucrose (10 mM). The elicitor was applied at 25, 50 or 75 mg active ingredient/L. The fungicide used was Aliette, which was chosen for its favorable ecotoxicological profile and versatile plant protection effect against oomycetes. Aliette was provided as a powder comprising 80% of its active ingredient fosetyl-Al. Aliette was applied at 400 mg/L, whereas the recommended rate is 8000 g/L. Control plants were sprayed with Dehscofix CO 95, the adjuvant used in the elicitor formulation.

24 h after treatment, the leaves were sampled from each plant individually, immediately frozen in liquid nitrogen and stored at −80° C. until use.

All samples were tested for peroxidase activity according to experiment 5.

Figure 9:
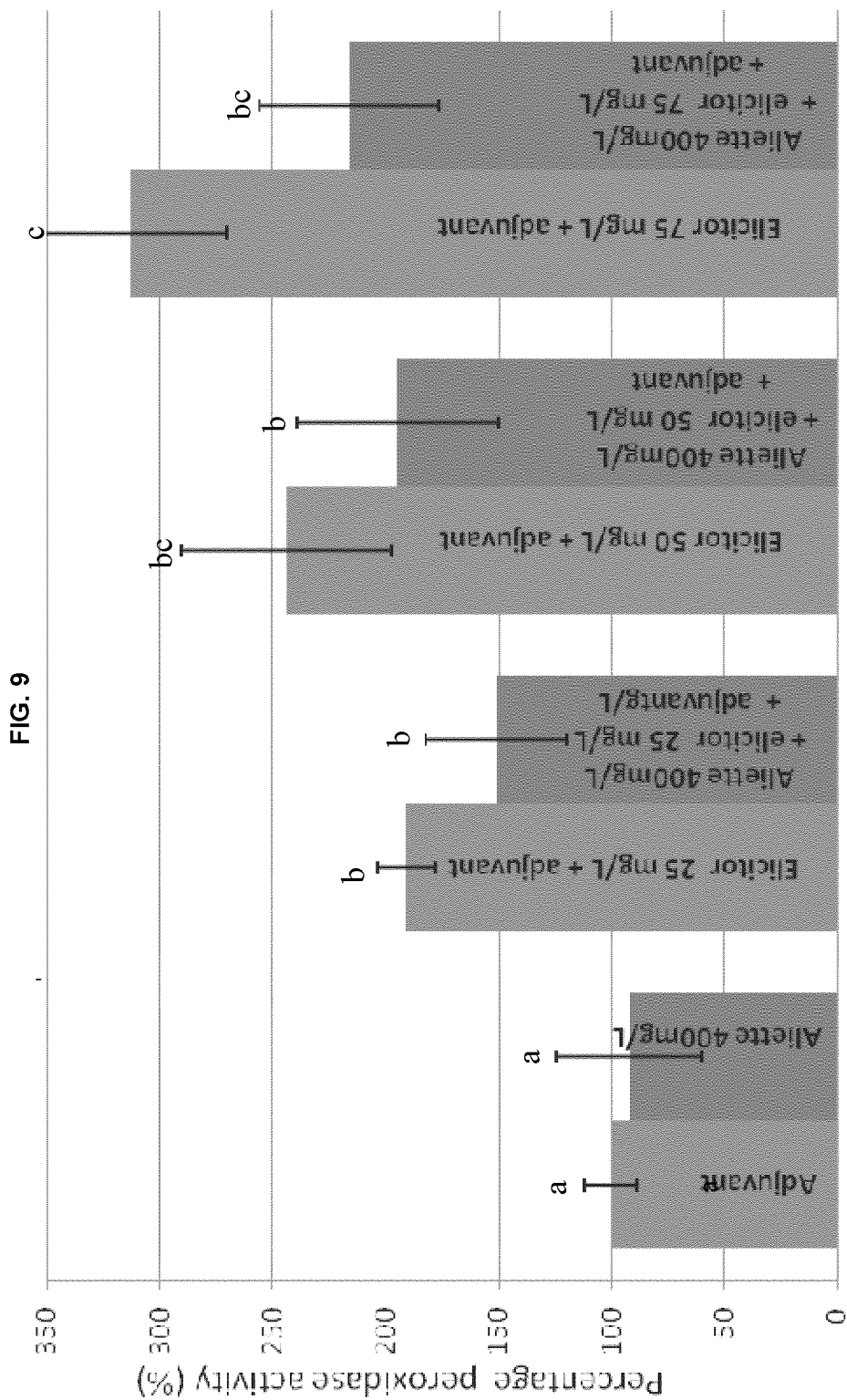
FIG. 9: Effects of the elicitor applied alone or in combination with a fungicide (Aliette) on the peroxidase activity of tomato plants (*Solanum lycopersicum*, var. *Saint-Pierre*). Standardized peroxidase activity of tomato leaves (*Solanum lycopersicum*, var. *Saint-Pierre*) is shown 24 hours after treatment of the plants as indicated. Data are presented as mean±SE. Data were analyzed with an Anova, $p<0.05$ and bars with different letters (e.g. "a" or "b") are considered as being significantly different from each other.

FIG. 9 shows the effects of the elicitor applied alone or in combination with fungicide on the peroxidase activity of the tomato leaves.

Peroxidase activity is significantly increased by application of the elicitor to tomato. In the elicitor range tested alone (0 mg/L, 25 mg/L, 50 mg/L, 75 mg/L) peroxidase activity appears to increase in a linear way with the concentration of the elicitor. The $R^2$ (determination coefficient) of this relationship is about 87% which is quite good for a biological response. The fungicide (Aliette) applied alone did not significantly modify the peroxidase activity of the tomato leaves.

When applied in combination with the elicitor, the peroxidase activity of the leaves also increases with the elicitor concentration. However, in combination with the fungicide, the elicitor concentration must be higher to yield similar activity than the one obtained with the elicitor sprayed alone at the same rate. Mixing the elicitor with the fungicide confers peroxidase activity to the plant on top of intrinsic fungicide effect of Aliette.

Example 7

Comparison of Peroxidase Activity of Tomato Treated with an Elicitor Alone or Formulated with Different Surfactants (Greenhouse Trial)

Tomato plants (*Lycopersicon esculentum*, variety *Saint Pierre*) were treated as in example 4. The composition of the test solutions is detailed in Table 7.

TABLE 7

Compositions of test solutions applied on tomato.

| Test solution | Rate | Rate Unit | Active ingredients (mg/L) |
|---|---|---|---|
| elicitor | 50 | mg/L | oligosaccharidic complex (50) |
| elicitor | 50 | mg/L | oligosaccharidic complex (50) |
| + Dehscofix CO 95 | 0.1% | v/v | — |
| elicitor | 50 | mg/L | oligosaccharidic complex (50) |
| + Tensiofix Dp400 | 0.1% | v/v | — |
| elicitor | 50 | mg/L | oligosaccharidic complex (50) |
| + Tensiofix D33 | 0.1% | v/v | — |

The elicitor was either applied alone or formulated with different surfactants. The surfactants were added at 0.1 volume percent to the elicitor formulation. Dehscofix CO 95 is an ethoxylated castor oil, a non-ionic plant oil. Tensiofix D33 (Ajinomoto OmniChem, Belgium) is a non-ionic wetter spreader agent and Tensiofix Dp400 (Ajinomoto OmniChem, Belgium) is an anionic salt that exhibits dispersing properties. The active ingredient in the elicitor was an oligosaccharidic complex consisting of oligo-galacturonans (with degrees of polymerization between 9 and 20) and chito-oligosaccharides (with degrees of polymerization between 5 and 10 and with a degree of acetylation around 25%) in equal proportions. The elicitor further contained the salts $CaCl_2$ (0.07 mM) and $KNO_3$ (8 mM) to ensure good ionic conditions for the stability of the oligosaccharidic complex and sucrose (10 mM). The elicitor was applied at 50 mg active ingredient/L.

24 h after treatment, the leaves were sampled from each plant individually, immediately frozen in liquid nitrogen and stored at −80° C. until use.

All samples were tested for peroxidase activity according to experiment 5.

Figure 10:
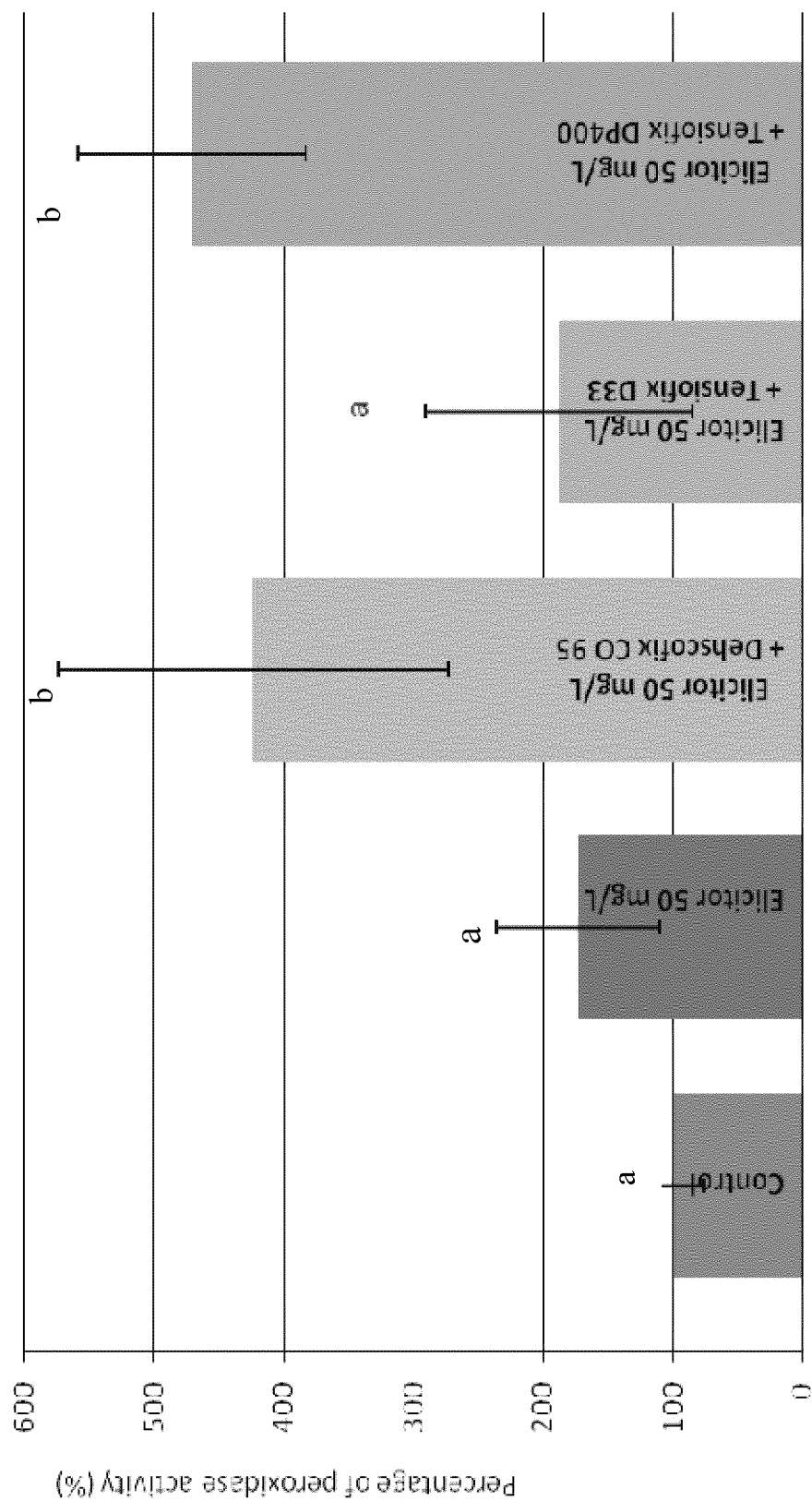
FIG. 10: Effect of surfactants on the peroxidase activity of tomato plants (*Solanum lycopersicum*, var. *Saint-Pierre*) induced by the elicitor. Standardized peroxidase activity of tomato leaves (*Solanum lycopersicum*, var. *Saint-Pierre*) is shown 24 hours after treatment of the plants as indicated. Data are presented as mean±SE. Data were analyzed with an Anova, $p<0.05$ and bars with different letters (e.g. "a" or "b") are considered as being significantly different from each other.

FIG. 10 shows the effect of the surfactants on the peroxidase activity of the tomato leaves induced by the elicitor.

Dehscofix CO 95, a penetration enhancer, and Tensiofix Dp 400, a dispersing agent, both in combination with the elicitor gave a twofold increase of the peroxidase activity in comparison with the elicitor alone.

Example 8

Comparison of Peroxidase Activity of Potato Treated with Elicitor Combinations (Greenhouse Trial)

Potato plants (*Solanum tuberosum*, variety *Bintje*) were grown under controlled conditions in a greenhouse (24° C., 16 h day/8 h night regime) for 6 weeks.

The plants were treated twice: a first application of the treatments was performed 7 days before harvest of the leaves, a second application was made 3 days before harvest. For each treatment, 8 potato plants were sprayed with 200 mL of a test solution on both sides of the leaves until run off. The composition of the test solutions is detailed in Table 8.

TABLE 8

Compositions of test solutions applied on potato.

| Test solution | Rate | Rate Unit | Active ingredients (mg/L) |
|---|---|---|---|
| adjuvant (Dehscofix CO 95) (control) | 0.1% | v/v | — |
| elicitor | 50 | mg/L | oligosaccharidic complex (50) |
| + adjuvant (Dehscofix CO 95) | 0.1% | v/v | — |
| elicitor | 50 | mg/L | oligosaccharidic complex (50) |
| + adjuvant (Dehscofix CO 95) + Vacciplant Fruit elicitor | 0.1% v/v 0.25% v/v | | — laminarin (45000) |
| Vacciplant Fruit elicitor | 0.25% | v/v | laminarin (45000) |

The elicitor was applied as a formulation with the adjuvant Dehscofix CO 95. The active ingredient in the elicitor was an oligosaccharidic complex consisting of oligo-galacturonans (with degrees of polymerization between 9 and 20) and chito-oligosaccharides (with degrees of polymerization between 5 and 10 and with a degree of acetylation around 25%) in equal proportions. The elicitor further contained the salts $CaCl_2$ (0.07 mM) and $KNO_3$ (14 mM) to ensure good ionic conditions for the stability of the oligosaccharidic complex. The elicitor was applied at 50 mg active ingredient/L. In one treatment, the elicitor was combined with a second elicitor, Vacciplant Fruit. Vacciplant Fruit was obtained from Belchim (Belgium) and contained laminarin (a linear $\beta(1\rightarrow3)$-glucan with $\beta(1\rightarrow6)$-linkages) as active ingredient. Vacciplant Fruit was applied at the recommended rate of 0.25% (v/v). Control plants were sprayed with Dehscofix CO 95, the adjuvant used in the elicitor formulation.

3 days after the second application of the treatments, 3 leaves at the same physiological stage were sampled per plant. The leaves of 2 plants were combined, immediately frozen in liquid nitrogen and stored at −80° C. until use.

All samples were tested for peroxidase activity as detailed in example 5.

Figure 11:
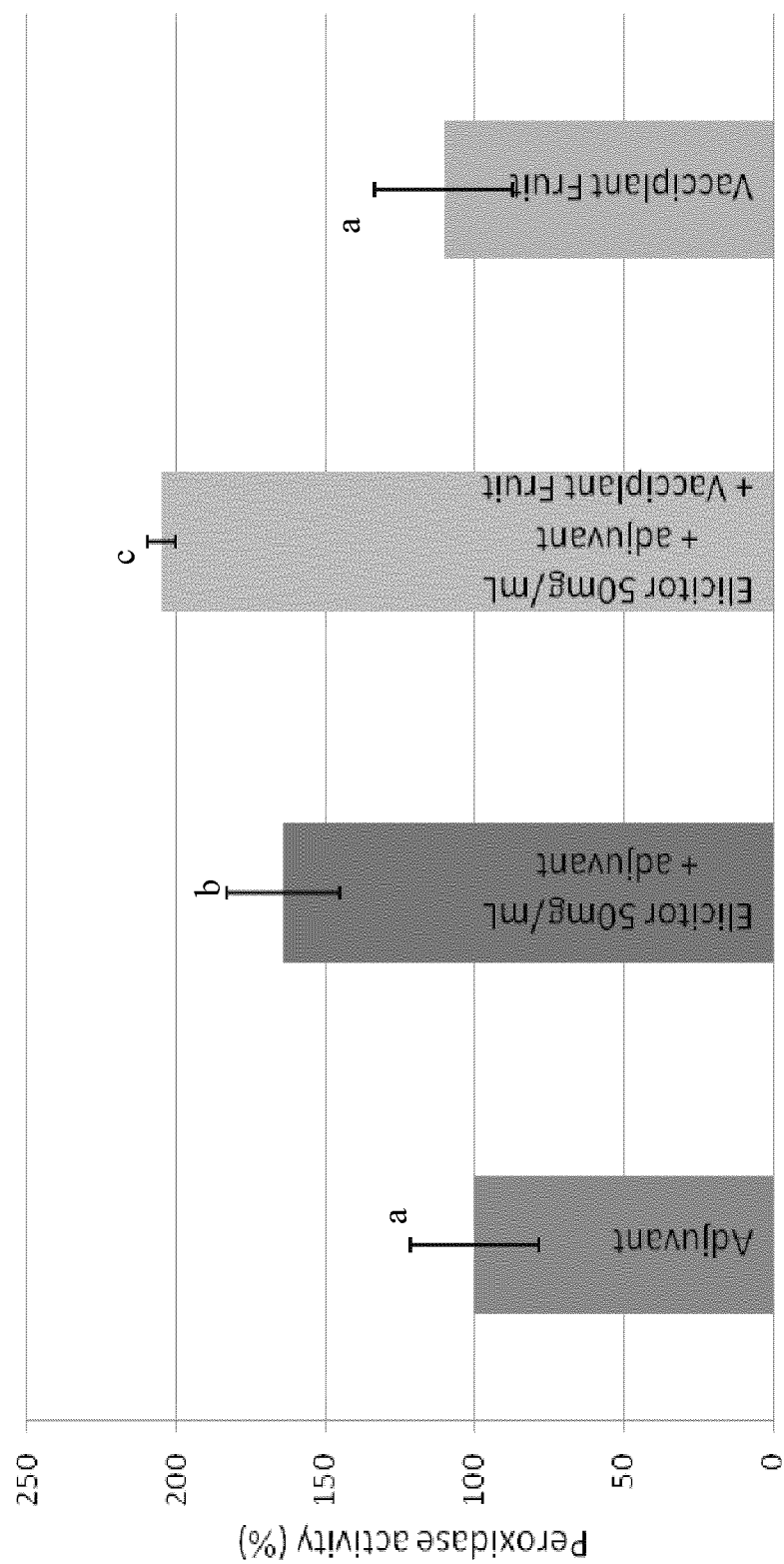
FIG. 11: Effect of a second elicitor (Vacciplant Fruit) on the peroxidase activity of potato plants (*Solanum tuberosum*, var. *Bintje*) induced by the chito-oligosaccharide—oligo-galacturonan elicitor. Standardized peroxidase activity of potato leaves is shown 3 days after the second treatment of the plants as indicated. Data are presented as mean±SE. Data were analyzed with an Anova, $p<0.05$ and bars with different letters (e.g. "a" or "b") are considered as being significantly different from each other.

FIG. 11 shows the effect of combining the chito-oligosaccharide—oligo-galacturonan (COS-OGA) elicitor with a second elicitor (Vacciplant Fruit) on the induction of peroxidase activity.

When applied alone, the second elicitor, Vacciplant Fruit, did not improve peroxidase activity as compared with the control. Spraying plants with the COS-OGA elicitor yielded a significant increase of peroxidase activity. A synergistic effect was obtained when the COS-OGA elicitor was combined with the Vacciplant Fruit elicitor.

Example 9

Efficacy of the Oligosaccharidic Elicitor in Controlling *Chaetosiphon fragaefolii* (Aphids) on Strawberry Strawberries (cultivar Anaïs) were grown in cages. Three cages, each containing 3 strawberry plants were used in this experiment.

At day D-7 and D-1 the strawberry plants were treated with an elicitor. The elicitor was provided as a liquid formulation comprising 10 g/L of active ingredient, which was an oligosaccharidic complex consisting of negatively charged oligo-galacturonans stabilized by positively charged chito-oligosaccharides. After dilution (200 fold), the elicitor was applied at 50 ppm.

Six adult aphids (*Chaetosiphon fragaefolii*) were put on each strawberry plant at day D-0.

Assessments of the aphids' numbers were made on 3 plants randomly selected (one in each from 3 replicates) at days D+19 and D+26.

Figure 12:
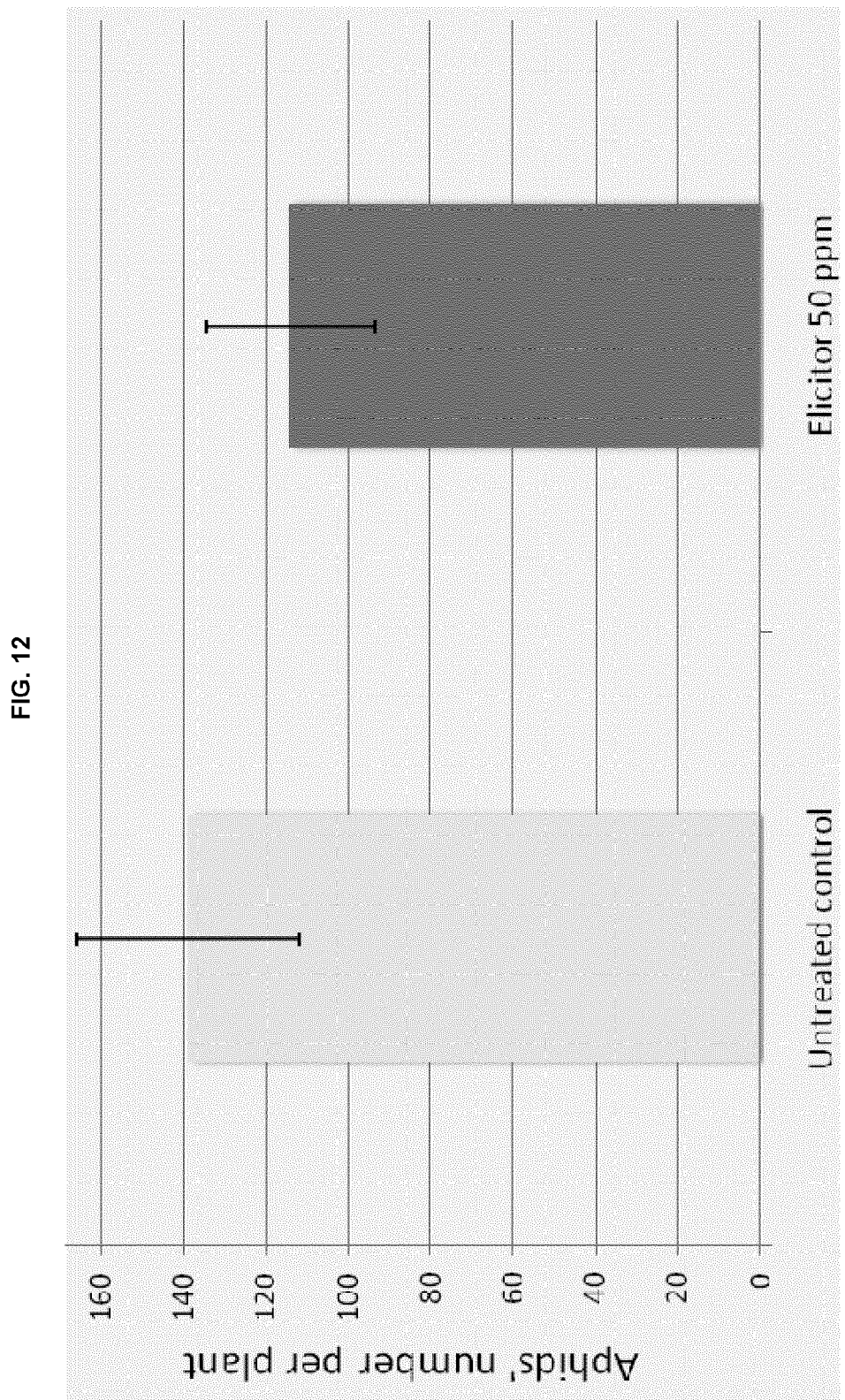
FIG. 12: Efficacy of the chito-oligosaccharide—oligo-galacturonan elicitor in controlling *Chaetosiphon fragaefolii* (aphids) on strawberry (cultivar Anaïs). Aphids development 19 days after inoculation is shown on untreated strawberry and strawberry treated twice (at 7 days and 1 day before inoculation) with the elicitor.

FIG. 12 shows the effects of the elicitor on aphids' development on strawberry plants 19 days after inoculation.

The number of aphids was 139 per plant for the untreated control, whereas the number of aphids was reduced at 114 per plant following elicitor applications. This corresponds to a reduction of the aphids by 18% in the presence of the elicitor.

Figure 13:
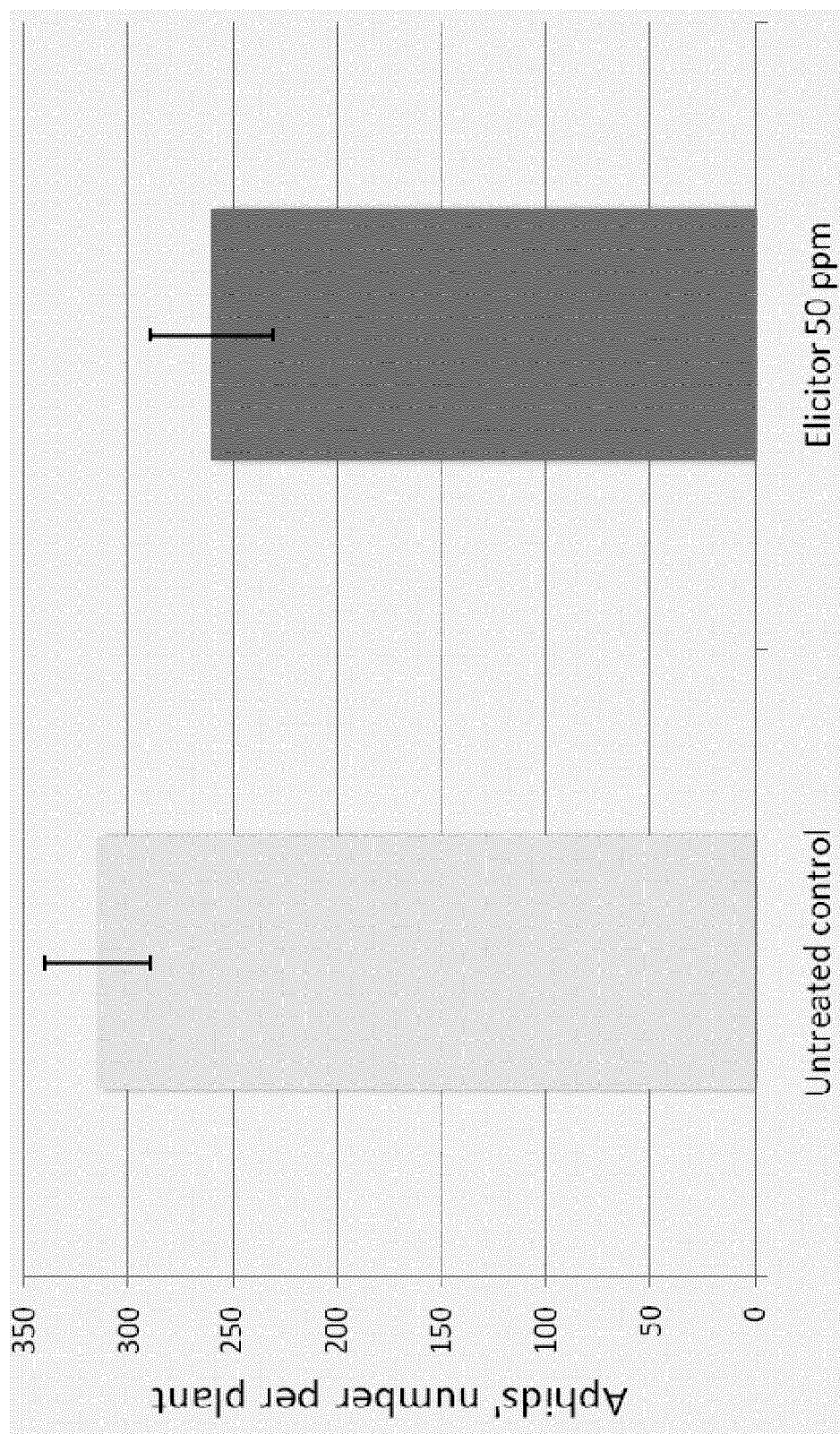
FIG. 13: Efficacy of the chito-oligosaccharide—oligo-galacturonan elicitor in controlling *Chaetosiphon fragaefolii* (aphids) on strawberry (cultivar Anaïs). Aphids development 26 days after inoculation is shown on untreated strawberry and strawberry treated twice (at 7 days and 1 day before inoculation) with the elicitor.

FIG. 13 shows the effects of the elicitor on aphids' development on strawberry plants 26 days after inoculation.

The number of aphids was 315 per plant for the untreated control, whereas the number of aphids was reduced at 260 per plant following elicitor applications. This corresponds to a reduction of the aphids by 17.5% in the presence of the elicitor. That means that the protection obtained after only two applications of the elicitor lasts at least one month.

Example 10

Comparison of the Efficacy of a Fungicide Applied Alone or in Mixture with an Elicitor in Controlling *Sphaerotheca fuliginea* (Powdery Mildew) on Cucumber Seedlings (Greenhouse Trial)

Cucumber seedlings were grown in a greenhouse.

The seedlings were treated with fungicide alone, elicitor alone or a combination of both as summarized in Table 9. The test solutions were applied once at day 0 and a second time at day +7 (2/4 leaves stage).

TABLE 9

Compositions of test solutions applied on cucumber.

| Test solution | Rate | Rate Unit | Active ingredients (mg/L) |
|---|---|---|---|
| fungicide (LEGEND) | 0.001 | L/hL | quinoxyfen (2.5) |
| elicitor | 0.8 | L/hL | oligosaccharidic complex (50) |
| + adjuvant (Dehscofix CO 95) | 0.08 | L/hL | — |
| fungicide (LEGEND) | 0.001 | L/hL | quinoxyfen (2.5) |

TABLE 9-continued

Compositions of test solutions applied on cucumber.

| Test solution | Rate | Rate Unit | Active ingredients (mg/L) |
|---|---|---|---|
| + elicitor | 0.8 | L/hL | oligosaccharidic complex (50) |
| + adjuvant (Dehscofix CO 95) | 0.008 | L/hL | — |

The fungicide used was LEGEND (Dow Agrosciences), which was chosen for its high level of protection of cucumber against *S. fuliginea* and because its mode of action consists in blocking the early signal transduction pathway. LEGEND comprises the active ingredient quinoxyfen at 250 g/L. The fungicide was applied at 0.001 L/hL, which is one twentieth of the maximal recommended rate.

The elicitor was applied as a formulation with the adjuvant Dehscofix CO 95. The active ingredient in the elicitor was an oligosaccharidic complex consisting of negatively charged oligo-galacturonans stabilized by positively charged chito-oligosaccharides in presence of recommended salts. The elicitor was provided as a concentrated solution comprising 6.25 g/L of active ingredient. The elicitor was applied at 0.8 L diluted in 100 L. The elicitor was applied with 0.08 L adjuvant Dehscofix CO 95 in 100 L, which is required for the penetration of the elicitor into leaves.

The fungicide and the elicitor (+0.08 L/hL Dehscofix CO 95) were also applied in mixture. Natural infestation occurred (from day +7) and additional artificial inoculation was carried out at day +10.

Assessments of leaf disease were made on 16 plants from 4 replicates. The percentages of leaves with symptoms of the disease (pest frequency) and the percentages of leaf area colonized by the disease (pest severity) were visually assessed. These assessments were performed at day +7 (only natural infestation) and +18 (also artificial inoculation) and the protection calculated with reference to the untreated control.

Figure 14:
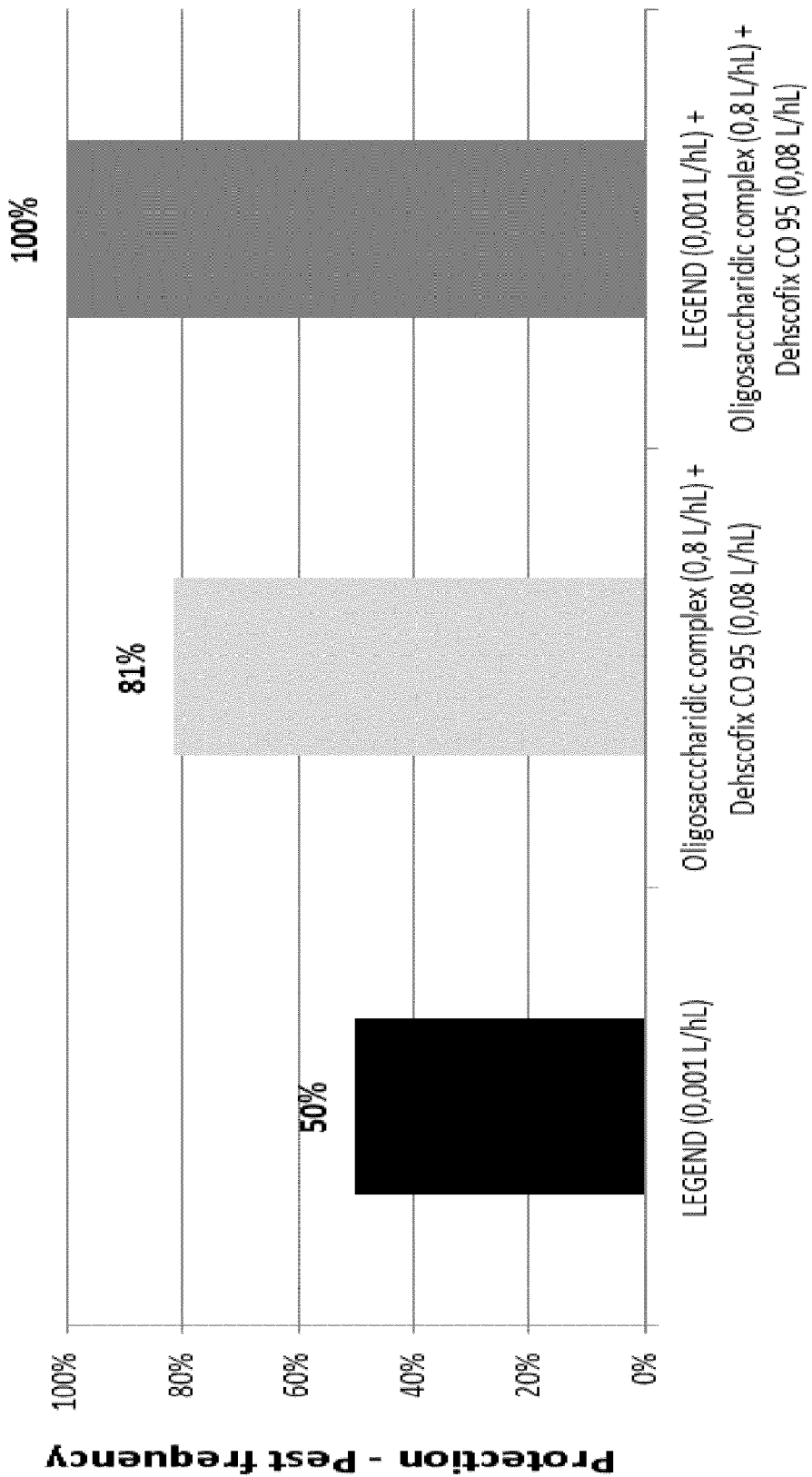
FIG. 14: Protection (expressed as reduction of pest frequency as compared to untreated seedlings) of cucumber seedlings against *Sphaerotheca fuliginea* offered by a fungicide (LEGEND) applied at a reduced rate (here about one twentieth of the maximal recommended rate), an elicitor (chito-oligosaccharide—oligo-galacturonan elicitor) applied as a formulation with an adjuvant (surfactant Dehscofix CO 95), or a combination of both. Pest frequency was assessed 7 days after treatment, when only natural infestation occurred.

FIG. 14 shows the effects of the treatments on the frequency of the disease caused by *S. fuliginea* on cucumber seedlings at day +7. At this moment only natural infestation occurred. The protection (expressed as reduction of pest frequency) was 50% for the fungicide and 81% for the elicitor (oligosaccharidic complex+Dehscofix CO 95), whereas protection reached 100% for the mixture of both (fungicide and elicitor).

Colby analysis shows that a synergistic effect exists between the fungicide and the elicitor concerning pest frequency. The observed percentage of protection (100%) is greater than the expected percentage of protection (90.5%), wherein E was calculated as:

$$E = 50 + 81 - \frac{50 \times 81}{100} = 90.5$$

Figure 15:
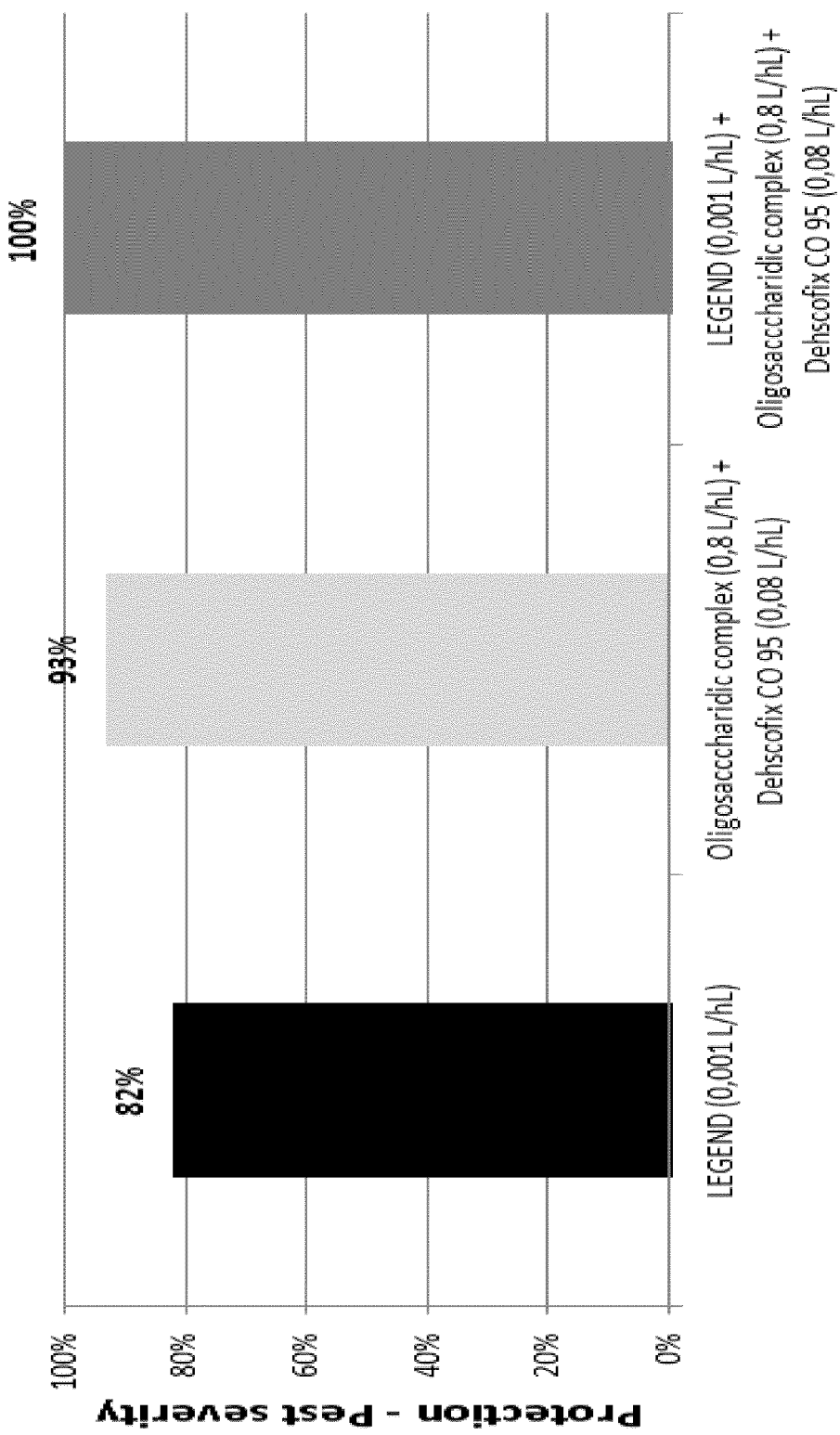
FIG. 15: Protection (expressed as reduction of pest severity as compared to untreated seedlings) of cucumber seedlings against *Sphaerotheca fuliginea* offered by a fungicide (LEGEND) applied at a reduced rate (here about one twentieth of the maximal recommended rate), an elicitor (chito-oligosaccharide—oligo-galacturonan elicitor) applied as a formulation with an adjuvant (surfactant Dehscofix CO 95), or a combination of both. Pest severity was assessed 7 days after treatment, when only natural infestation occurred.

FIG. 15 shows the effects of the treatments on the severity of the disease caused by *S. fuliginea* on cucumber seedlings at day +7.

The percentage of protection (expressed as reduction of pest severity) was 82% (for the fungicide) and 93% (for the elicitor), whereas the same parameter was assessed at 100% for the mixture of both fungicide and elicitor.

Colby analysis shows a slight synergistic effect exists between the fungicide and the elicitor regarding pest severity.

The observed percentage of protection (100%) is greater than the expected percentage of protection E (98.7%), wherein E was calculated as:

$$E = 82 + 93 - \frac{82 \times 93}{100} = 98.7$$

Figure 16:
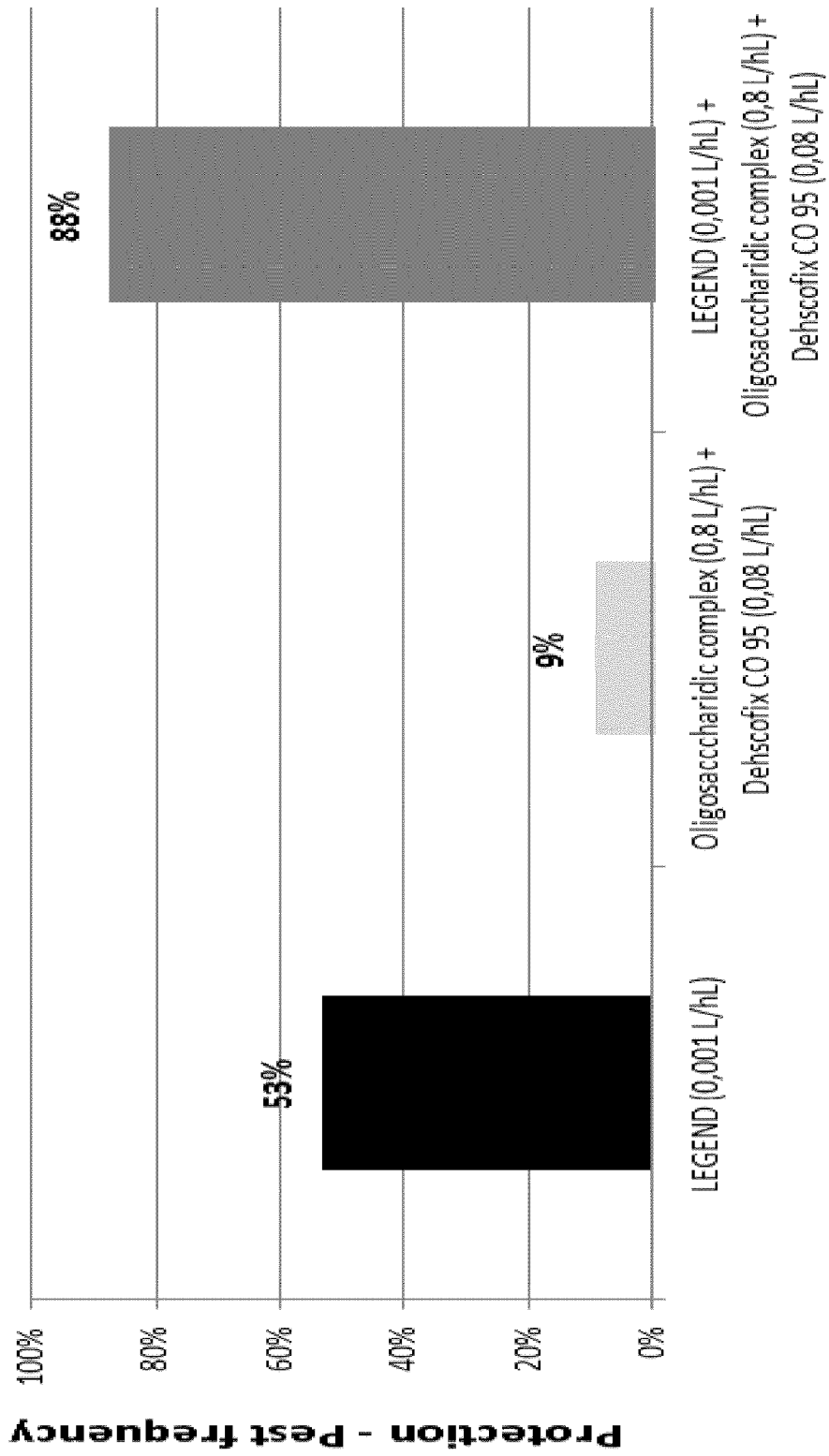
FIG. 16: Protection (expressed as reduction of pest frequency as compared to untreated seedlings) of cucumber seedlings against *Sphaerotheca fuliginea* offered by a fungicide (LEGEND) applied at a reduced rate (here about one twentieth of the maximal recommended rate), an elicitor (chito-oligosaccharide—oligo-galacturonan elicitor) applied as a formulation with an adjuvant (surfactant Dehscofix CO 95), or a combination of both. Pest frequency was assessed 18 days after treatment, when natural infestation occurred and also artificial inoculation.

FIG. 16 shows the effects of the treatments on the frequency of the disease caused by *S. fuliginea* on cucumber seedlings at day +18. At this moment the symptoms also resulted from artificial inoculation.

The percentage of protection (expressed as reduction of pest frequency) was 53% for the fungicide and 9% for the elicitor (oligosaccharidic complex+Dehscofix CO 95), whereas protection was assessed at 88% for the mixture of both (fungicide and elicitor).

Colby analysis shows that a synergistic effect exists between the fungicide and the elicitor concerning pest frequency. The observed percentage of protection (88%) is much higher than the expected percentage of protection E (57.2%), wherein E was calculated as:

$$E = 53 + 9 - \frac{53 \times 9}{100} = 57.2$$

Figure 17:
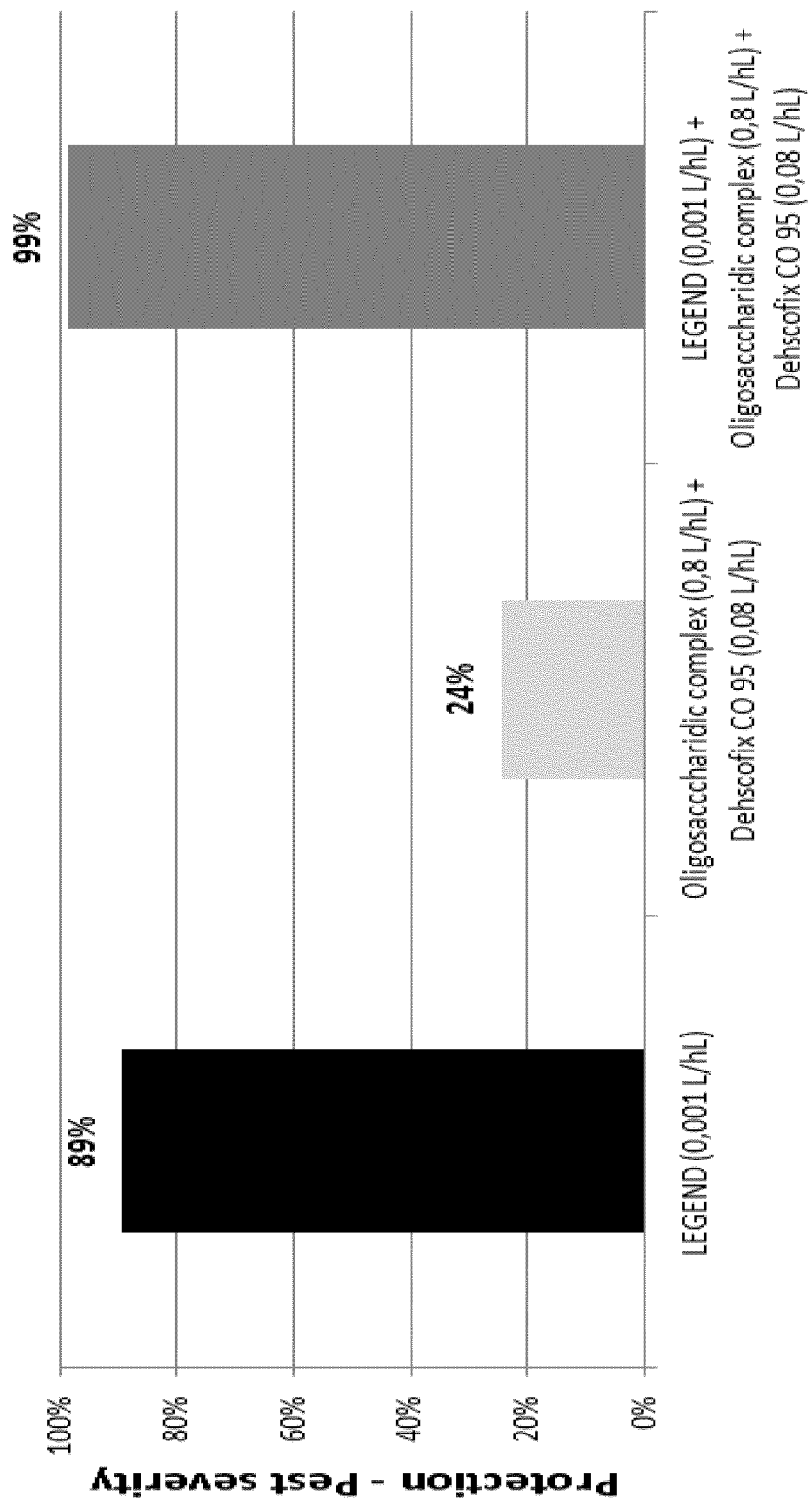
FIG. 17: Protection (expressed as reduction of pest severity as compared to untreated seedlings) of cucumber seedlings against *Sphaerotheca fuliginea* offered by a fungicide (LEGEND) applied at a reduced rate (here about one twentieth of the maximal recommended rate), an elicitor (chito-oligosaccharide—oligo-galacturonan elicitor) applied as a formulation with an adjuvant (surfactant Dehscofix CO 95), or a combination of both. Pest severity was assessed 18 days after treatment, when natural infestation occurred and also artificial inoculation.

FIG. 17 shows the effects of the treatments on the severity of the disease caused by *S. fuliginea* on cucumber seedlings at the same moment (day+18).

The percentage of protection (expressed as reduction of pest severity) was 89% (for the fungicide) and 24% (for the elicitor), whereas the same parameter was assessed at 99% for the mixture of both (fungicide and elicitor).

Colby analysis again shows a clear synergistic effect between the fungicide and the elicitor regarding pest severity. The observed percentage of protection (99%) is greater than the expected percentage of protection E (91.6%), wherein E was calculated as:

$$E = 89 + 24 - \frac{89 \times 24}{100} = 91.6$$

In conclusion, whatever the parameter (pest frequency and pest severity) and the assessment (at day +7 and day +18), a synergistic effect is observed between the elicitor and a very low rate of the fungicide LEGEND (quinoxyfen).

Example 11

Comparison of the Efficacy of a Sulfur-Containing Fungicide Applied Alone or in Mixture with an Elicitor in Controlling *Erysiphe necator* (Powdery Mildew) (Field Trial)

The field trial was carried out in a vineyard in France.

The grapevines were treated with fungicide alone, elicitor alone or a combination of both as summarized in Table 10. The total spray volume was 400 L/ha.

TABLE 10

Compositions of test solutions applied on grapevine.

| Test solution | Rate | Rate Unit | Active ingredients (g/ha) |
| --- | --- | --- | --- |
| fungicide (THIOVIT) | 25 | kg/ha | sulfur (20000) |
| elicitor | 4 | L/ha | oligosaccharidic complex (25) |
| + adjuvant (Dehscofix CO 95) | 0.4 | L/ha | — |
| fungicide (THIOVIT) | 20 | kg/ha | sulfur (16000) |
| + elicitor | 4 | L/ha | oligosaccharidic complex (25) |
| + adjuvant (Dehscofix CO 95) | 0.4 | L/hL | — |

The applied fungicide was THIOVIT, which contains 80% sulfur as active ingredient. THIOVIT was chosen because sulfur is widely used to preventively protect grapevine against *E. necator* (powdery mildew) and especially because it is a multisite fungicide along with compounds such as copper, dithiocarbamates, phthalimides, chloronitriles and triazines (http://frac.info/frac/publication/anhang/FRAC%20Code%20List%202011-final.pdf). THIOVIT was applied at 25 kg/ha/season, which is about one third of the recommended rate.

The active ingredient in the COS-OGA elicitor is an oligosaccharidic complex consisting of negatively charged oligo-galacturonans stabilized by positively charged chito-oligosaccharides. The elicitor was provided as a concentrated solution comprising 6.25 g/L of active ingredient. The elicitor was applied at 4 L/ha as a formulation with 0.4 L/ha adjuvant Dehscofix CO 95, which is required for the penetration of the elicitor into the leaves. THIOVIT and the elicitor (with 0.4 L/ha Dehscofix CO 95) were also applied in combination.

Assessment of leaves was made six weeks after appearance of infestation on fruits. The percentages of leaves with symptoms of the disease (pest frequency) and the percentages of leaf area colonized by the disease (pest intensity) were visually assessed and protection calculated with respect to untreated control.

Figure 18:
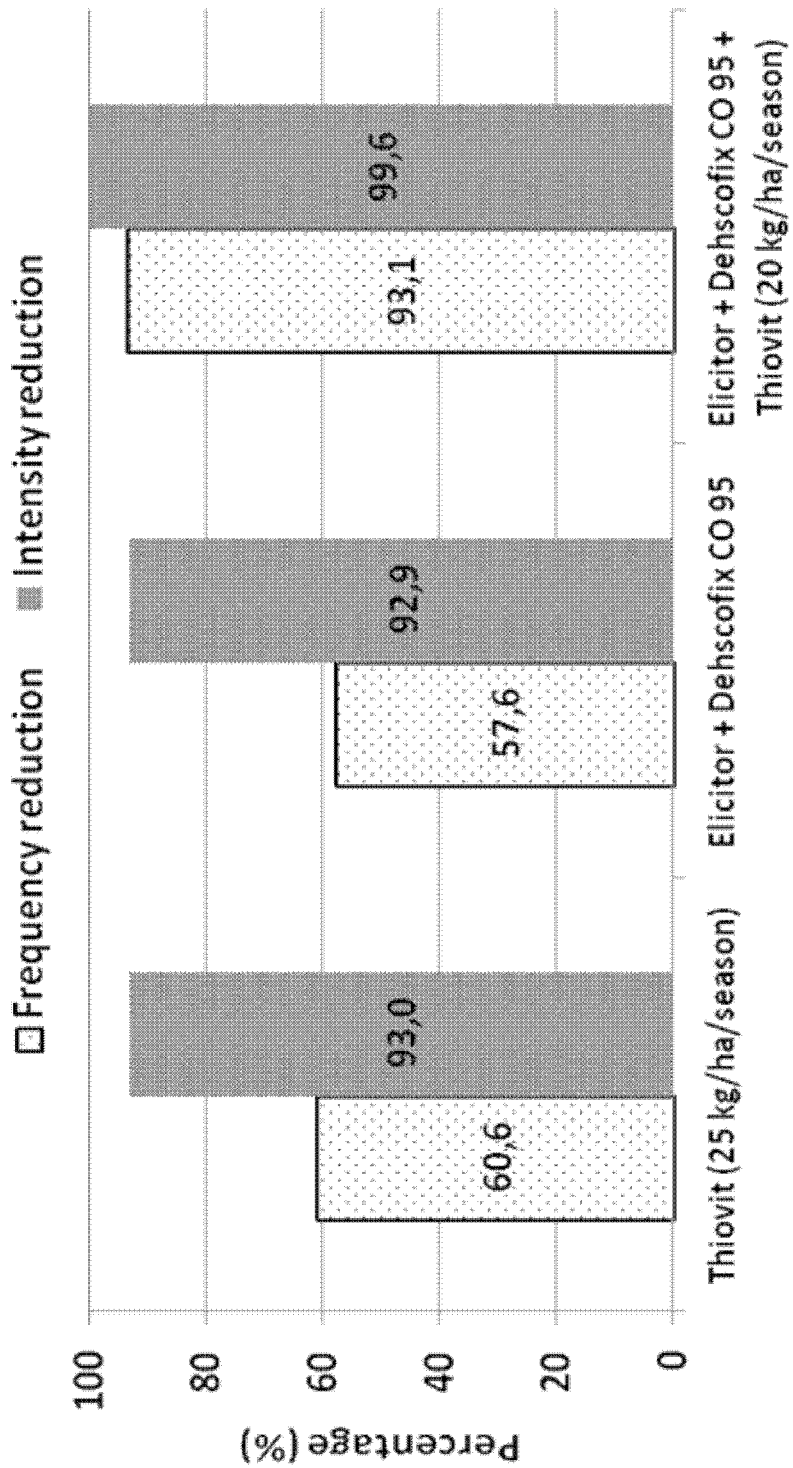
FIG. 18: Protection (expressed as frequency and intensity reduction of powdery mildew on leaves as compared to untreated grapevines) of grapevines against *Erysiphe necator* (*Uncinula necator*) following treatment with a sulfur-containing fungicide (THIOVIT), an elicitor (chito-oligosaccharide—oligo-galacturonan elicitor) applied as a formulation with an adjuvant (surfactant Dehscofix CO 95), or a mixture of both. Assessment of the leaves was made six weeks after the first symptoms of powdery mildew appeared on the control (untreated grapevines).

FIG. 18 shows the effects of the treatments on the frequency and the severity of the disease caused by *E. necator* on leaves six weeks after the first symptoms appeared on the untreated control.

Frequency reduction for the THIOVIT fungicide alone was 60.6% whereas this parameter was assessed at 57.6% for the elicitor (oligosaccharidic complex+Dehscofix CO 95) alone. Frequency reduction for the mixture of both THIOVIT and elicitor was 93.1%.

Colby analysis demonstrates that a synergistic effect exists between the COS-OGA elicitor and the multisite fungicide THIOVIT concerning pest frequency. The observed percentage of protection (93.1%) is greater than the expected percentage of protection E (83.3%), which was calculated as:

$$E = 60.6 + 57.6 - \frac{60.6 \times 57.6}{100} = 83.3$$

Example 12

Comparison of Peroxidase Activity of Tomato Treated with an Elicitor Alone or Formulated with a Surfactant (Greenhouse Trial)

Tomato plants (*Solanum lycopersicum*, var. *Moneymaker*) were grown for four weeks at 24° C. with a 16 h/8 h day/night regime and were well watered every two to three days. Twenty four hours before treatment, well watered plants were transferred in a growth cabinet at constant temperature (18° C.) and humidity (90%) under the same photoperiod. For each treatment, 12 plants were sprayed until run off on both faces of the leaves with 200 mL of a test solution and returned to the incubator for one more day. The compositions of the test solutions are detailed in Table 11.

TABLE 11

Compositions of test solutions applied on tomato.

| Test solution | Rate | Rate Unit | Active ingredients |
|---|---|---|---|
| distilled water (control) | — | — | — |
| adjuvant (Dehscofix CO 95) | 0.1% | v/v | — |
| elicitor | 62.5 | ppm | oligosaccharidic complex |
| elicitor | 62.5 | ppm | oligosaccharidic complex (25) |
| + adjuvant (Dehscofix CO 95) | 0.1% | v/v | — |

Twenty four hours after treatment, the leaves were sampled, frozen in liquid nitrogen and stored at −80° C. until grinding in liquid nitrogen, protein extraction and peroxidase quantitation.

All samples were tested for peroxidise activity according to example 5.

Figure 19:
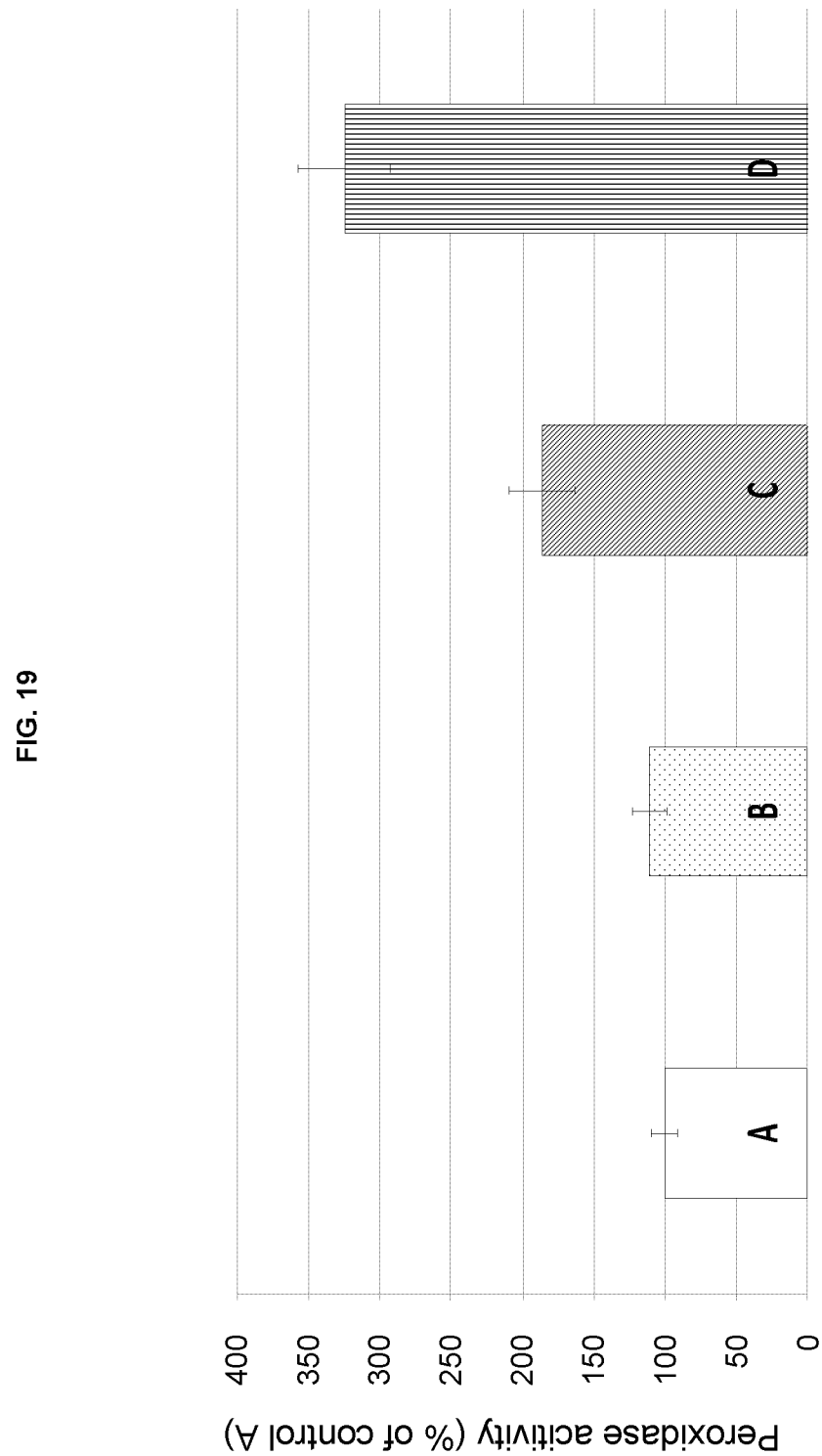
FIG. 19: Comparison of the peroxidase activity of tomato leaves (Solanum lycopersicum, var. *Moneymaker*) following treatment of the tomato plants with distilled water (control) (A), an adjuvant (surfactant Dehscofix CO 95, 0.1% (v/v)) (B), an elicitor (chito-oligosaccharide—oligo-galacturonan elicitor, 62.5 ppm) (C), or a combination of the elicitor (62.5 ppm) with the adjuvant (0.1% (v/v)) (D). Standardized peroxidase activity of the tomato leaves is shown 24 hours after treatment of the plants as indicated. Data are presented as mean±SE.

FIG. 19 shows the effects of the treatments on the peroxidase activity of the tomato leaves. The adjuvant Dehscofix CO 92 alone only offered a slight increase of peroxidase activity (10.7%) compared to the control treatment, whereas the peroxidase activity increase reached 85.7% with the COS-OGA elicitor treatment.

The peroxidase activity increase observed with the combination of the COS-OGA elicitor and the adjuvant Dehscofix CO 95 (225% as compared to water) is much greater than the expected increase E (87.2%), which was calculated as:

$$E = 10.7 + 85.7 - \frac{10.7 \times 85.7}{100} = 87.2\%$$

Consequently, a synergistic effect exists between the adjuvant Dehscofix CO 95 and the COS-OGA elicitor regarding peroxidase activity.

Example 13

Comparison of Peroxidase Activity of Tomato Treated with the COS-OGA Elicitor Co-Formulated with or without Na$_2$SiO$_3$ Elicitor (Greenhouse Trial)

Tomato plants (Solanum lycopersicum, var. *Moneymaker*) were grown for four weeks at 24° C. with a 16 h/8 h day/night regime and were well watered every two to three days.

Twenty four hours before treatment, well watered plants were transferred in a growth cabinet at constant temperature (18° C.) and humidity (90%) under the same photoperiod. For each treatment, 12 plants were sprayed until run off on both faces of the leaves with 200 mL of a test solution and returned to the incubator for one more day. The compositions of the test solutions are detailed in Table 12.

TABLE 12

Compositions of test solutions applied on tomato.

| Test solution | Rate | Rate Unit | Active ingredients |
|---|---|---|---|
| A: distilled water (control) | — | — | — |
| B: COS-OGA elicitor | 50 | ppm | oligosaccharidic complex |
| + adjuvant (Dehscofix CO 95) | 0.1% | v/v | — |
| C: Na$_2$SiO$_3$ elicitor | 2 | mM | Na$_2$SiO$_3$ |
| + adjuvant (Dehscofix CO 95) | 0.1% | v/v | — |
| D: Na$_2$SiO$_3$ elicitor | 5 | mM | Na$_2$SiO$_3$ |
| + adjuvant (Dehscofix CO 95) | 0.1% | v/v | — |
| E: COS-OGA elicitor | | | oligosaccharidic complex |
| + Na$_2$SiO$_3$ elicitor | 2 | mM | Na$_2$SiO$_3$ |
| + adjuvant (Dehscofix CO 95) | 0.1% | v/v | — |
| F: COS-OGA elicitor | | | oligosaccharidic complex |
| + Na$_2$SiO$_3$ elicitor | 5 | mM | Na$_2$SiO$_3$ |
| + adjuvant (Dehscofix CO 95) | 0.1% | v/v | — |

Twenty four hours after treatment, the leaves were sampled, frozen in liquid nitrogen and stored at −80° C. until grinding in liquid nitrogen, protein extraction and peroxidase quantitation. All samples were tested for peroxidise activity according to example 5.

Figure 20:
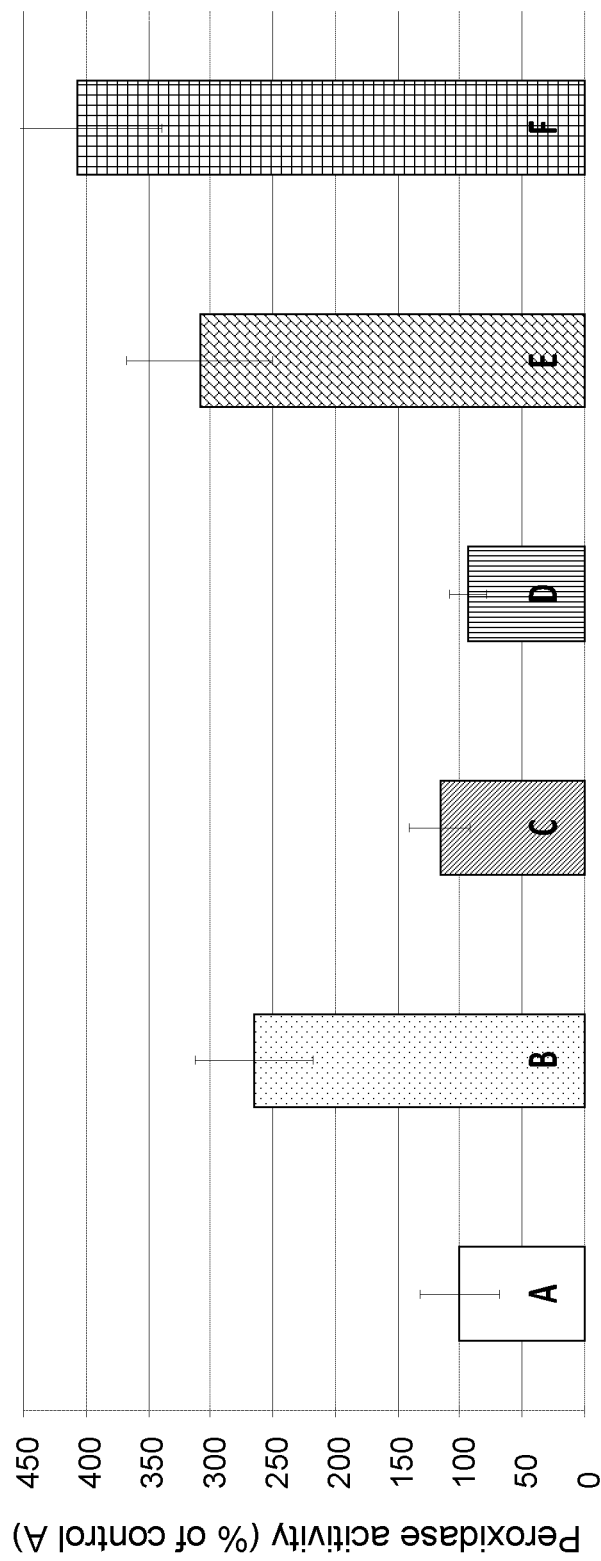
FIG. 20: Comparison of the peroxidase activity of tomato leaves (*Solanum lycopersicum*, var. *Moneymaker*) following treatment of the tomato plants with an adjuvant (surfactant Dehscofix CO 95) (A), an oligosaccharidic (chito-oligosaccharide—oligo-galacturonan, 50 ppm) elicitor applied as a formulation with the adjuvant (B), a silicium elicitor ($Na_2SiO_3$) applied at 2 mM (C) or 5 mM (D) as a formulation with the adjuvant, or a combination of the adjuvant, the oligosaccharidic elicitor (50 ppm) and the silicium elicitor applied at 2 mM (E) or 5 mM (F), or a combination of the elicitor with the adjuvant. Standardized peroxidase activity of the tomato leaves is shown 24 hours after treatment of the plants as indicated. Data are presented as mean±SE.

FIG. 20 shows the effects of the treatments on the peroxidase activity of the tomato leaves. Treatment with the COS-OGA elicitor in combination with the Dehscofix adjuvant resulted in a 165% peroxidase activity increase compared to the control treatment, whereas the peroxidase activity increase only reached 16.1% in presence of 2 mM Na$_2$SiO$_3$ alone and even decreased slightly (−7%) in presence of 5 mM Na$_2$SiO$_3$ alone.

Colby analysis demonstrates that there is a synergistic effect between the COS-OGA elicitor and 2 mM Na$_2$SiO$_3$ regarding peroxidase activity. The observed peroxydase activity increase (209%) is much greater than the expected increase E (154%), which was calculated as:

$$E = 165 + 16 - \frac{165 \times 16}{100} = 154\%$$

Colby analysis shows that there is a synergistic effect between the COS-OGA elicitor in combination with 5 mM Na$_2$SiO$_3$ regarding peroxidase activity. The increase of peroxidase activity observed with the combination of COS-OGA elicitor and 5 mM Na$_2$SiO$_3$ (308% with respect to water) is much greater than the increase expected from the components alone (170%), which was calculated as:

$$E = 165 + (-7) - \frac{165 \times (-7)}{100} = 170\%$$

In conclusion, a synergistic effect exists between the COS-OGA elicitor in combination with the Dehscofix CO 95 adjuvant and the silicium elicitor (Na$_2$SiO$_3$) regarding peroxidase activity.

Example 14

Comparison of the Efficacy of the Fungicides Ranman Component A, Previcur N and Signum Applied Alone or in Mixture with an Elicitor in Controlling *Phytophthora infestans* on Potato (Under Controlled Conditions)

Potato plants (*Solanum tuberosum*, variety *Bintje*) were grown under controlled conditions. The plants were treated twice at days −7 and day −1 before artificial inoculation of the potato leaves (day 0) by spraying a test solution on the plants. Artificial inoculation was carried out by spotting droplets of 10 μl containing 5·10$^4$ *P. infestans* spores per ml on the lower leaf sides. The test solutions were composed of elicitor alone, fungicide alone or a combination of both. The fungicides tested were Ranman component A, Previcur N and Signum, which were chosen because they are widely used to protect potato against *P. infestans* (downy mildew). Ranman component A contains 400 g/L cyazofamid (an inhibitor of complex II of the electron transport chain of the mitochondria) as active ingredient, Previcur N contains 722 g/L propamocarb (a cell membrane permeability disruptor) as active ingredient and Signum contains 26.7% (w/w) pyraclostrobin and 6.7% (w/w) boscalid as active ingredients. The Ranman component A fungicide was applied at one thousandth of its recommended rate. The Previcur N and Signum fungicides were applied at one hundredth of their recommended rate. The fungicides were also applied in combination with the elicitor formulation. The active ingredient in the elicitor was an oligosaccharidic complex consisting of negatively charged oligo-galacturonans stabilized by positively charged chito-oligosaccharides. The elicitor was provided as a ready to use solution containing 50 mg/L of active ingredient and 0 1% (v/v) of the adjuvant Tensiofix DP400.

Assessment of the sporulation area on leaves was made each day between the third and the sixth day after artificial inoculation in order to calculate the Area Under Disease Progression Curve (AUDPC). By the end of the test, 100% of the leaf area of controls (untreated plants) were covered with sporulation.

Figure 21:
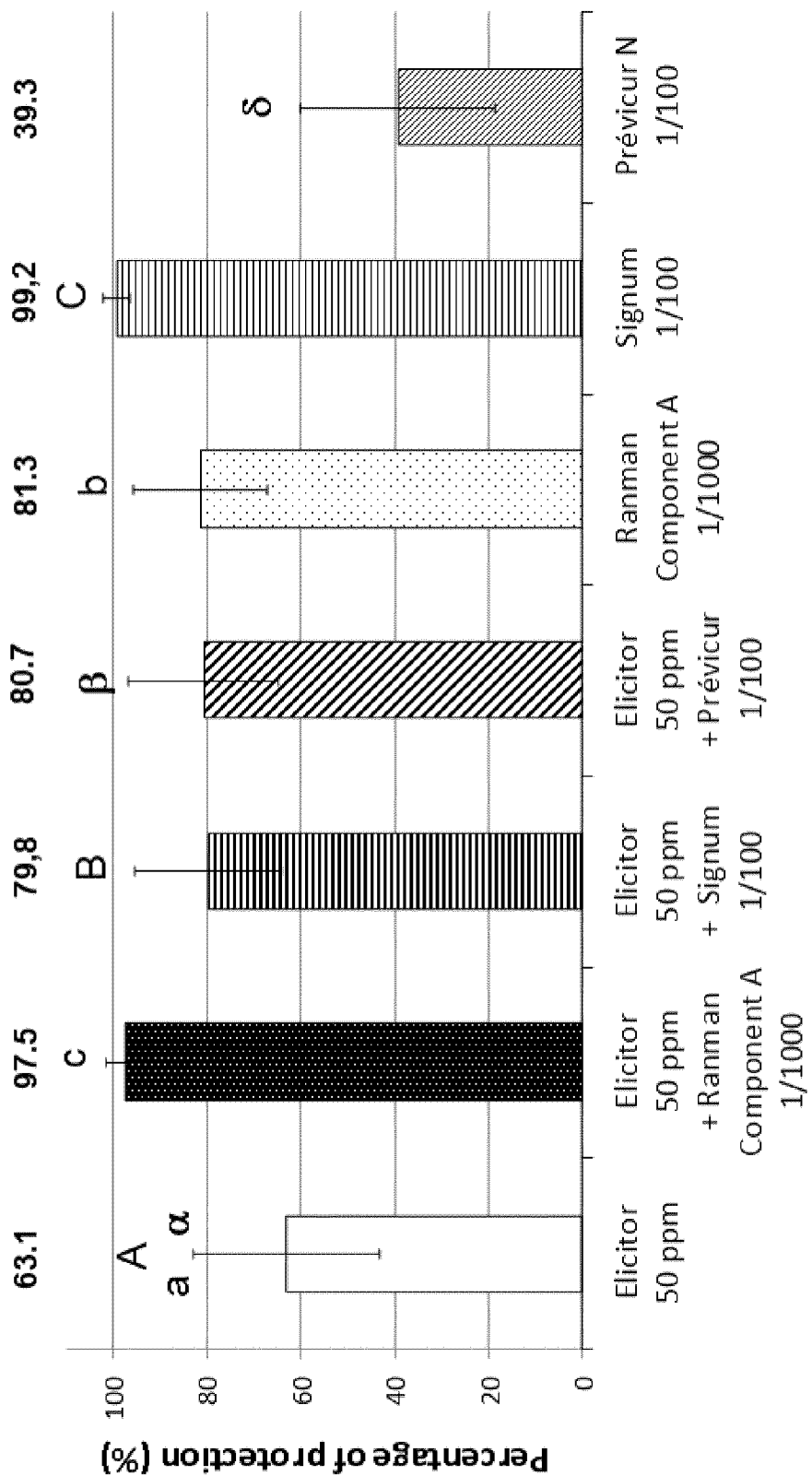
FIG. 21: Protection of potato leaves (*Solanum tuberosum* var. *Bintje*) against *P. infestans* offered by an oligosaccharidic (chito-oligosaccharide—oligo-galacturonan) elicitor applied as a formulation with an adjuvant (surfactant Tensiofix DP400), the Ranman component A fungicide applied at a reduced rate (here about one thousandth of the recommended rate), the Previcur fungicide applied at a reduced rate (here about one hundredth of the recommended rate), the Signum fungicide applied at a reduced rate (here about one hundredth of the recommended rate), or a combination of the formulated elicitor with one of the fungicides. Data are presented as mean±SE. Data were analyzed with Student's T test (n=24), p<0.05 and bars with different letters (e.g. "a" or "b") are considered as being statistically different from each other.

FIG. 21 shows protection of the treatments against sporulation caused by *P. infestans* on potato leaves calculated from the AUDPC of the control (untreated plants).

The fungicides applied alone offered a protection of 81.3% (Ranman component A), 39.3% (Previcur N) and 99.2% (Signum).

The elicitor applied alone offered a protection of 63.1%.

The observed percentage of protection (97.5%) offered by the combination of the Ranman component A fungicide and the elicitor is greater than the expected percentage of protection (93.1%), which was calculated as:

$$E = 81.3 + 63.1 - \frac{81.3 \times 63.1}{100} = 93.1\%$$

Consequently a synergistic effect exists between the COS-OGA elicitor and the fungicide Ranman component A regarding protection of potato against *P. infestans*.

The observed percentage of protection (80.7%) offered by the combination of the Previcur N fungicide and the elicitor is greater than the expected percentage of protection (77.6%), which was calculated as:

$$E = 39.3 + 63.1 - \frac{39.3 \times 63.1}{100} = 77.6\%$$

Consequently a synergistic effect also exists between the COS-OGA elicitor and the fungicide Previcur N regarding protection of potato against *P. infestans*.

The observed percentage of protection offered by the combination of the Signum fungicide and the elicitor was only 79.8%, which indicates that there was no synergy between the COS-OGA elicitor and this fungicide. In contrast, addition of the COS-OGA elicitor to the Signum fungicide had a clear antagonistic effect regarding protection of potato against *P. infestans*.

An antagonistic effect on plant protection of adding the COS-OGA elicitor to a fungicide was also observed with other fungicides (Table 13).

TABLE 13

Examples of fungicides that act antagonistically to the COS-OGA elicitor.

| Commercial name | Fungicide Active Ingredient | Fungicide class | Trial |
| --- | --- | --- | --- |
| Signum | pyraclostrobin 26.7% (w/w) and boscalid 6.7% (w/w) | methoxy carbamates and pyridine-carboxamides | In vitro trial on detached potato leaves and artificial inoculation with *P. infestans* |
| Paraat | dimetomorph 50% (w/w) | cinnamic acid amides | In vitro trial on detached potato leaves and artificial inoculation with *P. infestans* |

The invention claimed is:

1. A composition for protecting plants against plant pathogens comprising:
   a) an elicitor comprising one or more oligo-galacturonan(s) with a degree of polymerization between 9 and 20 and one or more chito-oligosaccharide(s) with a degree of polymerization between 5 and 10 and a degree of acetylation lower than 50% in proportions ranging from 1:10 to 10:1, and
   b) a fungicide selected from the group consisting of 2,6-dichloro-N-[3-chloro-5-(trifluoromethyl)-2-pyridinyl-methyl]benzamide; propyl 3-(dimethylamino)propyl-carbamate hydrochloride; (2RS, 3SR)-1-[3-(2-chlorophenyl)-2,3-epoxy-2-(4-fluorophenyl)propyl]-1H-1,2,4-triazole; 5,7-dichloro-4-quinolyl 4-fluorophenyl ether; sulphur; 4-chloro-2-cyano-N,N-dimethyl-5-(4-methylphenyl)-1H-imidazole-1-sulfonamide; and a combination thereof,
   c) optionally salts and/or sugar.

2. The composition according to claim 1, wherein said fungicide is propyl 3-(dimethylamino)propylcarbamate hydrochloride.

3. The composition according to claim 1, wherein said fungicide is 2,6-dichloro-N-[3-chloro-5-(trifluoromethyl)-2-pyridinylmethyl]benzamide and propyl 3-(dimethylamino)propylcarbamate hydrochloride.

4. The composition according to claim 1, wherein said fungicide is (2RS,3SR)-1-[3-(2-chlorophenyl)-2,3-epoxy-2-(4-fluorophenyl)propyl]-1H-1,2,4-triazole.

5. The composition according to claim 1, wherein said fungicide is 5,7-dichloro-4-quinolyl-4-fluorophenyl ether.

6. The composition according to claim 1, wherein said fungicide is sulphur.

7. The composition according to claim 1, wherein said fungicide is 4-chloro-2-cyano-N,N-dimethyl-5-(4-methylphenyl)-1H-imidazole-1-sulfonamide.

8. The composition according to any of claim 1, which further comprises a co-formulant selected from the group consisting of detergents, emulsifiers, dispersing agents, antifoaming agents, penetration enhancers, humectants, wetting agents of ionic or non-ionic type, anti-freeze agents, preservative agents, absorbent agents, thickeners, buffers, sticker agents, diluents, and a mixture thereof.

9. The composition according to claim 8, wherein said co-formulant is a surfactant selected from the group consisting of detergents, emulsifiers, dispersing agents, anti-foaming agents, penetration enhancers, humectants, wetting agents of ionic or non-ionic type, and a mixture thereof.

10. The composition according to claim 9, wherein said surfactant comprises one or more of the following components: castor oil ethoxylate, rapeseed methyl ester, alkyl phosphates, tributyl phosphate, tripropyl phosphate, naphthalenesulphonic acid salts, a combination of organic sulfonate and 2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyoxyethylene (20) sorbitan monolaurate.

11. The composition according to claim 10, wherein said surfactant is selected from the group consisting of C18-castor-oil-ethoxylate, a combination of organic sulfonate and 2-methylpentane-2,4-diol, and polyoxyethylene (20) sorbitan monolaurate.

12. The composition according to claim 1, which further comprises a further plant defense elicitor.

13. A method for protecting plants against plant pathogens comprising applying an effective and substantially non-phytotoxic amount of the composition according to claim 1 to said plants.

14. A method for enhancing the efficacy of a fungicide, comprising adding an elicitor comprising one or more oligogalacturonan(s) with a degree of polymerization between 9 and 20 and one or more chito-oligosaccharide(s) with a degree of polymerization between 5 and 10 and a degree of acetylation lower than 50% in proportions ranging from 1:10 to 10:1, to said fungicide, wherein said fungicide is selected from the group consisting of 2,6-dichloro-N-[3-chloro-5-(trifluoromethyl)-2-pyridinylmethyl]benzamide; propyl 3-(dimethylamino)propylcarbamate hydrochloride; (2RS,3SR)-1-[3-(2-chlorophenyl)-2,3-epoxy-2-(4-fluorophenyl)propyl]-1H-1,2,4-triazole; 5,7-dichloro-4-quinolyl 4-fluorophenyl ether; sulphur; 4-chloro-2-cyano-N,N-dimethyl-5-(4-methylphenyl)-1H-imidazole-1-sulfonamide; and a combination thereof.

15. The method according to claim 14, wherein said fungicide is propyl 3-(dimethylamino)propylcarbamate hydrochloride.

16. The method according to claim 14, wherein said fungicide is 2,6-dichloro-N-[3-chloro-5-(trifluoromethyl)-2-pyridinylmethyl]benzamide and propyl 3-(dimethylamino)propylcarbamate hydrochloride.

17. The method according to claim 14, wherein said fungicide is (2RS,3SR)-1-[3-(2-chlorophenyl)-2,3-epoxy-2-(4-fluorophenyl)propyl]-1H-1,2,4-triazole.

18. The method according to claim 14, wherein said fungicide is 5,7-dichloro-4-quinolyl 4-fluorophenyl ether.

19. The method according to claim 14, wherein said fungicide is sulphur.

20. The method according to claim 14, wherein said fungicide is 4-chloro-2-cyano-N,N-dimethyl-5-(4-methylphenyl)-1H-imidazole-1-sulfonamide.

21. The method according to claim 14, wherein the composition is applied before harvest or post harvest to the whole plant, the leaves, the flowers, fruits, seeds, seedlings or seedlings pricking out, propagation material, plants pricking out, and/or to the soil or inert substrate wherein the plant is growing or in which it is desired to grow, by spraying, drenching, soaking, dipping, injection or administration through fertilising or irrigation systems.

22. The method according to claim 14, wherein said plant is selected from the group consisting of cotton, flax, vine, fruit, vegetable, major horticultural and forest crops.

23. The method according to claim 13, wherein said plant pathogen is selected from the group consisting of fungi, oomycetes, bacteria, viruses, nematodes and insects.

24. The method according to claim 14, wherein said composition additionally comprises a surfactant selected from the group consisting of detergents, emulsifiers, dispersing agents, anti-foaming agents, penetration enhancers, humectants, wetting agents of ionic or non-ionic type, and a mixture thereof.

25. The method according to claim 24, wherein said surfactant comprises one or more of the following components: castor oil ethoxylate, rapeseed methyl ester, alkyl phosphates, tributyl phosphate, tripropyl phosphate, naphthalenesulphonic acid salts, a combination of organic sulfonate and 2-methylpentane-2,4-diol, alkylpolyglucoside, siloxanes derivates, alkylsulfonates, polycarboxylates, lignosulfonates, alkoxylated triglycerides, fatty amines polymers, dioctylsulfosuccinates or polyoxyethylene (20) sorbitan monolaurate.

26. The method according to claim 13 for enhancing the efficacy of said fungicide in said composition.

27. The method according to claim 13 for stimulating the plant immune system.

28. The method according to claim 21, wherein said propagation material are tubers or rhizomes.

29. The method according to claim 22, wherein said plant is selected from the group consisting of *Rosaceae* sp., *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp., *Rubiaceae* sp., *Theaceae* sp., *Sterculiceae* sp., *Rutaceae* sp., *Solanaceae* sp., *Vitaceae* sp., *Liliaceae* sp., *Asteraceae* sp., *Umbelliferae* sp., *Cruciferae* sp., *Chenopodiaceae* sp., *Cucurbitaceae* sp., *Papilionaceae* sp., *Gramineae* sp., and *Fabacae* sp.

\* \* \* \* \*